United States Patent
Kondo et al.

(10) Patent No.: US 10,067,142 B2
(45) Date of Patent: Sep. 4, 2018

(54) METHOD FOR DIAGNOSING, TREATING, OR PREVENTING MOOD DISORDER

(71) Applicants: JAPAN TOBACCO INC., Tokyo (JP); VIRUS IKAGAKU KENKYUSHO INC., Toyonaka-shi, Osaka (JP)

(72) Inventors: Kazuhiro Kondo, Tokyo (JP); Nobuyuki Kobayashi, Tokyo (JP); Naomi Oka, Tokyo (JP)

(73) Assignees: JAPAN TOBACCO INC., Tokyo (JP); VIRUS IKAGAKU KENKYUSHO INC., Toyonaka-Shi (JP)

( * ) Notice: Subject to any disclaimer, the term of this patent is extended or adjusted under 35 U.S.C. 154(b) by 0 days.

(21) Appl. No.: 15/321,884

(22) PCT Filed: Jun. 25, 2015

(86) PCT No.: PCT/JP2015/069080
§ 371 (c)(1),
(2) Date: Dec. 23, 2016

(87) PCT Pub. No.: WO2015/199247
PCT Pub. Date: Dec. 30, 2015

(65) Prior Publication Data
US 2017/0138957 A1 May 18, 2017

Related U.S. Application Data

(60) Provisional application No. 62/018,005, filed on Jun. 27, 2014.

(51) Int. Cl.
| | | |
|---|---|---|
| G01N 33/68 | (2006.01) |
| A61K 9/00 | (2006.01) |
| A61K 51/08 | (2006.01) |
| A61K 35/76 | (2015.01) |
| G01N 33/50 | (2006.01) |
| A61K 9/12 | (2006.01) |

(52) U.S. Cl.
CPC .............................. G01N 33/6854 (2013.01)

(58) Field of Classification Search
CPC combination set(s) only.
See application file for complete search history.

(56) References Cited

U.S. PATENT DOCUMENTS

| | | | | |
|---|---|---|---|---|
| 8,642,045 B2 * | 2/2014 | Konda | ................. | C12N 15/86 424/199.1 |
| 9,139,617 B2 * | 9/2015 | Takakura | ............ | C07K 14/005 |
| 2006/0034855 A1 | 2/2006 | Solomon | | |
| 2008/0280283 A1 | 11/2008 | Kondo | | |
| 2009/0068253 A1 * | 3/2009 | Guilford | ............. | A61K 9/0019 424/450 |
| 2010/0247486 A1 * | 9/2010 | Kondo | .................. | C12N 15/86 424/93.2 |
| 2010/0281550 A1 | 11/2010 | Kondo et al. | | |
| 2011/0053145 A1 * | 3/2011 | Takakura | ........ | G01N 33/56983 435/5 |
| 2011/0166106 A1 * | 7/2011 | Marschall | ............. | A61K 31/12 514/86 |
| 2012/0107842 A1 * | 5/2012 | Takakura | ............ | C07K 14/005 435/7.92 |
| 2013/0137088 A1 * | 5/2013 | Kondo | ................ | C07K 14/005 435/5 |
| 2013/0217044 A1 * | 8/2013 | Kondo | ................ | C07K 14/005 435/7.92 |
| 2016/0068918 A1 * | 3/2016 | Kondo | ................... | A61B 5/16 435/5 |

FOREIGN PATENT DOCUMENTS

| | | |
|---|---|---|
| EP | 0 615 750 A2 | 9/1994 |
| EP | 2199391 A1 | 6/2010 |
| EP | 2416158 A1 | 2/2012 |
| JP | 11-196870 A | 7/1999 |
| JP | 4218842 B2 | 11/2008 |
| JP | 4920084 B2 | 2/2012 |
| JP | 2012-110329 A | 6/2012 |
| JP | 2013-150553 A | 8/2013 |
| JP | 2013-181034 A | 9/2013 |
| JP | 2014-19658 A | 2/2014 |

OTHER PUBLICATIONS

Wen MM. Olfactory targeting through intranasal delivery of biopharmaceutical drugs to the brain: current development. Discov Med. Jun. 2011;11(61):497-503.*
Harberts E, Yao K, Wohler JE, Maric D, Ohayon J, Henkin R, Jacobson S. Human herpesvirus-6 entry into the central nervous system through the olfactory pathway. Proc Natl Acad Sci U S A. Aug. 16, 2011;108(33):13734-9. Epub Aug. 8, 2011.*
Kalinke U, Bechmann I, Detje CN. Host strategies against virus entry via the olfactory system. Virulence. Jul.-Aug. 2011;2(4):367-70. Epub Jul. 1, 2011, Review. PubMed PMID: 21758005.*
Kogelnik AM, Loomis K, Hoegh-Petersen M, Rosso F, Hischier C, Montoya JG. Use of valganciclovir in patients with elevated antibody titers against Human Herpesvirus-6 (HHV-6) and Epstein-Barr Virus (EBV) who were experiencing central nervous system dysfunction including long-standing fatigue. J Clin Virol. Dec. 2006.*
Milho R, Frederico B, Efstathiou S, Stevenson PG. A heparan-dependent herpesvirus targets the olfactory neuroepithelium for host entry. PLoS Pathog. 2012;8(11):e1002986. doi: 10.1371/journal.ppat.1002986. Epub Nov. 1, 2012.*

(Continued)

*Primary Examiner* — Rachel B Gill
(74) *Attorney, Agent, or Firm* — Birch, Stewart, Kolasch & Birch, LLP

(57) ABSTRACT

An object of the present invention is to provide a novel method of diagnosing and/or treating a mood disorder, the method being superior to the conventional technologies. The present invention attains the object by providing a method of diagnosing and/or treating a mood disorder by use of an anti-SITH-1 antibody level and an anti-HHV-6 antibody level each serving as an index.

6 Claims, 19 Drawing Sheets
(14 of 19 Drawing Sheet(s) Filed in Color)
Specification includes a Sequence Listing.

(56) References Cited

OTHER PUBLICATIONS

Aug. 8, 2011: https://www.sciencenews.org/article/common-virus-may-ride-nose-brain. Sanders, L. Common virus may ride up nose to brain. Science News.*

Aug. 9, 2011: https://hhv-6foundation.org/news/hhv-6a-can-travel-through-the-nose-to-the-brain. HHV-6 Foundation. HHV-6a Can Travel Through the Nose to the Brain.*

Jul. 10, 2013: https://hhv-6foundation.org/associated-conditions/hhv-6-and-chronic-fatigue-syndrome. HHV-6 Foundation. HHV-6 & Chronic Fatigue Syndrome (CFS/ME).*

Johnson C. The Symposium on Viruses in Chronic Fatigue Syndrome (ME/CFS) (May 2008): Part I. Mar. 6, 2011. http://phoenixrising.me/conferences-2/the-symposium-viruses-in-chronic-fatigue-syndrome-mecfs-may-2008-part-i-by-cort-johnson.*

Phoenix Rising. ME/Chronic Fatigue Syndrome Forums. "Whatever happened to . . . research on SITH-1 protein made by HHV-6 in ME/CFS patients". Discussion in 'Antivirals, Antibiotics and Immune Modulators' started by Hip, Jan. 18, 2012. http://forums.phoenixrising.me/index.php?threads/whatever-happened-to-research-on-si.*

Kondo K, Kobayashi N. "Identification of a novel HHV-6 latent-protein associated with CFS and mood disorders." Symposia Brain Scinece on Fatigue: New Insights from Viral Reactivation, Cytokines, and Imaging (S3-10-2-1) Related Abstract. Sep. 4, 2010 15:25-15:50.*

Donati et al., "Variant-Specific Tropism of Human Herpesvirus 6 in Human Astrocytes," Journal of Virology (Aug. 2005), vol. 79, No. 15, pp. 9439-9448.

English tranlsation of International Preliminary Report on Patentability and Written Opinion dated Jan. 5, 2017, in PCT International Application No. PCT/JP2015/069080.

English Translation of International Search Report dated Sep. 29, 2015, in PCT International Application No. PCT/JP2015/069080.

Kondo et al., "Association of Human Herpevirus 6 Infection of the Central Nervous system with Recurrence of Febrile Convulsions," The Journal of Infectious Diseases (1993), vol. 167, pp. 1197-1200.

Tuke et al., "Distribution and quantification of human herpesvirus 6 in multiple sclerosis and control brains," Multiple Sclerosis (2004), vol. 10, pp. 355-359.

Extended European Search Report, dated Nov. 24, 2017, for European Application No. 15811939.6.

Kobayashi et al., "Identification of Novel HHV-6 Latent Protein Associated with Mood Disorders in CFS, Depressive Disorder, Bipolar Disorder and HHV-6 Encephalopathy," 6th International Conference on HHV-6 & 7, Baltimore, Maryland, USA, Jun. 22, 2008, 1 page.

* cited by examiner

METHOD FOR DIAGNOSING, TREATING, OR PREVENTING MOOD DISORDER

CROSS REFERENCE TO RELATED APPLICATIONS

This application is the National Phase of PCT/JP2015/069080 filed on Jun. 25, 2015, which claims priority under 35 U.S.C. § 119(e) to U.S. Provisional Application No. 62/018,005 filed on Jun. 27, 2014, all of which are hereby expressly incorporated by reference into the present application.

TECHNICAL FIELD

The present invention relates to a method of diagnosing, treating, or preventing a mood disorder. Specifically, the present invention relates to a novel method of diagnosing, treating, or preventing a mood disorder by use of a certain gene serving as an index.

BACKGROUND ART

A mood disorder, which is a mental disorder typified by depressive disorder and bipolar disorder, is recently becoming more prevalent and is becoming a major social problem. A mood disorder is basically treated by pharmacotherapy in which a tricyclic antidepressant, a selective serotonin reuptake inhibitor (SSRI), a serotonin and norepinephrine reuptake inhibitor (SNRI), and the like are used.

Human herpesvirus-6 (HHV) is a virus found in the peripheral blood of an AIDS patient, and belongs to a herpesvirus β subfamily. HHV-6 has two variants: HHV-6 variant A (HHV-6A) and HHV-6 variant B (HHV-6B). Most humans are initially infected by HHV-6B during infancy, and roseola infantum occurs at an onset. At an acute stage of initial infection, HHV-6B is transitioned into a brain and latently infects the brain with an extremely high probability. The latent infection remains after an infected person becomes an adult (Non-Patent Literature 1). Latent infection means an infection state in which a virus remains in a host cell without producing infectious viral particles. It is suggested that in a brain, mainly glial cells of a frontal lobe, a hippocampal region, and the like contract HHV-6B latent infection (Non-Patent Literatures 2 and 3). In addition, macrophages in peripheral blood also suffer HHV-6 latent infection, and fatigue developed by daily living or the like causes the HHV-6 to be reactivated and released into saliva (Patent Literature 1).

During latent infection with HHV-6, no virus is produced. It is known, however, that there exists an "intermediate stage" which is a relatively stable stage and in which gene is actively expressed. As a protein expressed in an intermediate stage, Small protein encoded by the Intermediate stage Transcript of HHV-6-1 (hereinafter referred to as "SITH-1") is identified (Patent Literature 2). Since an antibody against SITH-1 is detected specifically from a patient of a mood disorder such as depressive disorder, development has been made for a method of diagnosing a mood disorder, which method is characterized by detecting and measuring an anti-SITH-1 antibody in a specimen of a subject (Patent Literature 2). It has been also demonstrated that in a case where a SITH-1 gene, which was linked to a glial cell-specific expression promoter, was transfected into a brain of a mouse with use of an adenovirus vector and was expressed, the mouse exhibited behavioral abnormalities such as those caused by a mental disorder (Patent Literature 2).

CITATION LIST

Patent Literature

[Patent Literature 1]
Japanese Patent No. 4218842
[Patent Literature 2]
Japanese Patent No. 4920084

Non-Patent Literature

[Non-patent Literature 1]
Kondo K et al., J infect Dis, 167: 1197-1200, 1993
[Non-patent Literature 2]
Tuke et al., Multiple Sclerosis, 10: 355-359, 2004
[Non-patent Literature 3]
Donati et al., Journal of Virology Vol. 79, No. 15: 9439-9448, 2005

SUMMARY OF INVENTION

Technical Problem

However, the mechanism of an onset of a mood disorder cannot be deemed sufficiently understood yet. In regard to diagnosis and treatment of mood disorder, in particular, there are demands for further development of methods of diagnosing and treating a mood disorder.

Under the circumstances, an object of an embodiment of the present invention is to provide a novel method of diagnosing and/or treating a mood disorder, which method is superior to conventional techniques.

Solution to Problem

In order to attain the object, the inventors of the present invention conducted diligent study of a method of diagnosing and/or treating a mood disorder with sensitivity and specificity greater than those of conventional techniques. As a result, the inventors of the present invention found that measurement of a level of a particular antibody in a biological sample allows a mood disorder to be diagnosed and/or treated with high sensitivity and high specificity, and the present invention was thus achieved.

An embodiment of the present invention encompasses the following:

[1] A method of obtaining data for determining whether or not a subject has a mood disorder, including the steps of:
obtaining an anti-SITH-1 antibody level in a biological sample separated from the subject; and
obtaining an anti-HHV-6 antibody level in a biological sample separated from the subject.

[2] A method of diagnosing a subject by determining whether or not the subject has a mood disorder, including the steps of:
measuring an anti-SITH-1 antibody level in a biological sample separated from the subject;
measuring an anti-HHV-6 antibody level in a biological sample separated from the subject; and
in a case where the anti-SITH-1 antibody level and the anti-HHV-6 antibody level are high and low, respectively, determining that the subject has the mood disorder.

[3] A diagnostic kit for carrying out a method recited in [2].

[4] A method of treating a mood disorder, wherein infection of cells in olfactory epithelium of a subject with HHV-6 is restricted.

[5] A method of treating a mood disorder, including the step of:
administering an HHV-6 infection inhibitor to a subject.

[6] A method of treating a mood disorder, including the steps of:
measuring an anti-SITH-1 antibody level in a biological sample separated from a subject; and
in a case where the anti-SITH-1 antibody level is high, administering an HHV-6 infection inhibitor to the subject.

[7] A method of treating a mood disorder, including the step of:
administering an HHV-6 infection inhibitor to a subject who has been diagnosed with a mood disorder by a method recited in [2].

[8] The method as set forth in [6] or [7], wherein the HHV-6 infection inhibitor is administered to cells in olfactory epithelium of the subject.

[9] A method of treating a mood disorder, including the steps of:
measuring an anti-HHV-6 antibody level in a biological sample separated from a subject; and
in a case where the anti-HHV-6 antibody level is low, administering an HHV-6 infection inhibitor to the subject.

[10] The method as set forth in [9], wherein
the HHV-6 infection inhibitor is administered to cells in olfactory epithelium of the subject.

[11] A mood disorder treatment agent including:
an HHV-6 infection inhibitor.

[12] Transformed cells in olfactory epithelium obtained by transfecting cells in the olfactory epithelium with a SITH-1 gene.

[13] A mood disorder model animal obtained by transfecting cells in olfactory epithelium with a SITH-1 gene.

[14] A method of screening for a candidate substance for a mood disorder treatment agent, including the steps of:
administering a test substance to a mood disorder model animal recited in [13]; and
determining, by using as an index at least one of the following factors of the mood disorder model animal, whether or not the test substance is a candidate substance for a mood disorder treatment agent:
(a) a behavioral abnormality test,
(b) a stress vulnerability test,
(c) a test for detecting apoptosis in an olfactory bulb,
(d) a test for detecting an abnormality of a hypothalamus, and
(e) a test for detecting an abnormality of a stress response factor in a brain.

Advantageous Effects of Invention

According to an embodiment of the present invention, a certain gene related to a mood disorder is used as an index. This makes it possible to determine, with higher sensitivity and higher specificity than are the cases of the conventional technologies, whether or not a subject has a mood disorder. With an embodiment of the present invention, it is possible to effectively treat or prevent a mood disorder of a subject by (i) inhibiting infection of the olfactory epithelium with a virus related to a mood disorder or (ii) dealing with an impairment caused by a certain gene which is expressed by the virus and which is related to a mood disorder. A mood disorder model animal in accordance with an embodiment of the present invention has such excellent characteristics as exhibiting (i) olfactory cell impairment, (ii) an abnormality of a hypothalamus, (iii) abnormal expression of a stress response factor in the brain, and (iv) stress vulnerability. An embodiment of the present invention also uses a mood disorder model animal transfected with a certain gene related to a mood disorder. This allows efficient screening for a candidate substance for a mood disorder treatment agent.

BRIEF DESCRIPTION OF DRAWINGS

The patent or application file contains at least one color drawing. Copies of this patent or patent application publication with color drawing will be provided by the USPTO upon request and payment of the necessary fee.

DESCRIPTION OF EMBODIMENTS

Figure 1:
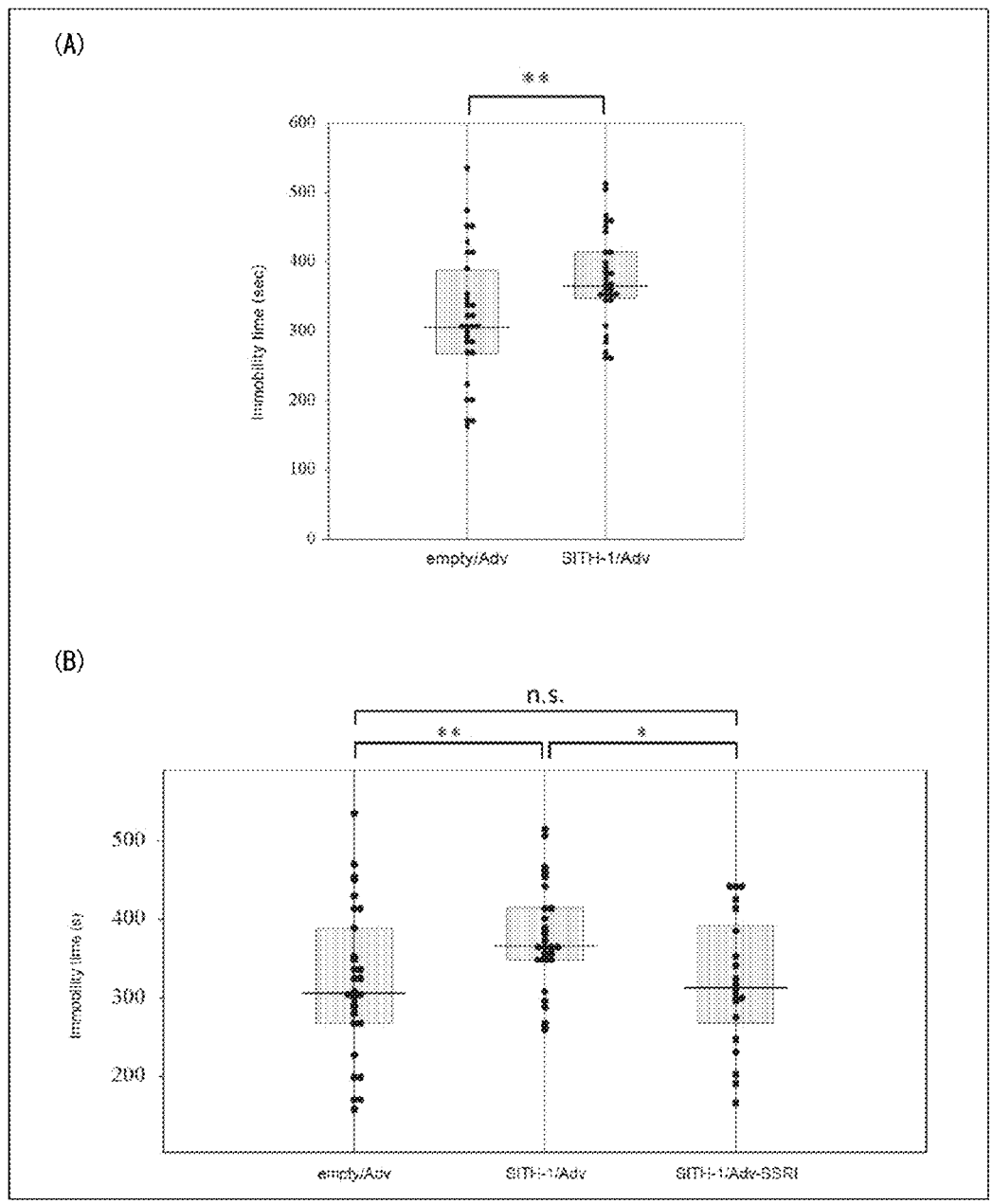
FIG. 1 shows the results of immobility time in a tail suspension test. (A) of FIG. 1 is a view showing the results of carrying out tail suspension tests of 30 empty/Adv nasal administration mice and 30 SITH-1/Adv nasal administration mice for 10 minutes, and then comparing respective periods of immobility time. (B) of FIG. 1 is a view showing the results of carrying out, for 10 minutes, a tail suspension test of 21 mice to which an SSRI had been administered since 2 weeks before nasal administration of SITH-1/Adv and then comparing periods of immobility time (SITH-1/Adv-SSRI).

The following description will discuss an embodiment of the present invention in detail. Note that all of the academic documents and patent literatures listed herein are incorporated by reference herein. Unless otherwise specified herein, "A to B" which indicates a numerical range means "equal to or greater than A and equal to or less than B".

[1] Explanation of Terms

First, the main terms used herein will be explained below.

In an embodiment of the present invention, "mood disorder" refers to a state in which a continuous change in mood (emotion) for a certain period of time causes a feeling of disturbance and/or interferes with daily living in a certain manner. Representative examples of the mood disorder encompass (i) depressive disorder with which only depression is observed as a symptom and (ii) bipolar disorder with which manic states and depressive states are repeated. Although various causes for mood disorder are considered, many details are unknown. Medically, mood disorders are manipulatively diagnosed according to diagnostic criteria set by (i) the DSM (Diagnostic and Statistical Manual of Mental Disorders) which is introduced by the American Psychiatric Association or (ii) the ICD (International Statistical Classification of Diseases and Related Health Problems) which is an international standard for diseases.

"Biological sample" is not limited to any particular one, provided that the biological sample is derived from a living organism and allows measurement of the amount of antibody, antibody titer, or the amount of HHV-6. The biological sample is preferably one or more selected from the group consisting of blood, serum, plasma, cerebrospinal fluid, saliva, nasal discharge, sweat, lymph, and breast milk. In a case where an antibody is to be detected, the biological sample is preferably blood, serum, plasma, or cerebrospinal fluid. A biological sample for use in detection of the anti-SITH-1 antibody, a biological sample for use in detection of the anti-HHV-6 antibody, and a biological sample for use in measurement of the amount of HHV-6 can be identical or different. The biological sample for use in measurement of the amount of HHV-6 is more preferably saliva.

According to an embodiment of the present invention, "HHV-6" refers to human herpesvirus-6 (HHV: human herpesvirus) and belongs to β-herpesvirus. While there exist two variants of HHV-6 (i.e. HHV-6 variant A (HHV-6A) and HHV-6 variant B (HHV-6B)), HHV-6 according to an embodiment of the present invention is preferably HHV-6B.

According to an embodiment of the present invention, "SITH-1" refers to Small protein encoded by the Intermediate stage Transcript of HHV-6 (Small protein encoded by latent infection intermediate stage transcript of HHV-6)-1. The "SITH-1" was found as a factor involved in latent infection with human herpesvirus-6, more specifically as a protein expressed during latent infection with herpesvirus. Furthermore, the inventors of the present invention found in Examples disclosed herein that SITH-1 is expressed during non-productive infection of an astrocyte-based cell (see FIG. 14). SITH-1 protein is a protein (GenBank accession numbers: HV763913.1 and HV763914.1) which consists of 159 amino acids and which has a molecular weight of approximately 17.5 kDa. A nucleotide sequence (SEQ ID NO. 2) of a nucleic acid encoding SITH-1 protein will be described later.

According to an embodiment of the present invention, "antibody" refers to an immunoglobulin (IgA, IgD, IgE, IgG, and IgM; and Fab fragments of IgA, IgD, IgE, IgG, and IgM, F(ab')$_2$ fragments thereof, and Fc fragments thereof). Examples of the "antibody" encompass, but are not limited to, a polyclonal antibody, a monoclonal antibody, a single-chain antibody, an anti-idiotype antibody, and a humanized antibody.

According to an embodiment of the present invention, "anti-SITH-1 antibody" refers to an antibody which recognizes SITH-1 protein and which contains (i) a complete molecule that can be bound specifically to SITH-1 protein and (ii) an antibody fragment (e.g. Fab fragment and F(ab')$_2$ fragment) that can be bound specifically to SITH-1 protein. An anti-SITH-1 antibody is preferably IgG.

According to an embodiment of the present invention, an anti-SITH-1 antibody can be, but is not limited to, an antibody having higher antigen binding force, that is, a high-avidity antibody. An IgG antibody in an initial phase of infection has weak antigen binding force, and high-avidity antibodies are produced as the infection progresses. Such a high-avidity antibody can be detected and measured by, for example, washing an antibody of a subject with use of a protein denaturating agent-containing washing liquid during a process of washing the antibody of the subject in an assay system. Examples of such a protein denaturating agent encompass urea, guanidine salt, and sodium dodecyl sulfate. The protein denaturating agent is preferably urea.

According to an embodiment of the present invention, "anti-HHV-6 antibody" refers to an antibody which recognizes HHV-6 and which contains (i) a complete molecule that can be bound specifically to HHV-6 particles and (ii) an antibody fragment (e.g. Fab fragment and F(ab')$_2$ fragment) that can be bound specifically to HHV-6 particles. The anti-HHV-6 antibody is preferably an antibody which recognizes HHV-6B. Preferable examples of the anti-HHV-6 antibody encompass IgM, IgG, and IgA. In a case where a biological sample is blood, plasma, serum, or the like, preferable examples of the anti-HHV-6 antibody encompass, but are not limited to, IgG. In a case where a biological sample is saliva or a nasal discharge, preferable examples of the anti-HHV-6 antibody encompass, but are not limited to, IgA. The anti-HHV-6 antibody can be, but is not limited to, a neutralizing antibody of HHV-6. Alternatively, the anti-HHV-6 antibody can be a high-avidity antibody.

According to an embodiment of the present invention, "antibody level" refers to an amount of an antibody contained in a biological sample or to a titer of the antibody. The amount of antibody and the antibody titer can each be measured by use of a well-known method. Examples of the well-known method for measurement of an antibody level encompass, but are not limited to, assays which use traditional immunohistological methods such as (indirect) fluorescent antibody method, dot blot assay, Western blotting, enzyme-linked immunosorbent assay (including ELISA and sandwich ELISA), radioimmunoassay (RIA), and immunodiffusion assay. Alternatively, the antibody can be measured by in-vivo image analysis or the like.

An index for judging an antibody level of a high-avidity antibody can be an Avidity Index. The Avidity Index can be obtained by, for example, dividing a first amount of antibody by a second amount of antibody during a process of washing the antibody of a subject in an assay system, the first amount of antibody being measured with use of a protein denaturating agent-containing washing liquid, and the second amount of antibody being measured with use of a protein denaturating agent-free ordinary washing liquid. Examples of such a protein denaturating agent encompass urea, guanidine salt, and sodium dodecyl sulfate. The protein denaturating agent is preferably urea.

Figure 12:
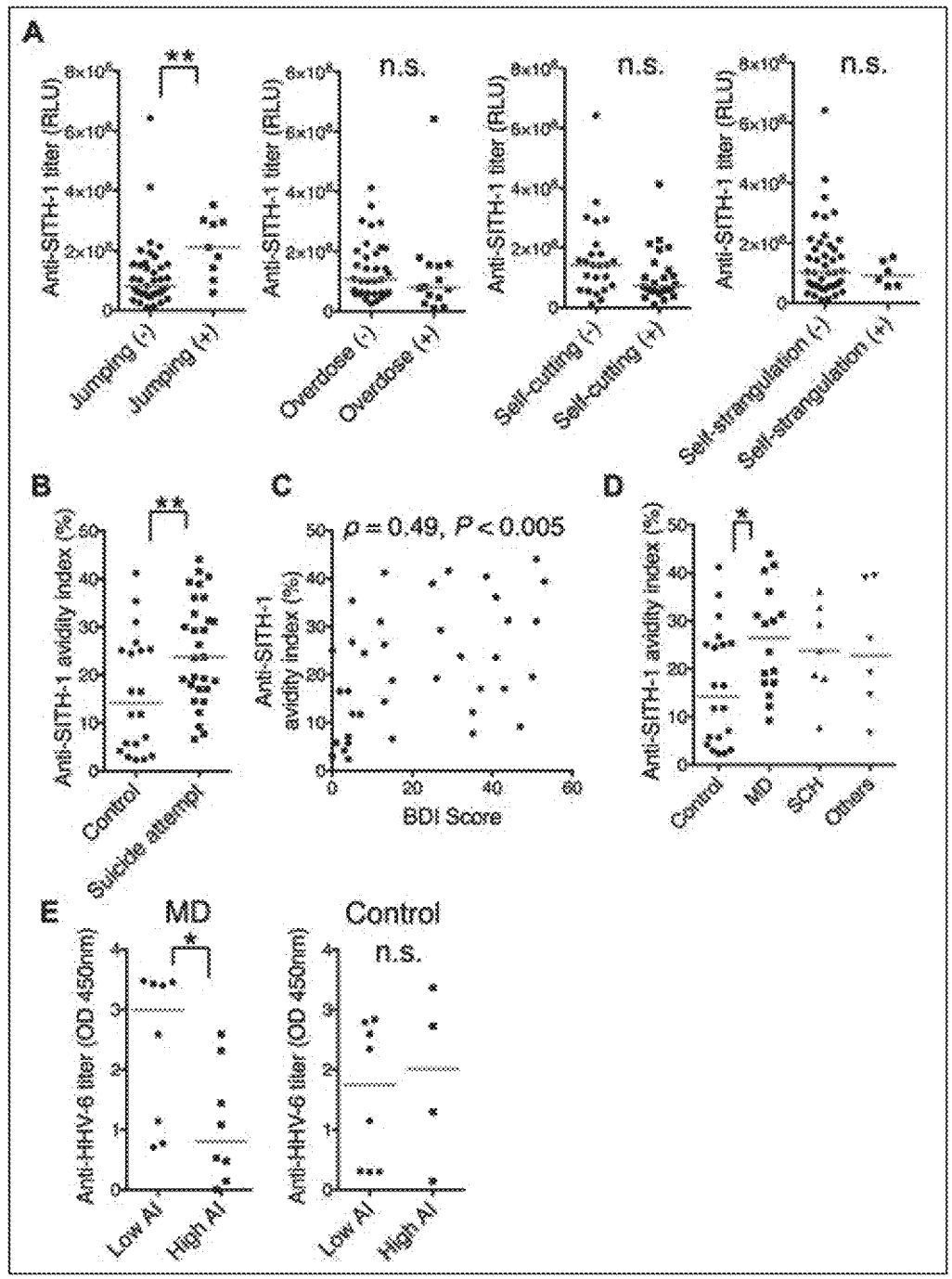
FIG. 12 shows SITH-1 exposure and clinical symptoms. A of FIG. 12 is a view showing comparison of anti-SITH-1 antibody titers according to the following methods of attempted suicide: jumping, drug overdose, self-cutting, and self-strangulation. B of FIG. 12 is a view showing anti-SITH-1 antibody avidity index (AI) in healthy subjects (controls) and subjects who had attempted suicide. C of FIG. 12 is a view showing a relationship between anti-SITH-1 AI and Beck Depression Index (BDI) total score. D of FIG. 12 is a view showing comparison of anti-SITH-1 antibody AIs in healthy subjects (controls) and patients with mood disorders (MD), schizophrenia or other psychotic disorders (SCH), and other mental disorders (Others). E of FIG. 12 is a view showing a relationship between anti-HHV-6B antibody and anti-SITH-1 antibody AI in patients who were diagnosed as having MD and healthy subjects (controls).

[2] Relationship between level of anti-SITH-1 antibody and/or anti-HHV-6 antibody and mood disorder and other factors The inventors of the present invention found that anti-HHV-6 antibody levels of mood disorder patients having high anti-SITH-1 antibody levels are significantly lower than those of mood disorder patients having low anti-SITH-1 antibody levels (see E of FIG. 12). This was unexpected and surprising in view of the facts that (i) SITH-1 is an HHV-6 latent infection-specific protein and (ii) an increase in reactivated viruses generally causes an increase in antibodies against the viruses. Because of this finding, it has been made possible to considerably increase sensitivity and specificity of a mood disorder diagnosing method by measurement of anti-SITH-1 antibody. Specifically, although part of healthy subjects have high anti-SITH-1 antibody levels (subjects with false positives), selection of subjects having low anti-HHV-6 antibody levels from subjects having high anti-SITH-1 antibody levels causes a large number of healthy subjects with false positives of anti-SITH-1 antibody to be removed. This allows for an enormous increase in probability that remaining subjects are mood disorder patients.

An aspect of the present invention is thus a diagnosing method of determining whether or not a subject has a mood disorder, the method including the steps of: measuring an anti-SITH-1 antibody level of a biological sample separated from the subject; measuring an anti-HHV-6 antibody level of a biological sample separated from the subject; and determining, if the anti-SITH-1 antibody level and the anti-HHV-6 antibody level are high and low, respectively, that the subject has a mood disorder. Note that a method of obtaining data for such diagnosis is an aspect of the present invention. In addition, according to an aspect of the present invention, an Avidity Index can be used as an index of an antibody level of an anti-SITH-1 antibody, preferably a high-avidity anti-SITH-1 antibody. In a case where a value of an Avidity Index is high, it is possible to determine that an antibody level of a high-avidity antibody is high.

The inventors of the present invention also found that symptoms of mood disorder of patients having high anti-SITH-1 antibody levels are more severe than those of patients having low anti-SITH-1 antibody levels (see C of FIG. 12). An aspect of the present invention is thus a diagnosing method of determining the degree of a mood disorder of a subject, including the steps of: measuring an anti-SITH-1 antibody level of a biological sample separated from the subject; and determining, if the anti-SITH-1 antibody level is high, that a symptom of the mood disorder is more severe.

Note that in a case where cells in olfactory epithelium are frequently infected with HHV-6, symptoms of a mood disorder become severer as described later. Therefore, anti-SITH-1 antibody to be measured can be high-avidity antibody. A method of obtaining data for such diagnosis in accordance with an embodiment of the present invention is an aspect of the present invention.

A person skilled in the art can properly set a threshold in view of (i) a quantitative value (normal value) of a healthy subject, (ii) a quantitative value (disease level) of a typical mood disorder patient, (iii) a quantitative value (disease level) of a mild mood disorder patient, (iv) a quantitative value (disease level) of a moderate mood disorder patient, or (v) a quantitative value (disease level) of a severe mood disorder patient. That is, in general, a threshold (i.e. cutoff value) of a diagnosis is properly set according to a purpose of the diagnosis by a person skilled in the art on the basis of multiple measured values of healthy subjects and patients which values are obtained from clinical trials. (As an example, in a case where, as with a screening examination, a definite diagnosis is to be made in a secondary examination or subsequent examinations so as to most prioritize prevention of overlooking a disease group, sensitivity is prioritized over specificity so that a cutoff value is set low. As another example, in a case where a degree of a symptom of a mood disorder is to be determined, a threshold is to be set high in view of respective quantitative values of mild mood disorder patients, moderate mood disorder patient, and severe mood disorder patient.) Based on the disclosure herein, a person skilled in the art can easily decide a threshold for a diagnosis.

Specifically, for example, whether or not "an antibody level is high" can be determined by whether or not the measured antibody level is higher than the threshold (e.g. an antibody level of a healthy subject). Whether or not "an antibody level is low" can be determined by whether or not the measured antibody level is lower than the threshold.

Note that a method of obtaining data for making a diagnosis in accordance with an embodiment of the present invention is also an aspect of the present invention. That is, a method of obtaining data for making a diagnosis, which method includes each step involved in the above-mentioned diagnosing method is also encompassed in an embodiment of the present invention.

An antibody level of HHV-6 can be used for assessing a risk of HHV-6 encephalitis. Specifically, in a case where an antibody level of HHV-6 is low, it can be judged that a risk of HHV-6 encephalitis is high. In a case where an antibody level of HHV-6 is high, it can be judged that a risk of HHV-6 encephalitis is low. In the case where the antibody level of HHV-6 is low, an antiviral agent or the like can be administered to a subject prophylactically.

According to an embodiment of the present invention, a "kit" can be any kit, provided that the kit is to be used for carrying out the detecting method in accordance with an embodiment of the present invention or the diagnosing method in accordance with an embodiment of the present invention. While a specific configuration, specific material, specific apparatus and the like of the kit are not limited to any particular ones, the kit preferably includes any of the following (1) through (3) in order to immunologically detect an anti-SITH-1 antibody: (1) SITH-1 protein; (2) a partial fragment (preferably containing epitope-containing peptides of the SITH-1 protein (1); and (3) a detection instrument in which the SITH-1 protein (1) or the partial fragment (2) is fixed. The kit preferably includes any of the following materials in order to immunologically detect an anti-HHV-6 antibody: (1) HHV-6 coat protein; (2) a partial fragment (preferably containing epitope-carrying peptides of the HHV-6 coat protein (1); and (3) a detection instrument in which the HHV-6 coat protein (1) or the partial fragment (2) is fixed.

According to an embodiment of the present invention, the SITH-1 protein/HHV-6 coat protein (1) or the partial fragment (2) can be fixed to any carrier, provided that the carrier is a solid carrier or an insoluble material (e.g. material which can be separated from a reaction mixture by filtering, precipitation, magnetic separation, or the like). Examples of a shape of the solid carrier encompass, but are not limited to, shapes of beads, magnetic beads, thin film, microtubule, filter, plate, microplate, carbon nanotube, and sensor chip. In a case where the solid carrier is flat such as a thin film or a plate, the solid carrier can have a pit, a groove, a filtering bottom part, or the like as known in the technical field.

According to an embodiment of the present invention, the SITH-1 protein/HHV-6 coat protein (1) or the partial fragment (2) can be fixed to a cell for expressing the SITH-1 protein/HHV-6 coat protein (1) or the partial fragment (2). In a case where, in particular, measurement is carried out by a (indirect) fluorescent antibody method, the SITH-1 protein/HHV-6 coat protein (1) or the partial fragment (2) is preferably fixed to such a cell. Note that a person skilled in the art can select an appropriate cell in view of a known technique. Preferable examples of the cell encompass a human-derived cell, a monkey-derived cell, and an insect cell. A human-derived cell is most preferable.

According to an embodiment of the present invention, "treatment" encompasses (i) alleviating a symptom of a mood disorder or causing the symptom of the mood disorder to completely disappear and (ii) restricting deterioration of the symptom of the mood disorder. According to an embodiment of the present invention, "prevention" encompasses preventing an onset of a symptom of a mood disorder or retarding the onset of the symptom of the mood disorder.

[3] Relationship between HHV-6 and mood disorder and other factors

The inventors of the present invention thus found the earlier-described relationship between a mood disorder and an amount of anti-HHV-6 antibody. In addition, it is known that olfactory epithelium is the part that becomes infected with HHV-6 (see Literature 11). Based on these facts, the inventors of the present invention continuously carried out diligent research with the focus on a relationship between infection of cells in olfactory epithelium with HHV-6 and a mood disorder. As a result, the inventors of the present invention obtained surprising results.

Specifically, the inventors of the present invention expressed SITH-1 genes in olfactory epithelium cells (which refers to cells in olfactory epithelium including olfactory ensheathing cells in this specification) of mice. As a result, the mice (hereinafter referred to as "SITH-1-expressing mice") experienced impairment of olfactory cells and further experienced stress vulnerability. That is, the mice experienced an onset of a mood disorder. This means that even if parts of the brain are not infected with HHV-6 or HHV-6 is not transitioned to the parts of the brain, a mood disorder can occur only with an expression of SITH-1 in the cells in the olfactory epithelium. These were surprising results.

Examples of the impairment of the olfactory cells encompass apoptosis of olfactory bulb cells. Olfactory bulbs of SITH-1-expressing mice exhibited larger increases of Bax-to-Bcl-2 ratios (which serve as an index of apoptosis) than those of the control mice did (see Example 2.3). In addition, in observation of tissue of the olfactory bulbs by TUNEL staining, a larger number of apoptotic cells were detected in the SITH-1-expressing mice (see Example 2.4).

In addition, abnormal production of CRH (corticotropin-releasing hormone) and urocortin was observed in the whole brains of the SITH-1-expressing mice (see Example 2.3). Since CRH and urocortin are biomarkers of a hypothalamus, abnormal production thereof strongly suggests that some kind of abnormalities occurred in the hypothalami. Furthermore, increases in expression level of REDD1, which is a stress response factor in a brain, were also observed (see Example 2.3).

Then, when the SITH-1-expressing mice were subjected to mild stress, the SITH-1-expressing mice exhibited symptoms of a mood disorder (see Example 2.5). This suggests that the SITH-1-expressing mice exhibited stress vulnerability. Note that stress vulnerability refers a state in which a proper response cannot be made to a low level of stressor.

It was further found as a result of behavioral abnormality tests (tail suspension tests) that the SITH-1-expressing mice had a prolonged period of immobility time, and were therefore in a depressive state (see Example 2.2). These behavioral abnormalities were improved by administration of SSRI (selective serotonin reuptake inhibitor) (see Example 2.2).

Based on the series of these results, the inventors of the present invention found the following action mechanism in regard to an onset of a mood disorder caused by HHV-6.

That is, in a case where olfactory epithelium is infected with HHV-6 and therefore expresses SITH-1 protein, an olfactory system is impaired. This causes apoptosis of olfactory bulb cells. Such dysfunction of the olfactory system causes a strong incorrect signal to be transmitted to the hypothalamus, and consequently causes "stress vulnerability" which is a state in which an incorrect stress response can easily occur. Then, in a case where "stress vulnerability" occurs, a response to even a mild level of stress in an environment becomes excessive. This causes an onset of a mood disorder. Note that the present invention is not limited to this action mechanism.

The inventors of the present invention thus found that the infection of cells in olfactory epithelium with HHV-6 causes expression of SITH-1, so as to cause a variety of impairment. Note that "impairment" herein refers to impairment of olfactory cells, an abnormality of hypothalamus, abnormal expression of a stress response factor in a brain, stress vulnerability, and a mood disorder. Examples of the impairment of the olfactory cells encompass, but are not limited to, an increase in apoptosis of the olfactory cells. Examples of the abnormality of the hypothalamus encompass, but are not limited to, abnormal production of CRH and/or urocortin. Examples of the stress response factor in the brain which are abnormally expressed encompass, but are not limited to, REDD1.

Therefore, an embodiment of the present invention provides a method of treating the impairment, the method being characterized by restricting infection of cells in olfactory epithelium with HHV-6.

Note that while "treatment" and "prevention" are herein defined as described above, the action mechanism in accordance with an embodiment of the present invention does not vary between "treatment" and "prevention". Therefore, a "treatment method" and a "prevention method" can be interchangeably used. Specifically, in a case where a subject is not suffering an impairment caused by SITH-1, "treatment" means "prevention". Hence, an aspect of the present invention naturally encompasses (i) a method of preventing a mood disorder, the method being characterized by restricting infection of cells in olfactory epithelium of a subject with HHV-6 and (ii) a method of preventing a mood disorder, the method being characterized by administering an HHV-6 infection inhibitor to a subject.

According to an embodiment of the present invention, it is possible to use an HHV-6 infection inhibitor for restricting infection of cells in olfactory epithelium with HHV-6.

The HHV-6 infection inhibitor in accordance with an embodiment of the present invention can be any inhibitor, provided that the inhibitor can inhibit infection of cells with HHV-6. Preferable examples of the HHV-6 infection inhibitor encompass anti-HHV-6 antibodies, heparan sulfate, heparin, HHV-6 vaccines, sugar hydrolase (glycosidase) inhibitors, protease inhibitors, peptides, sugar chains, sugar chain-polypeptides, and sugar derivatives. More preferable examples of the HHV-6 infection inhibitor encompass heparan sulfate, heparin, and HHV-6 vaccines. These HHV-6 infection inhibitors can be combined as appropriate. Preferable examples of the anti-HHV-6 antibody encompass neutralizing antibodies.

Such an HHV-6 infection inhibitor can be administered in any form that can restrict infection of cells in olfactory epithelium with HHV-6. For example, subcutaneous injection of an HHV-6 vaccine stimulates immunity. This causes an increase in anti-HHV-6 antibody, and therefore restricts infection with HHV-6. The HHV-6 infection inhibitor is preferably administered to, although not limited to, the olfactory epithelium. In actual treatment, any of these HHV-6 infection inhibitors can be administered to the olfactory epithelium by, for example, spraying a proper amount of the HHV-6 infection inhibitor into the nasal cavity.

Therefore, an aspect of the present invention can be a method of treating a mood disorder, the method being characterized by restricting infection of cells in olfactory epithelium of a subject with HHV-6 by increasing the amount of anti-HHV-6 antibody in the subject. This treatment method encompasses both of the following aspects: an aspect of directly administering the anti-HHV-6 antibody to the cells in the olfactory epithelium of the subject; and an aspect of indirectly increasing the anti-HHV-6 antibody by administering an HHV-6 vaccine.

The HHV-6 vaccine used in an embodiment of the present invention is preferably an inactivated vaccine or an attenuated vaccine, and more preferably an inactivated vaccine. An inactivated HHV-6 vaccine can be prepared by causing a virus to lose its replication capacity through a known virus inactivation treatment, examples of which encompass (i) a chemical treatment with use of formalin and (ii) physical treatments such as those with use of heat and radiation. It is possible to add an adjuvant to the HHV-6 vaccine as needed. A person skilled in the art can use a known adjuvant selected as appropriate. Preferable examples of the adjuvant encompass, but are not limited to, aluminum salt adjuvants (such as aluminum hydroxide and aluminum phosphate), emulsifier adjuvants (such as CFA, IFA, squalene, and MF59), polymer fine particle adjuvants (such as liposome and biopolymer), Toll-like receptors (such as dsRNA, CpG-oligo DNA, LPS, and β-glucan), and inositol pentaphosphate (WO2014/065229).

Note that an adjuvant such as inositol pentaphosphate can be sprayed by itself into the nasal cavity without a vaccine. This causes immunity to be activated, and therefore causes an anti-HHV-6 antibody existing in the nasal cavity to be produced by a greater amount. This allows restriction of infection with HHV-6.

Note that the vaccine used in an embodiment of the present invention is, although not limited to, preferably a nasal vaccine. In a case where the HHV-6 vaccine is sprayed into a nasal mucosa so that mainly an anti-HHV-6 IgA antibody is produced in a nasal discharge, it is possible to restrict invasion of HHV-6 from the nasal cavity into the brain.

In a case where the nasal vaccine is used, it is possible to use as needed a substance for increasing adherence in the nasal cavity, such as a gelatinizer and a thickener. Note that there is a technology developed such that in a case where a nasal vaccine is used, the vaccine is contained in cationic nanoparticles so as to induce a systemic immune response and a mucosal immune response without the use of an adjuvant (Japanese Patent No. 5344558). There is also a technology developed such that in a case where an inactivated viral particle antigen is to be transmucosally administered, penetratin or altered peptides of penetratin is/are transnasally administered so as to efficiently induce immunity against the virus (Japanese Patent Application Publication, No. 2012-219041). Such technologies can be used in an embodiment of the present invention. Alternatively, according to an embodiment of the present invention, interfering RNA capable of restricting expression of SITH-1 in cells in olfactory epithelium, such as siRNA and/or miRNA, can be used as a mood disorder treatment agent. Such interfering RNA can be easily made by a person skilled in the art in view of a nucleotide sequence of the SITH-1 gene and in view of known techniques. Then, a treatment agent containing such interfering RNA is sprayed onto the olfactory epithelium so that the interfering RNA is expressed in the cells in the olfactory epithelium. This makes it possible to treat a mood disorder. Such a method of treating a mood disorder with use of interfering RNA is also an aspect of the present invention.

[4] Subject to be Treated by Treatment Method in Accordance with Embodiment of Present Invention Examples of a subject to be treated by the treatment method in accordance with an embodiment of the present invention encompass a subject having a high anti-SITH-1 antibody level in a biological sample. Such a subject can be a subject who has not yet received a diagnosis of a mood disorder. Preferable examples of the subject in accordance with an embodiment of the present invention encompass a patient who (i) has a high anti-SITH-1 antibody level in a biological sample and (ii) has been diagnosed with a mood disorder on the basis of the DSM or the ICD (such a patient will be hereinafter referred to as "mood disorder patient").

Preferable examples of the subject to be treated by the treatment method in accordance with an embodiment of the present invention encompass, but are not limited to, a subject having a high anti-SITH-1 antibody level. More preferable examples of the subject encompass, but are not limited to, a subject who has been found positive for a mood disorder by use of the mood disorder diagnosing method in accordance with an embodiment of the present invention. A subject having a high anti-SITH-1 antibody level is highly likely to have had an onset of a mood disorder as can be explained by the action mechanism described above. A subject who has been found positive by use of the mood disorder diagnosing method in accordance with an embodiment of the present invention is even more likely to have had an onset of a mood disorder. In a case where the treatment method in accordance with an embodiment of the present invention is carried out, it is possible to prevent cells in olfactory epithelium of such a subject from being frequently infected with HHV-6. This makes it possible to restrict an onset of a symptom or deterioration of the symptom.

Immunocompetence against viruses considerably varies depending on genetic factors of individuals. It is clear that subjects each having low immunocompetence against HHV-6, that is, subjects whose biological samples separated therefrom are measured and found to have low anti-HHV-6 antibody levels are at a high risk of a mood disorder because of HHV-6 as can be explained by the action mechanism, even in a case where the subjects have not had an onset of the mood disorder. Example 3.1 suggests that in a case where the amount of anti-HHV-6 antibody in serum is small, the subject is exposed to HHV-6, so that the amount of SITH-1 expressed in a host cell becomes large. Therefore, such subjects are preferable as subjects to be treated by the treatment method (prevention method). In addition, it is also an aspect of the present invention to measure the amount of anti-HHV-6 antibody in order to determine whether or not a subject is at a high risk of a mood disorder.

It is known that in a case where a fatigue level of a human increases, HHV-6, which is latently infecting the human, is reactivated and released into saliva (Japanese Patent No. 4218842). This increases the risk of the olfactory epithelium being exposed to HHV-6. In general, an increase in reactivated viruses leads to an increase in antibodies against the viruses. Surprisingly, however, it was confirmed as described above that amounts of HHV-6 in specimens of mood disorder patients found positive for anti-SITH-1 antibody, although anti-HHV-6 antibody levels of the specimens of such patients are low, are significantly larger than those of mood disorder patients found negative for anti-SITH-1 antibody (see FIG. 25). This can be explained for the first time with the action mechanism described above. The action mechanism is therefore confirmed. This finding clearly shows that a subject, who is found positive for an anti-SITH-1 antibody and whose biological sample separated from the subject is measured and found to contain a large amount of HHV-6, is an effective subject to be treated by the treatment method in which the HHV-6 infection inhibitor in accordance with an embodiment of the present invention is used.

Furthermore, in a case where a biological sample separated from a subject is measured and found to contain a low anti-HHV-6 antibody level and is found to contain a large amount of HHV-6, the subject is clearly at a high risk of a mood disorder because of HHV-6 as can be explained by the action mechanism even if the subject has not had an onset of the mood disorder. The subject is therefore preferable as a subject to be treated by the treatment method (prevention method) described above.

An amount of HHV-6 in a biological sample can be measured by a conventionally well-known method which can be selected as appropriate by a person skilled in the art. Examples of the method encompass a method in which viral nucleic acids are measured and a method in which viral proteins are measured (Japanese Patent No. 4218842).

[5] Mood disorder treatment agent, mood disorder treatment method, transformed cell, mood disorder model animal and the like Bcl-2 (B cell lymphoma-2) family proteins play a central role in controlling apoptosis. Bcl-2 family proteins are divided into (i) apoptosis promoting factors such as Bax and Bid and (ii) apoptosis inhibiting factors such as Bcl-2 and Bcl-XL. Whether or not apoptosis occurs is determined by a balance between the apoptosis promoting factors and the apoptosis inhibiting factors in cells (see Literature 12). Meanwhile, mood stabilizers and mood disorder treatment agents (examples of the mood disorder treatment agents encompass amitriptyline, desipramine, imipramine, fluoxetine, reboxetine, tranylcypromine, venlafaxine, and salts of these) are known to promote Bcl-2 expression in the brain (see Literatures 13 through 16). It is also suggested that administration of an antagonist against an apoptosis promoting factor Bid (BO-11A7, BI-2A7) restricts mental disorder-like behavioral abnormalities of a mouse (see Literature 17).

In view of these facts, the action mechanism of a mood disorder found by the inventors of the present invention is considered. In particular, the fact that SITH-1 expression in cells in olfactory epithelium restricts expression of the apoptosis inhibiting factor Bcl-2 is considered. It is then clear that the above drugs and the antagonist against Bid can each be used as a treatment agent for a mood disorder that derives from SITH-1 expression, because (i) the above drugs promote Bcl-2 expression and (ii) the antagonist against Bid restricts Bid expression.

Note that while such an antagonist against Bid can be a known antagonist (US20100261788, U.S. Pat. No. 7,741,521, WO2006004622), the antagonist is preferably BO-11A7 or BI-2A7, and more preferably BO-11A7.

That is, an aspect of the present invention is a method of treating a mood disorder, the method being characterized by administering, to a subject having a high anti-SITH-1 antibody level or a subject found positive for a mood disorder by use of the mood disorder diagnosing method in accordance with an embodiment of the present invention, any one of the following: (i) a mood disorder treatment agent selected from amitriptyline, desipramine, imipramine, fluoxetine, reboxetine, tranylcypromine, venlafaxine, and salts of these; (ii) a mood stabilizer; and (iii) an antagonist against Bid.

An embodiment of the present invention also provides an impairment treatment agent (or alternatively a prophylactic) containing an HHV-6 infection inhibitor.

An embodiment of the present invention further includes use of an HHV-6 infection inhibitor for a treatment (or alternatively prevention) of the impairment.

An embodiment of the present invention provides transformed cells characterized in that the transformed cells are obtained by a transfecting SITH-1 gene(s) into cells in olfactory epithelium. The cells in the olfactory epithelium are preferably human cells in olfactory epithelium. By using such a cell, it is made possible to carry out screening for a substance that restricts an incorrect signal which occurs as a result of SITH-1 gene expression in cells in olfactory epithelium.

Examples of the incorrect signal encompass, but are not limited to, expression abnormalities of a GABA transporter, a GABA receptor, an olfactory receptor, an adrenergic receptor, a glutamic acid transporter, and a glutamic acid receptor. It is therefore possible to carry out, while all or part of expression levels in cells in olfactory epithelium is used as an index, screening for a substance that restricts an incorrect signal to an olfactory cell.

An embodiment of the present invention further provides a model animal for the impairment, the model animal being obtained by transfecting SITH-1 gene(s) into cells in olfactory epithelium.

Examples of the SITH-1 gene to be transfected into the cells in the olfactory epithelium encompass polynucleotide that encodes a SITH-1 protein (hereinafter also referred to as "protein (a)") and which is represented by SEQ ID NO. 2. Examples of the SITH-1 gene also encompass a gene that encodes a protein which (i) has an amino acid sequence represented by SEQ ID NO. 1 in which amino acid sequence one or several amino acids are substituted, deleted, inserted and/or added and (ii) induces, if transfected into cells in olfactory epithelium, apoptosis of the olfactory cell (such a protein will be hereinafter also referred to as "protein (b)").

The phrase "one or several amino acids are substituted, deleted, inserted and/or added" means a substitution, deletion, insertion, and/or addition of such a number of amino acids (preferably 10 or less, more preferably 7 or less, even more preferably 5 or less) that can be substituted, deleted, inserted, and/or added by a well-known method for preparation of a mutant peptide, such as site-directed mutagenesis. It can be said that the protein (b) is thus a mutant protein of the protein (a). Note that "mutant" defined herein mainly means a mutant artificially introduced by a known method of preparing a mutant protein. Alternatively, "mutant" can be a mutant obtained by isolating and purifying a naturally-occurring mutant protein similar to the artificial mutant protein.

Examples of an alternative SITH-1 gene to be transfected into cells in olfactory epithelium encompass a gene that encodes a protein which (i) has an amino acid sequence having an amino acid identity with the amino acid sequence represented by SEQ ID NO. 1, the amino acid identity being of at least equal to or greater than 80%, preferably equal to or greater than 85%, equal to or greater than 90%, equal to or greater than 93%, equal to or greater than 94%, equal to or greater than 95%, equal to or greater than 96%, equal to or greater than 97%, equal to or greater than 98%, or equal to or greater than 99%, and more preferably 99.5% and (ii) induces, if transfected into cells in olfactory epithelium, apoptosis of the olfactory cell (such a protein will be hereinafter also referred to as "protein (c)").

The identity percentage of the amino acid sequences can be determined by visual examination and mathematical calculation. Alternatively, the identity percentage of the amino acid sequences can be determined by comparing sequence information by use of the GAP computer program, based on the algorithm of Needleman, S. B. and Wunsch, C. D. (J. Mol. Biol., 48: 443-453, 1970). The GAP computer program is available from the University of Wisconsin Genetics Computer Group (UWGCG). Preferable examples of default parameters of the GAP program encompass: (1) the scoring matrix, BLOSUM62 as disclosed in Henikoff, S. and Henikoff, J. G. (Proc. Natl. Acad. Sci. USA, 89: 10915-10919, 1992); (2) addition of 12 gaps; (3) addition of 4 gap lengths; and (4) no terminal gap penalty.

Alternatively, it is possible to use another sequence comparison program used by persons skilled in the art. The identity percentage of the amino acid sequences can be determined by comparing sequence information by use of, for example, the BLAST program disclosed in Altschul et al. (Nucl. Acids. Res., 25, p. 3389-3402, 1997). The program can be used on the website of the National Center for Biotechnology Information (NCBI) or on the website of the DNA Data Bank of Japan (DDBJ). Various conditions (parameters) for a sequence identity search with use of the BLAST program are disclosed in detail in the above websites, and part of the setting can be changed as needed. Note, however, that a search is ordinarily carried out with use of default values. Alternatively, the identity percentage of the amino acid sequences can be determined by use of (i) a program such as the genetic information processing software GENETYX Ver.7 (produced by GENETYX CORPORATION) or (ii) the FASTA algorithm. In so doing, a search can be carried out with use of default values.

The protein having an amino acid sequence represented by SEQ ID NO. 1 is isolated and identified as a protein that is specifically expressed during latent infection with human herpesvirus-6 (HHV-6), and will be hereinafter referred to as "SITH-1 protein". The SITH-1 protein has an amino acid sequence represented by SEQ ID NO. 1, and is a protein which consists of 159 amino acids and which has a molecular weight of approximately 17.5 kDa. The SITH-1 protein is encoded by a SITH-1 gene. cDNA of the SITH-1 gene has a size of 1795 base pairs (approximately 1.79 kbp) as shown in SEQ ID NO. 3. A start codon (Kozak ATG) of the cDNA of the SITH-1 gene is a sequence of 954th to 956th nucleotides. A stop codon (TAA) of the cDNA of the SITH-1 gene is a sequence of 1431st to 1433rd nucleotides. Therefore, the SITH-1 gene has, as an open reading frame (ORF) region, a sequence of 954th through 1430th nucleotides of the nucleotide sequence shown in SEQ ID NO. 3. The ORF has a size of 477 base pairs (approximately 0.48 kbp). Of the cDNA of the SITH-1, a nucleotide sequence representing the ORF region is shown in SEQ ID NO. 2. Note that the nucleotide sequence shown in SEQ ID NO. 2 includes the three nucleotides of the stop codon.

Examples of the SITH-1 gene to be transfected further encompass a gene that (i) hybridizes, under stringent hybridization conditions, with a DNA having a nucleotide sequence complementary to a DNA having a nucleotide sequence represented by SEQ ID NO. 2 and (ii) encodes a protein which induces, if transfected into cells in olfactory epithelium, apoptosis of the olfactory cell.

The phrase "hybridizes under stringent hybridization conditions" means that hybridization occurs only if sequences have an identity of at least 90%, preferably an identity of at least 95%, and most preferably an identity of at least 97%.

More specific examples of the "stringent hybridization conditions" encompass conditions where polynucleotides are incubated in a hybridization solution (50% formamide, 5×SSC (150 mM NaCl, 15 mM trisodium citrate), 50 mM sodium phosphate (pH 7.6), 5×Denhart's solution, 10% dextran sulfate, and 20 µg/ml of sheared denatured salmon sperm DNA) overnight at 42° C., and then the filter is washed with 0.1×SSC at approximately 65° C. The hybridization can be carried out by a conventionally well-known method such as the method disclosed in Literature 10 (described later), and is not limited to any particular one. Ordinarily, stringency increases (hybridization becomes difficult) at a higher temperature and at a lower salt concentration.

Note that the term "gene" as used herein is interchangeable with "polynucleotide", "nucleic acid", or "nucleic acid molecule". "Polynucleotide" means a polymer of nucleotides.

Therefore, the term "gene" used herein encompasses not only double stranded DNA but also (i) single stranded DNA, such as a sense strand and an antisense strand, by which double stranded DNA is constituted and (ii) RNA (such as mRNA). An antisense strand can be used as a probe or as an antisense drug.

Examples of the "DNA" encompass cDNA and genomic DNA each of which is obtained by cloning, a chemical synthesis technique, or a combination of cloning and a chemical synthesis technique. That is, the DNA can be (i) "genome" formed DNA that includes a non-coding sequence such as an intron in the form included in the genome of an animal or (ii) cDNA that can be obtained based on mRNA by use of a reverse transcriptase and a polymerase, that is, "transcription" formed DNA that includes no non-coding sequence such as an intron.

A gene in accordance with an embodiment of the present invention can have, other than a sequence that encodes an amino acid described in the above (a), (b), or (c), a sequence such as a sequence of an untranslated region (UTR) or a vector sequence (including an expression vector sequence). Alternatively, any polynucleotides such as a regulatory sequence or a polyadenyl sequence can be included at the end and/or inside of a translated region of mRNA or cDNA of the above (a), (b), or (c). In a case where a protein in accordance with an embodiment of the present invention is to be encoded by a plurality of allelic genes, a nucleic acid in accordance with an embodiment of the present invention encompasses all of allelic genes, transcripts of the allelic genes, and cDNA.

Note that the term "nucleic acid" herein encompasses polynucleotide composed of any simple nucleotides and/or modified nucleotides. Examples of the nucleic acid encompass cDNA, mRNA, total RNA, and hnRNA. Examples of "modified nucleotide" encompass (i) phosphate esters including inosine, acetylcytidine, methylcytidine, methyladenosine, and methylguanosine and (ii) acquired nucleotide which can occur by the effect of an ultraviolet ray or a chemical substance.

The term "nucleotide sequence" is interchangeable with "nucleic acid sequence", and is represented as a sequence of deoxyribonucleotide (which is abbreviated as A, G, C, and T). A polynucleotide or a "nucleotide sequence" of a polynucleotide means (i) a sequence of deoxyribonucleotides with respect to a DNA molecule or the polynucleotide and (ii) a sequence corresponding to ribonucleotides (A, G, C, and U) with respect to an RNA molecule or the polynucleotide (Note that each of thymidine deoxynucleotides (T) defined in a deoxynucleotide sequence is substituted by a uridine (U) of the ribonucleotides.).

For example, an "RNA molecule having a sequence represented by SEQ ID NO. 2 or 3" shown by use of an abbreviation of deoxyribonucleotide means an RNA molecule having a sequence in which a deoxynucleotide A, G, or C in SEQ ID NO. 2 or 3 is substituted by a ribonucleotide A, G, or C, respectively, and in which a deoxynucleotide T is substituted by a ribonucleotide U. A "polynucleotide or its fragment having a nucleotide sequence represented by SEQ ID NO. 2 or 3" means a polynucleotide or its fragment having a sequence represented by a deoxynucleotide A, G, C, and/or T in SEQ ID NO. 2 or 3.

A method of transfecting the SITH-1 gene into cells in olfactory epithelium can be a conventionally well-known method. Examples of the method encompass, but are not limited to, (i) a method in which an adenovirus vector is used, (ii) a method in which a retrovirus vector is used, and (iii) a method in which transfection of a gene is employed. Alternatively, typical gene transfection by use of a transgene can be employed (preparation of a transgenic mouse).

Animals to be the subjects into which the SITH-1 gene is transfected are not limited to any particular ones, provided that the animals can be used as laboratory animals. The animals are preferably mammals. Examples of the animals encompass mice, rats, and monkeys. A model animal in accordance with an embodiment of the present invention can be suitably used for, for example, (i) study of the mood disorder treatment methods, (ii) study and evaluation of effects of drugs, and (iii) evaluation of methods of treating (e.g. thermotherapy) a mood disorder other than methods in which drugs are used. The model animal in accordance with an embodiment of the present invention, in particular, thus shows that Bcl-2 expression is restricted as described above. It can be said that an animal modified in such a manner has a remarkably excellent characteristic as a model animal for a mood disorder in view of the fact that it is suggested that restriction of Bcl-2 expression is closely associated with mental disorder-like behavioral abnormalities (see Literature 17).

[6] Screening Method of Screening for Candidate Substance for Mood Disorder Treatment Agent The impairment model animal in accordance with an embodiment of the present invention can be further used for a method of screening for a candidate substance for the impairment treatment agent, preferably a mood disorder treatment agent. Specifically, in a case where a candidate substance for the impairment treatment agent is administered to a model animal in accordance with an embodiment of the present invention and then a well-known behavioral abnormality test such as a startle response test, a tail suspension test, a locomotion activity test, or a stress vulnerability test shows an improvement in abnormal behavior, it can be determined that the candidate substance has an effect of improving a mood disorder and/or stress vulnerability.

In a case where a candidate substance for the impairment treatment agent is administered to the model animal in accordance with an embodiment of the present invention and then detection and measurement of a biomarker in the brain of the model animal shows an improvement in abnormalities, it can be determined that the candidate substance has an anti-impairment effect. Examples of such a biomarker encompass (i) markers for detecting apoptosis in an olfactory bulb, (ii) markers for detecting abnormalities of the hypothalamus, and (iii) stress response factors in a brain. Examples of a marker for detecting apoptosis in an olfactory bulb encompass, but are not limited to, Bcl-2. Examples of a marker for detecting abnormalities of the hypothalamus encompass, but are not limited to, CRH and urocortin. Examples of a stress response factor in a brain encompass, but are not limited to, REDD1.

As described above, the model animal in accordance with an embodiment of the present invention has abnormalities such as a decreased amount of Bcl-2, an increased amount of CRH, an increased amount of urocortin, and an increased amount of REDD1 expression, in comparison with a healthy animal. This allows screening for a candidate substance for a treatment agent to be carried out while an improvement in at least one of these abnormalities serving as an index. Furthermore, screening by the behavioral abnormality test and screening by detection of the biomarker can be used in combination as needed.

Therefore, the following mood disorder screening method is an aspect of the present invention. That is, the mood disorder screening method characterized in that in a case where a test substance is administered to the model animal in accordance with an embodiment of the present invention and then detection and/or measurement of at least one of the biomarkers in the brain of the model animal shows an improvement in abnormalities, it is determined that the test substance is a candidate substance for a mood disorder treatment agent.

The present invention is not limited to the embodiments, but can be altered by a skilled person in the art within the scope of the claims. An embodiment derived from a proper combination of technical means each disclosed in a different embodiment is also encompassed in the technical scope of the present invention. Further, it is possible to form a new technical feature by combining the technical means disclosed in the respective embodiments. The following description will discuss an embodiment of the present invention in detail Examples. Note, however, the present invention is not limited only to these Examples.

Examples (1) Preparation of SITH-1-Expressing Adenovirus

A recombinant adenovirus was constructed as a virus that infects a model animal and expresses a SITH-1. The recombinant adenovirus was constructed in accordance with the standard protocol an Adenovirus Expression Vector Kit (Takara bio).

A pGfa2Lac plasmid containing a glial fibrillary acidic protein (GFAP) promoter was provided by Dr. Kazuyoshi Ikuta (originally produced by Dr. Michael Brenner).

A GFAP promoter obtained from the pGfa2Lac plasmid and the SITH-1 gene amplified by PCR were cloned into an adenovirus cosmid vector by use of a standard method (Ad-GFAP-SITH-1). HEK293 cells were transfected with (i) the Ad-GFAP-SITH-1 cosmid vector or (ii) a cosmid vector (pAxcwit) which serves as a control and into which the target gene was not inserted.

The HEK293 cells were cultured in Dulbecco's modified Eagle's medium (DMEM) containing 10% fetal bovine serum. The recombinant adenovirus was prepared in 293 cells and purified with use of an Adeno-X Virus Purification kits (Clontech). The titer of the virus thus purified was determined by use of an Adeno-X rapid titer kits (Clontech).

(2) Mice to which SITH-1-Expressing Adenovirus was Nasally Administered

For the purpose of analyzing behaviors and gene expression level changes when SITH-1 is expressed in cells in olfactory epithelium, the SITH-1-expressing adenovirus (SITH-1/Adv) was administered into nasal cavities of mice.

Cosmid vector-derived adenovirus (empty/Adv) into which no SITH-1 gene was inserted was used as a control.

(2.1) Nasal Administration of SITH-1-Expressing Adenovirus 8-week-old C57BL/6NCrSlc mice were raised at a room temperature of 24±1° C. and with lights on for 12 hours and off for 12 hours. After each of the mice was anesthetized with use of isoflurane, SITH-1/Adv or empty/Adv in an amount equivalent to $2.5 \times 10^7$ ifu was dropped onto the nasal cavity, and was then sucked along with breathing. Then, the mice were returned to raising cages.

(2.2) Tail Suspension Test of Mice to which SITH-1-Expressing Adenovirus was Nasally Administered 7 days after the nasal administration of SITH-1/Adv or empty/Adv, a tail suspension test was carried out for 10 minutes. A period of immobility time was measured with use of TailSuspScanTopScan (CleverSys, Inc.). The tail suspension test was carried out by suspending each mouse by taping the tail 1 cm from the end. The mouse was considered immobile if it was passive and did not move at all during suspension. In the experiment, 30 mice were used in each group.

(A) of FIG. 1 shows the results of comparison between (i) periods of immobility time of the mice into which empty/Adv was nasally administered (hereinafter referred to as "empty/Adv nasal administration mice") and (ii) periods of immobility time of the mice into which SITH-1/Adv was nasally administered (hereinafter referred to as "SITH-1/Adv nasal administration mice"). Statistical significance (* indicates $P<0.05$,  indicates $P<0.01$, and * indicates $P<0.001$) was calculated by use of the Mann-Whitney U-test.

(A) of FIG. 1 shows that the periods of immobility time of the SITH-1/Adv nasal administration mice were significantly increased in comparison with those of the empty/Adv nasal administration mice. This clearly demonstrated that the SITH-1/Adv nasal administration mice exhibited depressive disorder-like behaviors.

Then, it was studied whether or not an SSRI (selective serotonin reuptake inhibitor), which is an antidepressant, would restrict an increase in immobility time, the increase being caused by the nasal administration of the SITH-1/Adv. 80 mg/L of Fluoxetine solution as drinking water was given to 6-week-old mice (see Literature 18), and then the mice were raised for 2 weeks. Then, SITH-1/Adv was nasally administered. 7 days after the nasal administration, a tail suspension test was carried out for 10 minutes. After the nasal administration of the SITH-1/Adv, the mice were raised in such a manner as to continue to receive 80 mg/L of Fluoxetine solution. In the experiment, 21 mice were used as an SSRI administered group. (B) of FIG. 1 shows the effect of the SSRI administration on the immobility time. Statistical significance (* indicates $P<0.05$,  indicates $P<0.01$, and * indicates $P<0.001$) was calculated by use of the Mann-Whitney U-test.

(B) of FIG. 1 shows that immobility time increases observed among the SITH-1/Adv nasal administration mice were restricted as a result of SSRI administration, and that a depressive disorder-like behavior caused by nasal administration of SITH-1/Adv can be therefore improved by administration of SSRI. Note that in view of the fact that Fluoxetine promotes Bcl-2 expression (see Literature 13), the results above confirm that a mood disorder treatment agent which promotes Bcl-2 expression can be used as an agent for treating a mood disorder caused by SITH-1 expression.

(2.3) Analysis of Gene Expression of Mice to which SITH-1-Expressing Adenovirus was Nasally Administered For the purpose of studying whether or not nasal administration of SITH-1/Adv would cause a change in gene expression, olfactory bulbs and brains of the empty/Adv nasal administration mice and the SITH-1/Adv nasal administration mice were collected 24 hours after the tail suspension test. RNA of the olfactory bulbs and the brains were purified, and then amounts of mRNA of depressive disorder-related factors and apoptosis-related factors were quantified by use of real-time RT-PCR. A β-actin gene was used as a reference gene.

Figure 2:
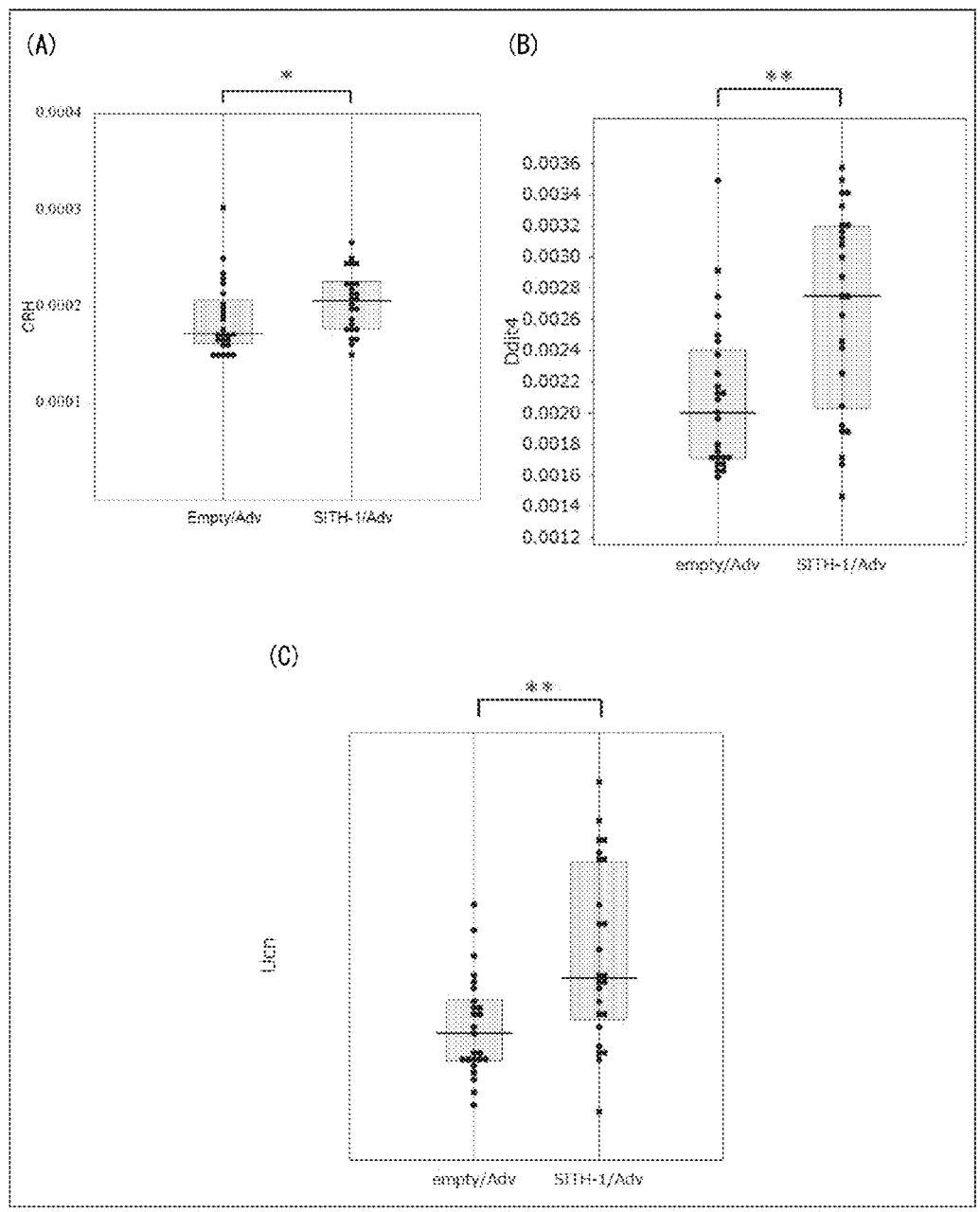
FIG. 2 shows the results of gene expression of depressive disorder-related factors in the brain. (A) of FIG. 2 is a view showing the results of CRH genes. (B) of FIG. 2 is a view showing the results of REDD1 genes. (C) of FIG. 2 is a view showing the results of Urocortin genes.
Figure 3:
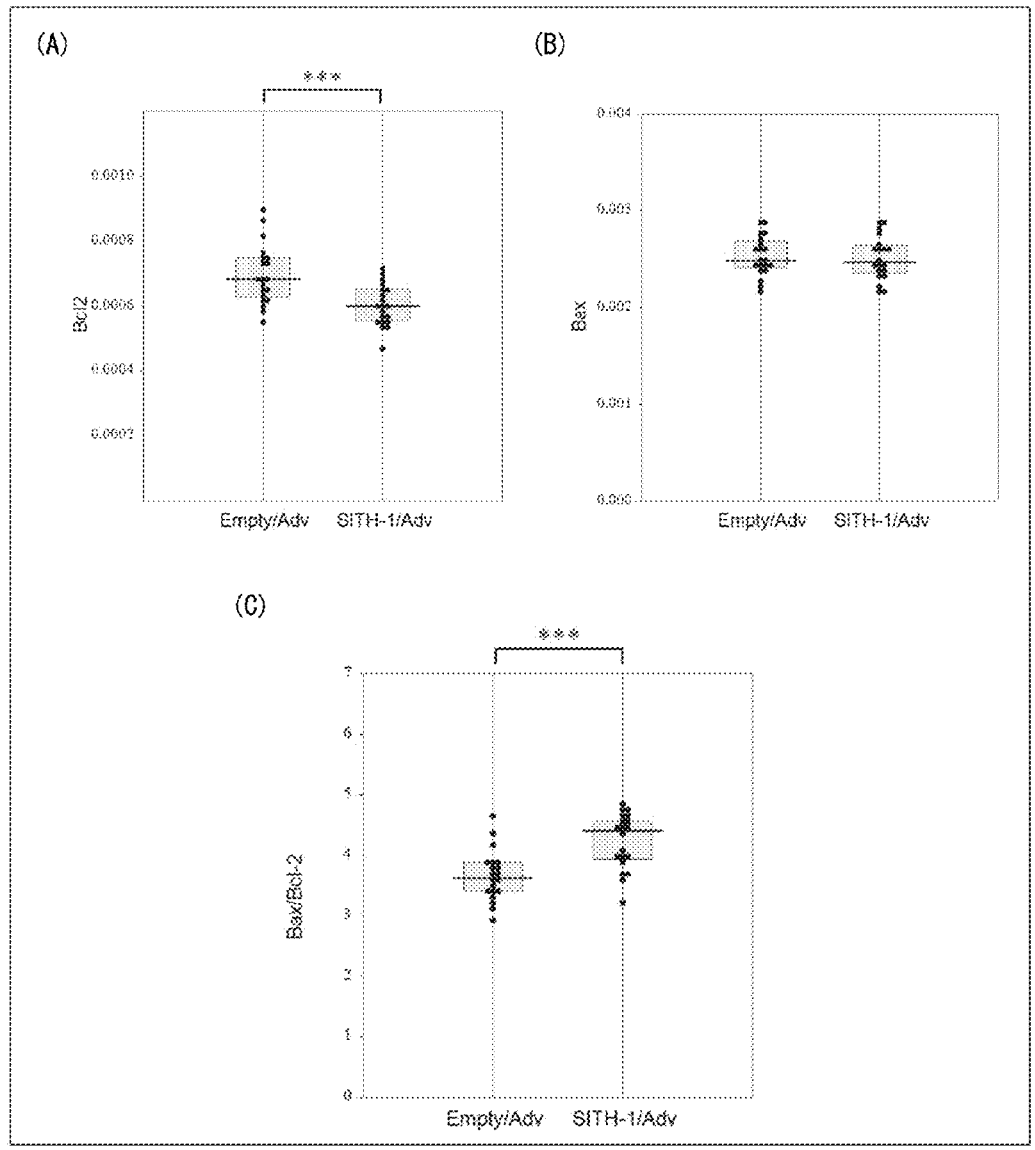
FIG. 3 shows the results of gene expression of apoptosis-related factors in olfactory bulbs. (A) of FIG. 3 is a view showing the results of gene expression of apoptosis inhibiting factors Bcl-2. (B) of FIG. 3 is a view showing the results of gene expression of apoptosis promoting factors Bax. (C) of FIG. 3 is a view showing apoptosis index Bax-to-Bcl-2 ratios.

FIG. 2 shows, as depressive disorder-related factors, expression levels of CRH, REDD1, and Urocortin genes of the whole brains excluding the olfactory bulbs. Note that "Ddit4" in (B) of FIG. 2 is another name for REDD1. FIG. 3 shows (i) expression levels of Bcl-2 of olfactory bulbs, (ii) expression levels of Bax genes of the olfactory bulbs, and (iii) the ratio between the expression levels of the Bcl-2 and of the Bax gene (Bax/Bcl-2). Statistical significance (* indicates $P<0.05$,  indicates $P<0.01$, and * indicates $P<0.001$) was calculated by use of the Mann-Whitney U-test.

In regard to the depressive disorder-related factors, a comparison was made between (i) the expression levels of the genes of the whole brains (excluding the olfactory bulbs) of 25 empty/Adv nasal administration mice and (ii) the expression levels of the genes of the whole brains (excluding the olfactory bulbs) of 25 SITH-1/Adv nasal administration mice. Meanwhile, in regard to the apoptosis-related factors, a comparison was made between (i) the expression levels of apoptosis-related genes of the olfactory bulbs of 20 empty/Adv nasal administration mice and (ii) the expression levels of apoptosis-related genes of the olfactory bulbs of 20 SITH-1/Adv nasal administration mice.

FIG. 2 shows that the expression levels of CRH, REDD1, and Urocortin genes in the whole brains of the SITH-1/Adv nasal administration mice were significantly increased in comparison with those of the empty/Adv nasal administration mice. This clearly demonstrated that, as are the cases of depressive disorder patients, the SITH-1/Adv nasal administration mice exhibit increases in expression of CRH, REDD1, and Urocortin.

FIG. 3 also shows that the expression levels of Bcl-2, which is an apoptosis inhibiting factor, were significantly decreased in the olfactory bulbs of the SITH-1/Adv nasal administration mice in comparison with the empty/Adv nasal administration mice (see (A) of FIG. 3). Meanwhile, there was no significant difference in expression levels of Bax which is an apoptosis promoting factor (see (B) of FIG. 3). Calculation of a Bax-to-Bcl-2 ratio, which serves as an apoptosis index, indicated a significant increase in Bax-to-Bcl-2 ratios in the olfactory bulbs of the SITH-1/Adv nasal administration mice (see (C) of FIG. 3).

Therefore, it is considered that apoptosis is induced in the olfactory bulbs of the SITH-1/Adv nasal administration mice, and that this fact is associated with atrophy of olfactory bulbs of depressive disorder patients observed.

(2.4) Immunohistological Staining of Mice to which SITH-1-Expressing Adenovirus was Nasally Administered 24 hours after the tail suspension test, the empty/Adv nasal administration mice and the SITH-1/Adv nasal administration mice were each fixed in a 10% neutral buffered formalin solution, and then a paraffin section of a maxillary part of the cranial bones was prepared.

(2.4.1) TUNEL Staining of Paraffin Section of Maxillary Part of Cranial Bone of Mice TUNEL staining of paraffin section slides were carried out in accordance with the standard protocol of an In situ Apoptosis Detection Kit (TaKaRa Bio). For counter staining of nuclei, a mounting agent containing PI, VECTASHIELD Mounting Medium with PI (VECTOR Laboratories), was used.

Figure 4:
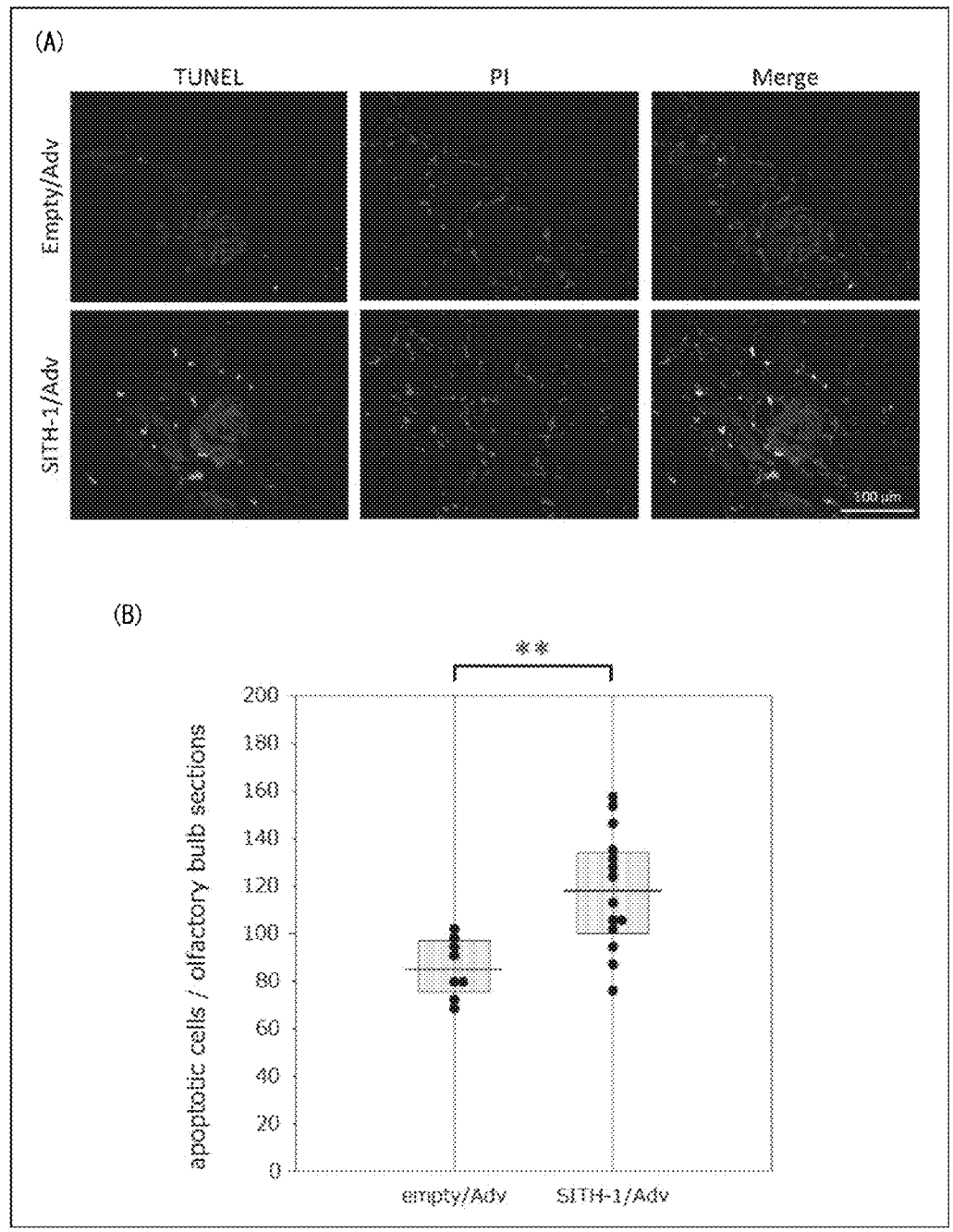
FIG. 4 shows the results of TUNEL staining of olfactory bulbs. (A) of FIG. 4 is a view showing TUNEL stained images of olfactory bulbs of empty/Adv nasal administration mice and SITH-1/Adv nasal administration mice. (B) of FIG. 4 is a view showing the results of counting the number of cells positive for TUNEL staining of olfactory bulbs.

(A) of FIG. 4 shows the results of observation by use of a fluorescence microscope. (B) of FIG. 4 shows the results of counting the number of cells present in the olfactory bulbs and stained by TUNEL staining. As shown in (A) of FIG. 4, genomes fragmented by apoptosis were stained green by TUNEL staining, and the nuclei of the cells were stained red by PI. In (B) of FIG. 4, Statistical significance (* indicates P<0.05,  indicates P<0.01, and * indicates P<0.001) was calculated by use of the Mann-Whitney U-test. In comparison with the empty/Adv nasal administration mice, a large number of cells stained by TUNEL staining were observed in the olfactory bulbs of the SITH-1/Adv nasal administration mice. This is consistent with the results of the gene expression analysis, and therefore demonstrated that nasal administration of SITH-1/Adv induces apoptosis in an olfactory bulb.

(2.4.2) SITH-1 Expression in Cells in Olfactory Epithelium of Mice

For the purpose of confirming SITH-1 protein expression in cells in olfactory epithelium as a result of nasal administration of SITH-1/Adv, immunohistological staining of paraffin sections were carried out. After the paraffin section slides were deparaffinized, the paraffin section slides were immersed in a Tris-EDTA Buffer (100 mM Tris, 10 mM EDTA, 0.5% Tween 20, pH 9.0) at 98° C. for 20 minutes so that antigens were activated. Then, an Image-iT (trademark) FX Signal Enhancer (Life technologies) was dropped on each of the activated slides. Then, the slides were allowed to stand at room temperature for 30 minutes so that blocking reactions were made.

A solution was obtained by 100-fold dilution of a rabbit anti-SITH-1 antibody and a mouse anti-GFAP antibody (Abcam) with use of a Can Get Signal immunostain Solution A (TOYOBO). Then, the solution was dropped on the slides. Then, the slides were allowed to stand overnight at 4° C. After reactions, the glass slides were washed 3 times with use of a 0.2% Tween 20/PBS solution.

Solutions were obtained by 250-fold dilution and 400-fold dilution of Alexa Fluor 488 goat anti-rabbit IgG(H+L) (invitrogen) and of Alexa Fluor 594 goat anti-mice IgG(H+L) (invitrogen), respectively, with use of a Can Get Signal immunostain Solution A. Then, the solutions were dropped on the slides. Then, the slides were allowed to stand at 37° C. for 1 hour.

Figure 5:
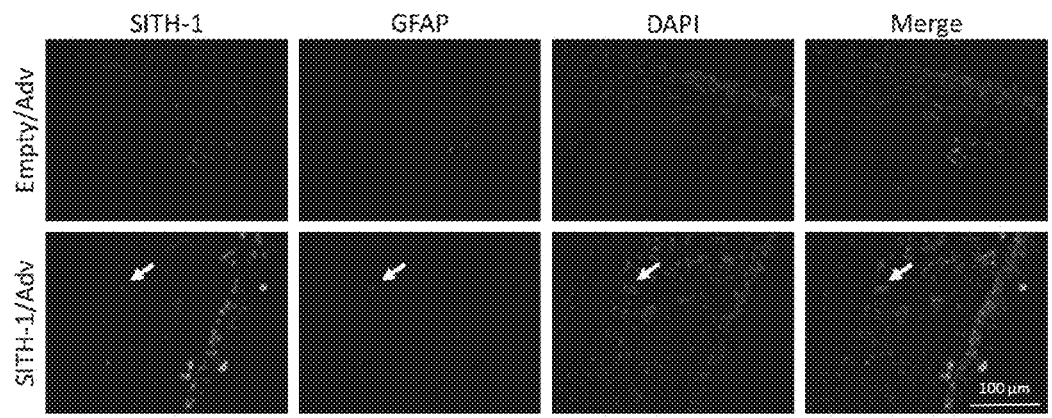
FIG. 5 shows the results of immunohistological staining of olfactory epithelia by anti-SITH-1 antibodies, and is a view showing immunohistologically stained images of cells in olfactory epithelium of empty/Adv nasal administration mice and SITH-1/Adv nasal administration mice.

After reactions, the glass slides were washed 3 times with use of a 0.2% Tween 20/PBS solution, and were then dried. Then, a cover glass was fixed with use of a mounting agent, ProLong Gold Antifade Reagent with DAPI (Life technologies). FIG. 5 shows the results of the observation with use of a fluorescence microscope.

In FIG. 5, the cells indicated by arrows are astrocytes in which SITH-1 protein expression were observed. In FIG. 5, cells stained by both an anti-SITH-1 antibody and an anti-GFAP antibody were observed only in cells in olfactory epithelium of the SITH-1/Adv nasal administration mice. This confirmed that the nasal administration of SITH-1/Adv causes SITH-1 protein expression in the cells in olfactory the epithelium cells of the mice.

(2.5) Stress Vulnerability Test of Mice to which SITH-1-Expressing Adenovirus was Nasally Administered For the purpose of studying a possibility that nasal administration of SITH-1/Adv causes mice to be hypersensitive and more vulnerable to stress, stress vulnerability was studied.

8-week-old mice were each raised in isolation. Then, from 3 days before administration of SITH-1/Adv, the mice were given water and a 1% sucrose solution each as drinking water such that the two kinds of drinks were equilibrated in terms of ratio. 3 days later, SITH-1/Adv was nasally administered. Then, half of the mice were each raised in a cage that was slanted by 20 degrees. The amount of drinks consumed by the mice was recorded every 24 hours.

Figure 6:
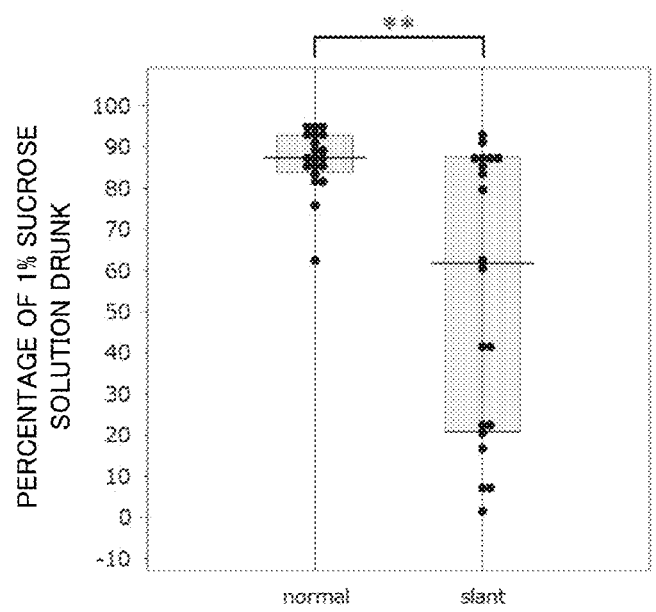
FIG. 6 shows the results of a stress vulnerability test of SITH-1/Adv nasal administration mice.

FIG. 6 shows percentages of 1% sucrose solution drunk (amount of 1% sucrose solution drunk/amount of all drinks (amount of water drunk+amount of 1% sucrose solution drunk)) by the mice raised in isolated horizontal raising cages (normal: n=20) and by the mice raised in the isolated cages slanted by 20 degrees (slant: n=20) 7 days after the nasal administration of SITH-1/Adv. Statistical significance (* indicates P<0.05,  indicates P<0.01, and * indicates P<0.001) was calculated by use of the Mann-Whitney U-test.

FIG. 6 shows that applying a mild level of stress by slanting a cage caused the SITH-1/Adv nasal administration mice to have less preference for sucrose. It is therefore considered that the SITH-1/Adv nasal administration mice became hypersensitive to mild stress and therefore caused the SITH-1/Adv nasal administration mice to exhibit a "loss of pleasure" behavior which is observed among depressive disorder patients. This indicates that SITH-1 protein expression in the olfactory epithelium astrocytes induces stress vulnerability.

(3) Restriction of SITH-1 Expression by HHV-6 Infection Inhibitor

It was examined whether or not an HHV-6 infection inhibitor would restrict SITH-1 expression in HHV-6 host cells.

(3.1) Restriction of SITH-1 Expression by HHV-6 Neutralizing Antibody

An experiment was conducted by use of an HHV-6 neutralizing antibody serving as an HHV-6 infection inhibitor. As a neutralizing antibody, an anti-HHV-6B p98 (gH) monoclonal antibody was used. Since serum of a healthy individual also contains an anti-HHV-6 antibody, a 10-fold dilution series was prepared and used in the experiment.

Serum of healthy individuals was allowed to stand at 56° C. for 30 minutes (inactivation). The following mixtures were prepared in equal amounts: (i) mixtures of HHV-6 HST strain virus fluid ($2.9 \times 10^6$ ffu/ml) and inactivated serum of healthy individuals (no dilution, 10-fold dilution in a medium (10% FBS-containing DMEM), and 100-fold dilution in a medium (10% FBS-containing DMEM)), (ii) mixtures of HHV-6 HST strain virus fluid ($2.9 \times 10^6$ ffu/ml) and anti-HHV-6B p98 (gH) monoclonal antibody (Clone: OHV-3) (10-fold dilution in a medium), and (iii) mixtures, serving as controls, of HHV-6 HST strain virus fluid ($2.9 \times 10^6$ ffu/ml) and a medium by itself. These mixtures were reacted at 37° C. for 1 hour.

Then, the virus fluid thus processed was used to infect, by centrifugation, U373 astrocytoma cells at a multiplicity of infection (MOI) (which is the number of viruses per cell) of 3. Then, the infected cells were cultured at 37° C. for 48 hours in a $CO_2$ incubator. From the resultant infected cells, RNA was purified by use of RNeasy Mini Kit (Qiagen) in accordance with the standard protocol. Then, cDNA was synthesized by use of a PrimeScript RT Reagent Kit (Takara Bio).

Finally, expression levels of SITH-1 and GAPDH mRNA were measured by use of an Applied Biosystems 7300 Real-Time PCR system (Life Technologies). The measurement was carried out twice under the following conditions. Conditions of real-time PCR: 12.5 µl of Premix Ex Taq (Perfect Real Time) (Takara Bio Inc.); 0.225 µl of PCR forward primer (100 µM); 0.225 µl of PCR reverse primer (100 µM); 0.625 µl of TaqMan probe (10 µM); 0.5 µl of Rox reference dye; 2 µl of cDNA; and 8.925 µl of PCR-grade water. A total amount of 25 µl was thus used. The initial step was carried out at 95° C. for 30 seconds. Then the next step was carried out at 95° C. for 5 seconds and then at 60° C. for 31 seconds and was repeated for 45 cycles.

The sequences of the probe and the primer were as follows:
SITH-1 forward primer: SEQ ID NO. 4,
SITH-1 reverse primer: SEQ ID NO. 5,
SITH-1 probe: SEQ ID NO. 6 (FAM sequence and TAMRA sequences were added to the 5 ' end and 3' end, respectively.)
GAPDH forward primer: SEQ ID NO. 7,
GAPDH reverse primer: SEQ ID NO. 8, and
GAPDH probe: SEQ ID NO. 9 (FAM sequence and TAMRA sequence were added to the 5' end and 3' end, respectively)

Figure 7:
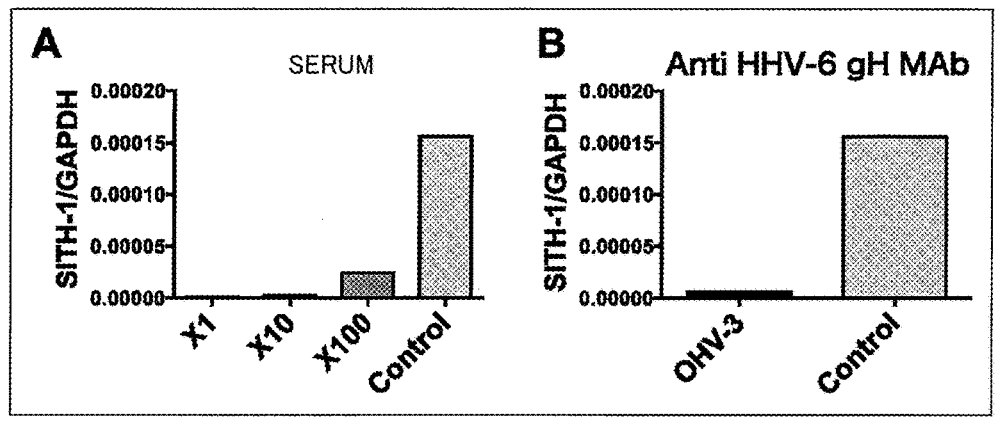
FIG. 7 shows the results of SITH-1 expression of HHV-6-infected U373.

Note that the data was analyzed with use of a Sequence Detection Software version 1.4 (Applied Biosystems). FIG. 7 shows the results obtained.

The results show that a greater degree of dilution of serum of healthy individuals led to a greater level of SITH-1 expression (see A of FIG. 7). It is therefore considered that anti-HHV-6 antibodies contained in serum of the healthy individuals prevented infection with HHV-6, and that SITH-1 expression was therefore restricted. In addition, SITH-1 expression in U373 cells were restricted as a result of reacting HHV-6 with serum or an anti-HHV-6B p98 (gH) monoclonal antibody before infection with the HHV-6 (see B of FIG. 7).

These results demonstrated that an increase in anti-HHV-6 antibody causes SITH-1 expression to be restricted.

(3.2) Restriction of SITH-1 Expression by Heparin and Anti-Heparan Sulfate Peptide An experiment was conducted by use of heparin and anti-heparan sulfate peptides serving as HHV-6 infection inhibitors.

U373 astrocytoma cells were removed with use of trypsin-EDTA, and then a medium (10% FBS-containing DMEM) was added, so that the resultant cells were at $1 \times 10^5$ cell/mL. Then, the U373 cells were reacted with 10 unit/mL of Novo-Heparin (Mochida Pharmaceutical Co., Ltd.) or 0.1 mM of anti-3-OS Heparan sulfate (HS) peptide trifluoroacetate salt (Sigma-Aldrich) at 4° C. for 1 hour. The U373 cells were also reacted only with a medium as a control at 4° C. for 1 hour. The resultant cells were washed 3 times with a medium. Then, the U373 cells thus washed were infected with a HHV-6 HST strain virus fluid ($2.9 \times 10^6$ ffu/ml) at a MOI of 3 by centrifugation. Then, the infected cells were cultured at 37° C. for 48 hours in a $CO_2$ incubator.

Figure 8:
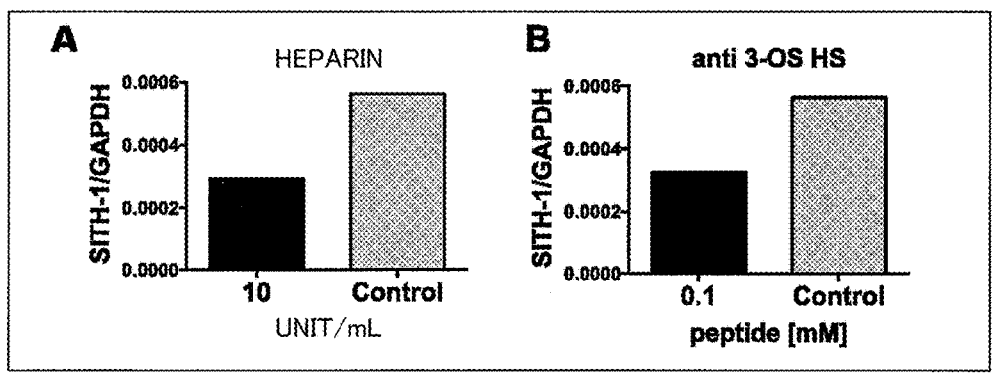
FIG. 8 shows the results of SITH-1 expression of HHV-6-infected U373.

From the resultant infected cells, RNA was purified by use of RNeasy Mini Kit (Qiagen) in accordance with the standard protocol. Then, cDNA was synthesized by use of a PrimeScript RT Reagent Kit (Takara Bio). Finally, expression levels of SITH-1 and GAPDH mRNA were measured by a method similar to that used in the above (3.1). FIG. 8 shows the results obtained.

In any of the case where heparin was used and the case where anti-heparan sulfate peptide was used, reacting the heparin or the anti-heparan sulfate peptide with the U373 cells before infection with HHV-6 caused SITH-1 expression in the U373 cells to be restricted (see A and B of FIG. 8).

(4) Structure and Function of SITH-1

(4.1) Identify of SITH-1

The human herpesvirus 6 variant B (HHV-6B) infects many people in childhood, causes roseola infantum, and establishes persistent infection or latent infection. In the present experiment, first, a brain-specific HHV-6B latent protein was identified. The identification of the HHV-6B latent protein was carried out by the following method.

(4.1.1) Method of Isolating SITH-1 mRNA

That is, we used a previously published HHV-6B latent infection system involving macrophage primary cultures (see Literatures 1 and 4). mRNA was isolated from a primary culture of macrophages (MΦ) which had been latently infected with HHV-6B and which had been induced to enter an intermediate state of enhanced HHV-6B latent transcript expression by using a reactivation stimulus. By using the mRNA purified from these primary cultures, a reverse transcription reaction was performed with a random primer, IE4RB (SEQ ID NO. 10) as the reverse transcription primer of the sense transcript, and IE2FB (SEQ ID NO. 11) as the reverse transcription primer of the antisense transcript.

Next, the product of the reverse transcription (cDNA) was amplified by PCR with the primers IE4RB and IE2FB and then by double-nested PCR with the inner primers IE4RA (SEQ ID NO. 12) and IE2FA (SEQ ID NO. 13). To confirm the presence of mRNA coded in the reverse direction as H6LT, reverse transcription reactions were made with a random primer, IE4RB as a reverse transcription primer for mRNA (sense strand) coded in the same direction as H6LT, and IE2FB as a reverse transcription primer for mRNA (antisense strand) coded in the opposite direction.

5'-RACE and 3'-RACE PCR were performed using previously reported methods (see Literatures 4 and 9). Approximately 20 dA residues were added to the 5' end of the cDNA, to which the anchor primer RL-1 (SEQ ID NO. 14) was annealed.

For the first 10 cycles of PCR, Taq polymerase (Roche Diagnostics) and primers N2 (SEQ ID NO. 15) and αR1 (SEQ ID NO. 16) were used under the following conditions: thermal denaturation, 94° C. for 1 min; annealing, 55° C. for min; and elongation reaction, 72° C. for 1 min. In subsequent PCR amplification, KOD Plus DNA polymerase (Toyobo) and primers N1 (SEQ ID NO. 17) and αR1 were used under the following conditions: thermal denaturation, 94° C. for 1 min; annealing, 65° C. for 30 s; and elongation reaction, 68° C. for 1 minute (15 cycles). The PCR amplification products were sequenced.

Then, the anchor primer RL-1 was annealed to the poly-A tail at the cDNA 3' end. For the first 10 cycles of PCR, Taq polymerase (Roche Diagnostics) and primers N2 and αF1 (SEQ ID NO. 18) were used under the following conditions: thermal denaturation, 94° C. for 1 min; annealing, 55° C. for 1 min; and elongation reaction, 72° C. for 1 min. In subsequent PCR amplification, KOD Plus DNA polymerase (Toyobo) and primers N1 (SEQ ID NO. 19) and αF1 were used under the following conditions: thermal denaturation, 94° C. for 1 min; annealing, 65° C. for 30 s; and elongation reaction, 68° C. for 1 minute (15 cycles). The PCR amplification products were sequenced (see C of FIG. 13).

(4.1.2) Results

Figure 9:
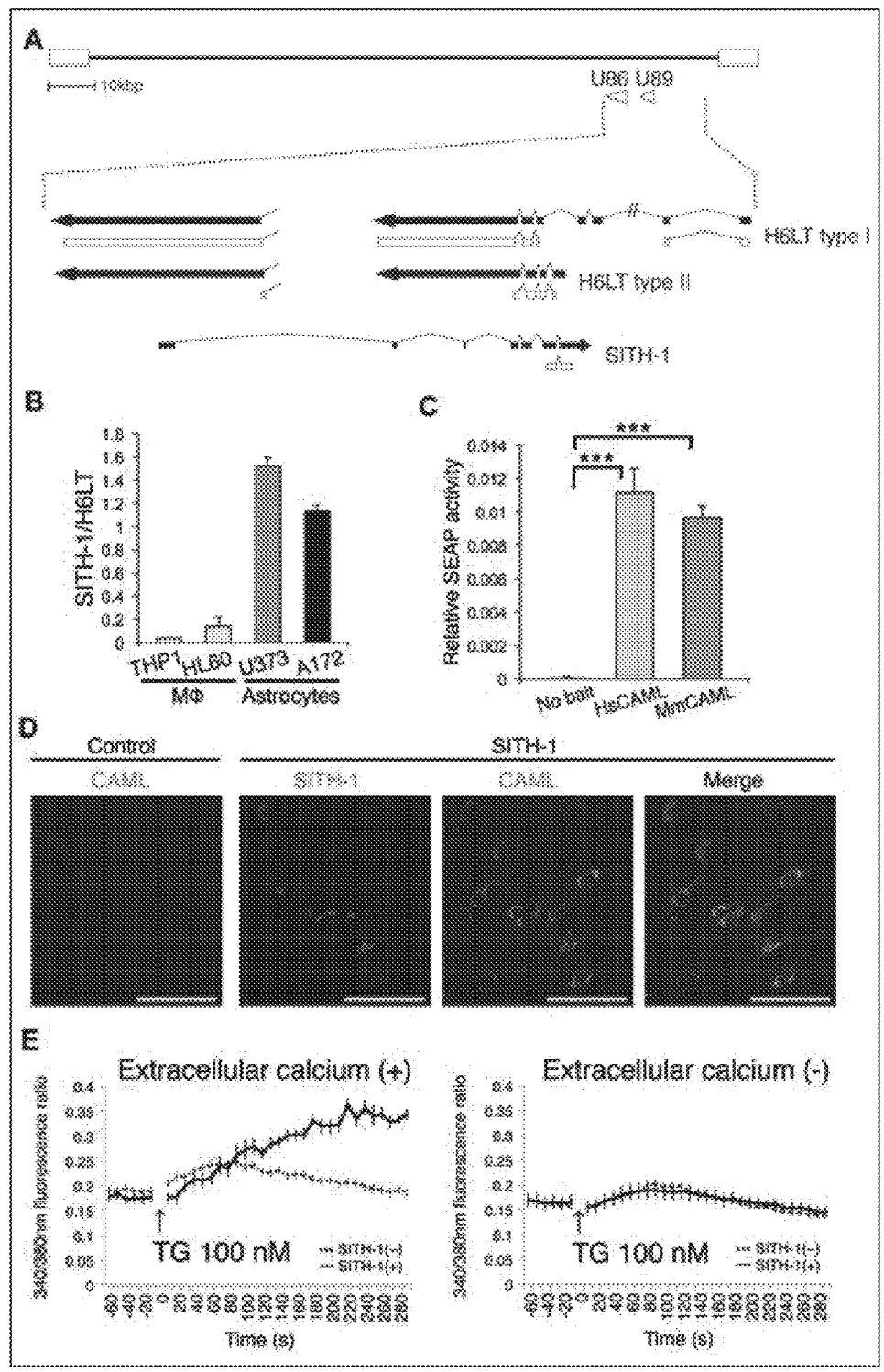
FIG. 9 shows structures and functions of SITH-1. A of FIG. 9 is a view showing a structure of SITH-1, a location of SITH-1 mRNA within an HHV-6B genome, and HHV-6B latent transcript (H6LT) types I and II. B of FIG. 9 is a view showing a ratio between the amount of SITH-1 mRNA and the amount of H6LT mRNA in a case of infection with HHV-6B. C of FIG. 9 is a view showing binding of SITH-1 and CAML as indicated by a mammalian two-hybrid system. D of FIG. 9 is a view showing the results of immunofluorescence staining in a case where SITH-1 was constitutively expressed in U373 cells. E of FIG. 9 is a view showing the results of measurement of intracellular calcium concentrations by fura 2-AM.
Figure 13:
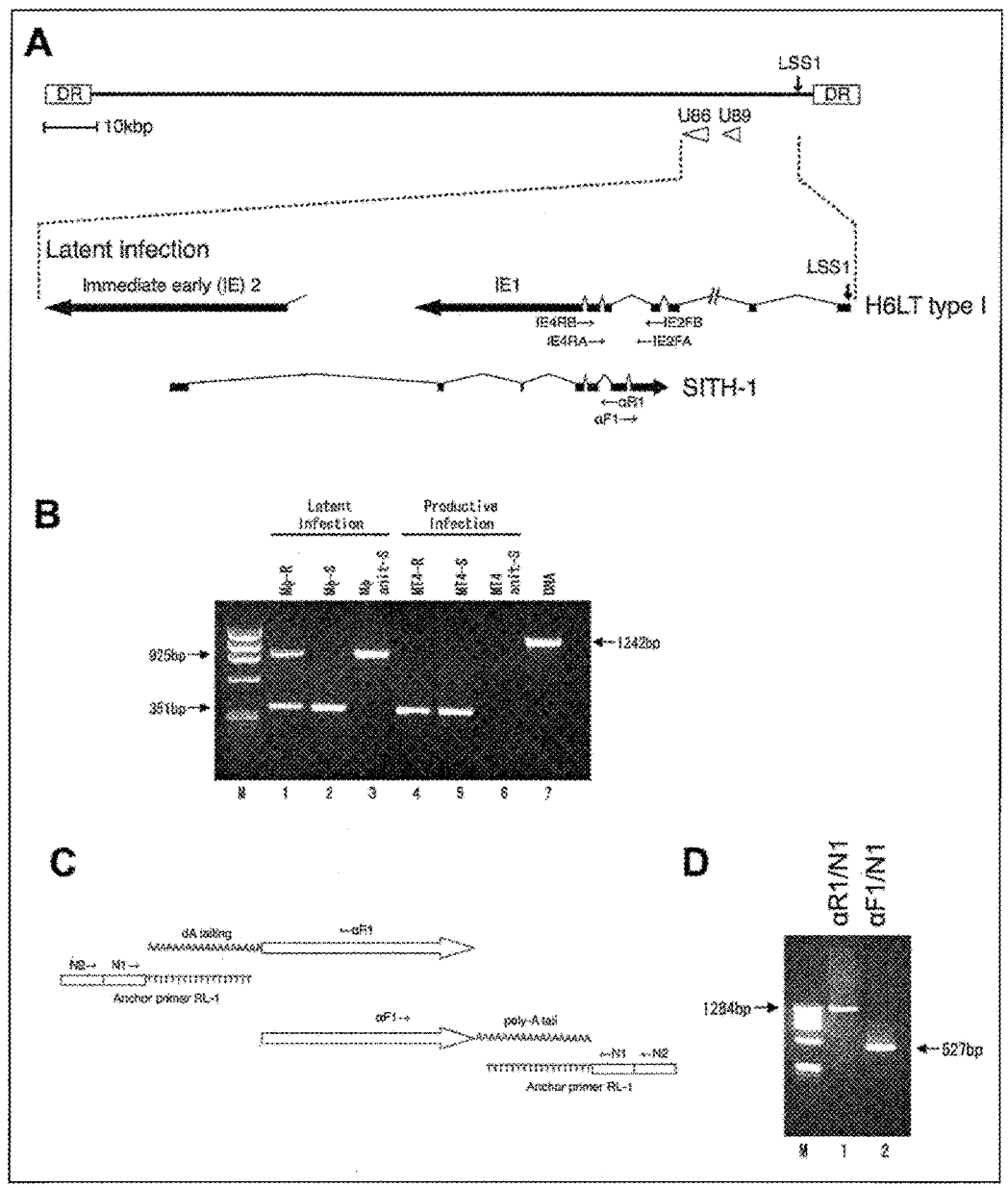
FIG. 13 shows the results of identification of the HHV-6B latent gene SITH-1. A of FIG. 13 is a view showing a primer design for SITH-1 cloning and identified SITH-1. The Upper panel is a view showing a structure of HHV-6B, including direct repeat (DR) sequences. The lower panel is a view showing a structure of the HHV-6B latent transcript H6LT. B of FIG. 13 shows the results of amplification of latent transcripts by double-nested RT-PCR. C of FIG. 13 is a view showing 3'- and 5'-RACE primers used to determine the structure of the mRNA from the latency-associated gene. D of FIG. 13 is a view showing the results of electrophoresis of products amplified by using 5'-RACE and 3'-RACE.

A brain-specific HHV-6B latent protein obtained by the method above was designated SITH-1 (small protein encoded by the intermediate stage transcript of HHV-6) (see A of FIG. 9 and A through D of FIG. 13).

Note that HHV-6B latent transcript (H6LT) type I and type II shown in A of FIG. 9 were previously reported (see Literatures 2 and 4). In A of FIG. 9, fine lines indicate introns, thick arrows indicate exons, and white boxes indicate open reading frames.

B of FIG. 13 shows the results of amplifying the latent transcripts by double-nested RT-PCR. Lanes 1-3 show the results of isolating mRNA from the primary cultures of the macrophages (MO) latently infected with HHV-6B. Lanes 4-6 show the results of testing, by the same method, the MT-4 cells which were productively infected with HHV-6B and which served as controls. For the reverse transcription reaction, the following primers were used: random primer in lanes 1 and 4; IE4RB in lanes 2 and 5; and IE2FB in lanes 3 and 6.

B of FIG. 13 confirmed that the sense-strand amplification product for the latently infected MΦ was a 351-bp product amplified from the gene product H6LT, which is specific to latent infection (lane 2). In contrast, a 925-bp product was amplified with the antisense-strand (lane 3). With the mRNA from the MT-4 cells that were productively infected by HHV-6B, only the 351-bp product was amplified from the sense strand (lanes 4-6). From HHV-6B DNA, a 1242-bp product was amplified (lane 7).

D of FIG. 13 confirmed that 1284-bp product and 527-bp product were amplified by 5'-RACE and 3'-RACE, respectively. In D of FIG. 13, lane 1 indicates 5'-RACE products, and lane 2 indicates 3'-RACE products. M indicates size markers.

(4.2) Tissue-Specific Expression of SITH-1

For the purpose of investigating the form of SITH-1 expression, macrophage (MΦ) cell lines THP-1 and HL-60 and astrocyte cell lines U373 and A172 were infected with HHV-6B. The cells were cultured and infected with the virus by the following method.

(4.2.1) Viruses and Cells

Macrophage cell lines THP-1 and HL-60 were cultured in Roswell Park Memorial Institute medium (RPMI 1640) containing 10% fetal bovine serum. Astrocytoma cell lines U373 and A172 were cultured in Dulbecco's modified Eagle's medium (DMEM) containing 10% fetal bovine serum. The HST strain of HHV-6B was used to infect the THP-1 and HL-60 cells at a multiplicity of infection (MOI) of 1 and the U373 and A172 cells at a MOI of 10 by centrifugation (37° C., 2000 g, 30 min).

(4.2.2) Real-Time RT-PCR

Total RNA was purified, by using BioRobot EZ1 and EZ1 RNA Cell Mini Kit (Qiagen), from the cells 7 days after the infection. cDNA was synthesized from total RNA by using a PrimeScript RT Reagent Kit (Takara Bio). mRNA amounts were quantified in duplicate by using FastStart TaqMan Probe Master (Rox) (Roche Diagnostics) and the Applied Biosystems 7300 Real-Time PCR system (Life Technologies). HHV-6B sense transcripts (also called "H6LT") were measured by using the following primers and probes. For SITH-1 and GAPDH, the primer described in the above (3.1) was used.

H6S forward primer: SEQ ID NO. 20,
H6S reverse primer: SEQ ID NO. 21, and
H6S probe: SEQ ID NO. 22 (FAM sequence and TAMRA sequences were added to the 5' end and 3' end, respectively.)

(4.2.3) Results

Figure 14:
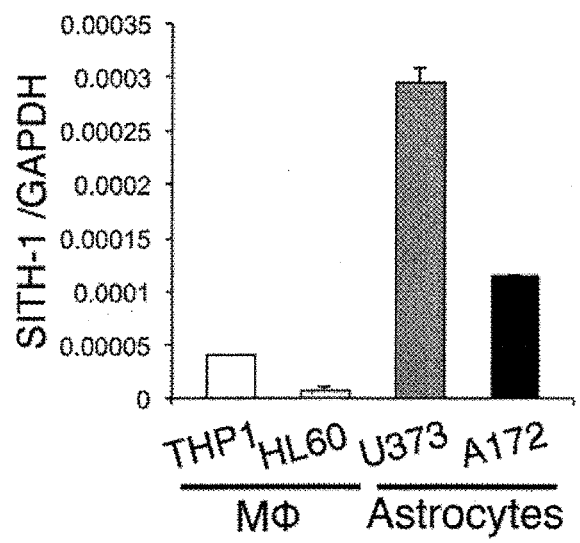
FIG. 14 shows the results of cell-specific expression of SITH-1 gene.

B of FIG. 9 and FIG. 14 confirmed that although HHV-6B latently infects both astrocytes and macrophages, SITH-1 expression selectively occurred in astrocyte cell lines (glial cells). No viral replication was observed in these cells. In FIG. 14, measured values are expressed as ratios of SITH-1 to GAPDH. Values are means±s.e.m.

(4.3) Binding of SITH-1 and Calcium Signal-Modulating Cyclophilin Ligand (CAML)

For the purpose of exploring a protein to be bound to SITH-1, yeast two-hybrid screening was carried out. Then, SEAP activity of the SITH-1-binding protein thus obtained was measured by mammalian two-hybrid assay.

(4.3.1) Yeast Two-Hybrid Screening

The Matchmaker Two-Hybrid System 2 (Clontech Laboratories) was used to screen for proteins that interact with SITH-1 protein by following a standard protocol.

SITH-1 was cloned into a pAS2-1 vector to produce a fusion protein of SITH-1 and a GAL4 DNA-binding domain (DNA-BD). SITH-1 was amplified from SITH-1 cDNA by PCR.

To investigate interactions with SITH-1, pAS2-1-SITH-1 was screened against the human fetal brain Matchmaker cDNA Library pACT2 (Clontech Laboratories) and Pretransformed Matchmaker cDNA Libraries Mouse 17-day Embryo (Clontech Laboratories) by using a selective culture medium (without histidine, leucine, and tryptophan) in accordance with a standard protocol. The approximately 30 yeast clones obtained were sequenced, the majority of which were identified as including CAML or CAML fragments.

(4.3.2) Mammalian Two-Hybrid Assay

The Mammalian Matchmaker Two-Hybrid Assay Kit (Takara Bio) was used to confirm the binding of SITH-1 and CAML in mammalian cells. SITH-1 was cloned into a pM (GAL4) plasmid (pM-SITH-1). Human CAML and mouse CAML were cloned into pVP-16 plasmids (pVP-16-HsCAML, pVP16-MmCAML). Human CAML was amplified by PCR from the pCMV-SPORT6-CAML plasmid (Invitrogen). Mouse CAML was amplified by PCR from mouse fetal brain cDNA. 293T cells were co-transfected with the pG5SEAP Reporter plasmid; pM-SITH1 or pM (GAL4) plasmid; pVP16-HsCAML, pVP16-MmCAML, or pVP16 plasmid; and the pMetLuc-Control plasmid as an internal control.

SEAP activity was measured using the Great EscAPe SEAP Chemiluminescence Kit (Takara Bio). Secreted luciferase activity was measured using the Secreted Luciferase Reporter System (Takara Bio).

(4.3.3) Results

C of FIG. 9 confirmed that, in both humans and mice, SITH-1 is bound to CAML which is a protein highly expressed in the brain. Note that in C of FIG. 9, *** indicates P<0.0005.

(4.4) Influence of SITH-1 on CAML mRNA Expression

To investigate whether or not SITH-1 has influence on CAML mRNA expression, the state of CAML mRNA expression was investigated in the cells expressing SITH-1. Then, intracellular calcium concentrations were examined in the cells expressing SITH-1. Intracellular expression of SITH-1, measurement of the intracellular expression level (mRNA and protein), and measurement of intracellular calcium concentrations were carried out by the following method.

(4.4.1) Preparation of Constitutively SITH-1-Expressing U373 Cells

A SITH-1-expressing recombinant retrovirus was prepared using the Retro-X Universal Packaging System (Takara Bio) in accordance with standard methods. SITH-1 was cloned into the retrovirus vector pQCXIP (pQC-SITH-1-IP). This vector can be made to constitutively express the genes for SITH-1, IRES, and puromycin resistance under the control of the cytomegalovirus (CMV) early-stage promoter.

The envelope vector p10A1 and either pQC-SITH-1-IP or pQCXIP (no insert) were co-transfected using the packaging cell GP2-293 and the calcium phosphate method. The recombinant retrovirus was prepared in the GP2-293 cells, and the viral supernatant was recovered 48 hours after transfection. U373-MG astrocytoma cells were infected with the recombinant retrovirus. After infection, the cells were treated with 1 µg/mL puromycin (Calbiochem) to select either constitutively SITH-1-expressing U373 cells (U373-SITH-1) or U373 cells infected with the retrovirus vector (no insert; U373-Vector).

(4.4.2) Measurement of CAML mRNA

Total RNA was purified from U373-SITH-1 and U373-Vector cells by using BioRobot EZ1 and EZ1 RNA Cell Mini Kit (Qiagen). cDNA was synthesized from total RNA by using a PrimeScript RT Reagent Kit (Takara Bio). Human CAML mRNA amounts were quantified in duplicate by using SYBR Premix Ex Taq (Takara Bio) and the Applied Biosystems 7300 Real-Time PCR system (Life Technologies). Measurement was carried out by using the following primers and probes:
HsCAML forward primer: SEQ ID NO. 23, and
HsCAML reverse primer: SEQ ID NO. 24

(4.4.3) Production of Antibody SITH-1 amplified by PCR was cloned into a pET-42a(+) DNA plasmid (pET42-SITH-1), and GST-tagged SITH-protein was expressed in chaperone-competent pG-TF2/BL21 cells. Rabbits were inoculated with purified GST-tagged SITH-1 protein to produce anti-SITH-1 rabbit polyclonal antibodies.

(4.4.4) Immunofluorescence Staining

U373-SITH-1 and U373-Vector cells were fixed in cold acetone/methanol for 10 min. The fixed cells were reacted with anti-SITH-1 rabbit polyclonal antibodies and anti-CAML goat polyclonal antibodies (Santa Cruz Biotechnology) at 37° C. for 1 hour.

After washes in PBS, Alexa Fluor 594 donkey anti-rabbit secondary antibodies (Molecular Probes) and Alexa Fluor 488 donkey anti-goat secondary antibodies (Molecular Probes) were added and reacted at 37° C. for 30 min. The washes in PBS were then repeated. After the samples had been mounted on a slide with a cover glass they were observed under the same optical conditions by using an Olympus BX51 microscope and a CCD camera (DP70, Olympus).

(4.4.5) Measurement of Intracellular Calcium Concentration

U373 cells expressing SITH-1 [SITH-1(+)] or U373 cells not expressing SITH-1 [SITH-1(−)] were cultured on a glass slide. The fluorescent calcium reagent fura-2 acetoxymethyl ester (fura-2AM, Molecular Probes) was added to DMEM culture medium containing 10% FBS and reacted at 37° C. for 30 minutes under dark conditions so that the reagent was taken up by the cells.

The cells were washed on the slide and then immersed in Hanks's Balanced Salt Solution (HBSS) with or without calcium. The cells were stimulated with the calcium ATPase inhibitor thapsigargin (100 nM, Calbiochem). Images at excitation wavelengths of 340 nm and 380 nm were taken under a microscope with a CCD camera (IX71, DP70, Olympus) and Lumina Vision software (Mitani Corporation). The mean luminance of six cells was measured by using ImageJ (NIH).

(4.4.6) Results

Figure 15:
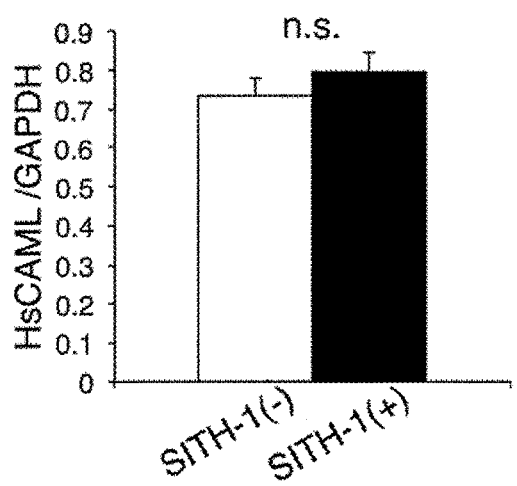
FIG. 15 shows the results of examining the influence of SITH-1 gene on CAML mRNA expression.

D of FIG. 9 and FIG. 15 confirmed that SITH-1 caused CAML protein to accumulate in astrocytes without changing its mRNA expression level. CAML protein expression was weak in U373 cells not expressing SITH-1 (control) but increased in U373 cells expressing SITH-1 (see D of FIG. 9). It was confirmed that SITH-1 promoted an increase in calcium influx in astrocytes (see E of FIG. 9), which may cause neurotoxicity. That is, it was found that in a case where there is extracellular calcium, SITH-1 has a function to promote calcium influx into a cell by TG stimulation. Note that in D of FIG. 9, red color indicates SITH-1, and green color indicates CAML. Scale bar is 100 µm. In E of FIG. 9, cells were stimulated with thapsigargin (TG) at time 0. Values are means±s.e.m. In FIG. 15, measured values are expressed as ratios of HsCAML to GAPDH. Values are means±s.e.m.

(5) Relationship Between Anti-SITH-1 Antibody Titers, Stress, and Suicide Attempt (5.1) Relationship Between HHV-6B and Working Hours For the purpose of investigating a relationship between reactivation of HHV-6B and working hours, a test was conducted with 29 healthy volunteers. Specifically, the test was conducted by the following method.

(5.1.1) Test Subject

To investigate the relationship between stress and HHV-6B in saliva, the study enrolled 29 healthy volunteers (42.6±1.8 [means±s.e.m] years of age; 15 women and 14 men). They were recruited by using an advertisement placed by Soiken Inc. (see Literature 5). Participants were excluded if they were taking any chronic medications or supplemental vitamins or if they weighed less than 40 kg. They were also excluded if they had donated blood within a month of the study, their blood hemoglobin level was less than 12.0 g/dL, or they slept less than 7 hours.

(5.1.2) Saliva Samples

Viral DNA was extracted from 400 µL samples of saliva by automatic isolation with the BioRobot EZ1 workstation and EZ1 virus mini kit v2.0 (Qiagen), in accordance with the manufacturer's protocol. DNA was eluted in 90 µL of elution buffer.

Copies of HHV-6B DNA in the saliva samples were quantified by real-time PCR with an Applied Biosystems 7300 real-time PCR System. Amplifications were performed in duplicate in a total volume of 50 µL containing 25 µL of Premix Ex Taq (Perfect Real Time; Takara Bio Inc., Otsu, Japan), 0.45 µL of PCR forward primer (100 µM), 0.45 µL of PCR reverse primer (100 µM), 1.25 µL of TaqMan probe (10 µM), 1 µL of Rox reference dye, 5 µL of the viral DNA, and 16.85 µL of PCR-grade water. The primers used for real-time PCR were as follows:
HHV-6B forward primer: SEQ ID NO. 25,
HHV-6B reverse primer: SEQ ID NO. 26, and
HHV-6B probe: SEQ ID NO. 27 (FAM sequence and TAMRA sequences were added to the 5' end and 3' end, respectively.)

The thermal profile was 95° C. for 30 seconds, followed by 50 cycles of 95° C. for 5 seconds and 60° C. for 31 seconds. Data analysis was performed with Sequence Detection Software version 1.4 (Life Technologies).

(5.1.3) Results

Figure 10:
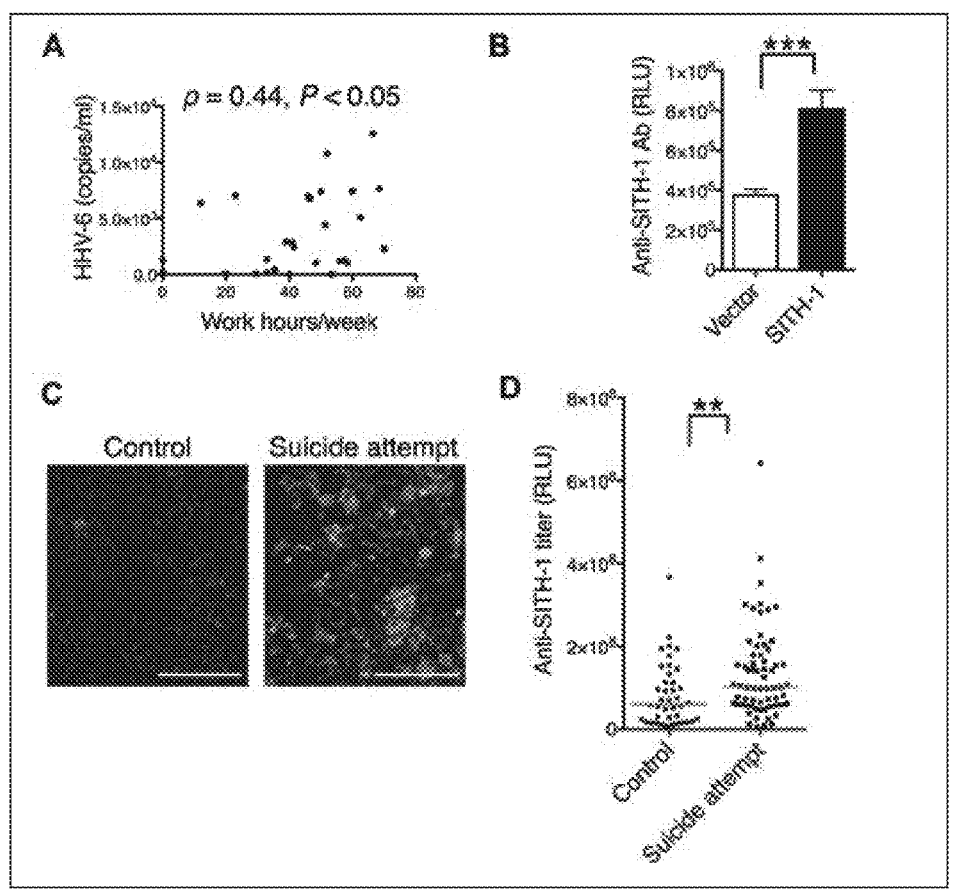
FIG. 10 shows anti-SITH-1 antibody titers, stress, and a relationship to suicide attempt. A of FIG. 10 is a view showing the results of comparison between the number of HHV-6B DNA copies in saliva and working hours for a period of one week. B of FIG. 10 is a view showing anti-SITH-1 IgG antibody titers in the peripheral blood of mice expressing SITH-1 in astrocytes. C of FIG. 10 is a view showing the results of examining anti-SITH-1 antibodies in the plasma of a healthy subject (control) and a patient who attempted suicide (hereinafter also referred to as "suicide attempter") by use of an indirect fluorescent antibody assay. D of FIG. 10 is a view showing anti-SITH-1 antibody titers in healthy subjects (controls) and suicide attempters.

A of FIG. 10 confirmed that HHV-6B DNA copy numbers in saliva (a main preserver of persistent HHV-6B) and working hours recorded over a 1-week period in 29 healthy volunteers (15 females, 14 males) revealed a positive correlation. This suggests that stress increases the reactivation of persistent HHV-6B.

Note that in A of FIG. 10, p=0.44, and P<0.05. The test was conducted with use of spearman rank correlation coefficient.

(5.2) SITH-1 IgG Antibody

For the purpose of demonstrating that HHV-6B invasion of the brain can be evaluated by use of a plasma anti-SITH-1 antibody test, (i) a control vector or SITH-1 was administered to mice and then (ii) Anti-SITH-1 IgG antibody titers in the peripheral blood of the mice were examined. The administration of the control vector or SITH-1 and the measurement of the anti-SITH-1 IgG antibody titers were carried out by the following method.

(5.2.1) Mice and SITH-1 Inoculation

Pregnant C57BL/6CrSlc mice were purchased from SLC Japan. The mice were kept in standard cages in an animal room under temperature- and humidity-controlled conditions, with a light/dark cycle of 12 hours each (lights on at 09:00) and free access to food and water. On the day of birth, the neonatal mice were given an injection of either the Ad-GFAP-SITH1 (SITH-1) or Axcwit (vector) recombinant adenovirus into the right temporal lobe of the brain by using a 30 G syringe. All animal experiments were performed in accordance with animal experiment regulations and approved by the Animal Care and Use Committee of the Jikei University School of Medicine.

(5.2.2) Indirect Fluorescent Antibody (IFA) Assay

SITH-1 was cloned into pFLAG-CMV2 (Sigma-Aldrich) under control of the CMV promoter (pFLAG-SITH-1-CMV2) by using standard molecular biological methods. pFLAG-SITH-1-CMV2 was transfected into HEK293T cells cultured on Lab-Tek chamber slides (Nunc) by using Lipofectamine LTX (Invitrogen).

Plasma was diluted 160-fold using the immunoreaction enhancer solution Can Get Signal immunostain solution (Toyobo). The plasma was reacted on the slide overnight at 4° C. After washes with PBS—0.05% Tween 20, the slide was reacted at 37° C. for 1 h with Alexa Fluor 488 goat anti-human secondary antibodies (Molecular Probes) diluted 200-fold with Can Get Signal immunostain solution. After washes with PBS-0.05% Tween 20, a cover glass was mounted on the slide. All samples were observed under the same conditions by using an Olympus BX51 microscope and CCD camera.

(5.2.3) Results

B of FIG. 10 confirmed that when SITH-1 was produced in mouse astrocytes, SITH-1 IgG antibody titers in the blood increased. This is consistent with the suggestion that these cells make up the blood-brain barrier.

In B of FIG. 10, values are means±s.e.m., and RLU indicates relative light units.

(5.3) Relationship Between Anti-SITH-1 Antibody Titer and Attempted Suicide

Figure 17:
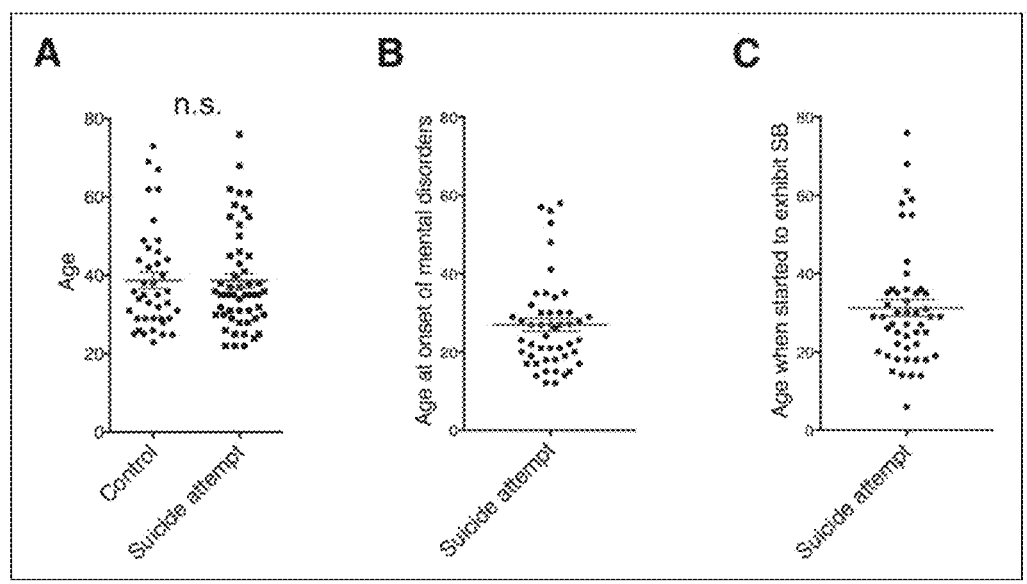
FIG. 17 shows distributions of subjects by current age, age of onset of mental disorder, and age when suicidal behavior (SB) began. A of FIG. 17 is a view showing a distribution of current ages of healthy subjects (controls) and suicide attempters. B of FIG. 17 is a view showing a distribution of ages of onset of mental disorder in suicide attempters. C of FIG. 17 is a view showing a distribution of ages when SB began in suicide attempters.

For the purpose of investigating a relationship between anti-SITH-1 antibody titers and attempted suicide, patients with psychiatric diseases who had been hospitalized because of attempted suicide were enrolled (see A through C of FIG. 17). The tests were performed on plasma samples collected on the day the patients were hospitalized, immediately after their suicide attempts. For the purpose of detecting anti-SITH-1 antibodies in plasma, the indirect fluorescent antibody assay was used.

(5.3.1) Subject

To investigate the relationship between attempted suicide and plasma anti-SITH-1 antibody titer, the study enrolled 66 patients (31 males, 35 females) who had unsuccessfully attempted suicide and had received emergency care at Tokyo Metropolitan Matsuzawa Hospital (see Literature 3).

These patients were diagnosed by using the structured clinical interview for DSM-IV Axis I disorders, clinician version (SCID-I, CV). The study population consisted of 33 patients with major depressive disorder, 11 with bipolar disorder, 11 with schizophrenia, and 11 with other mental disorders. Forty healthy volunteers (11 males, 29 females) with no history of psychiatric consultations served as controls. Other than stress, factors related to HHV-6B reactivation are known to include drug-induced hypersensitivity syndrome and strong immunosuppression. However, the patients in this study did not have any symptoms suggestive of these conditions.

(5.3.2) Results

C and D of FIG. 10 show that anti-SITH-1 antibody titers were significantly higher in the attempted suicide group than in controls. Anti-SITH-1 antibody was positive in 38 (57.6%) of 66 suicide attempters.

In C of FIG. 10, scale bar is 100 μm. In D of FIG. 10, horizontal lines show median values, and ** indicates P<0.01.

Figure 20:
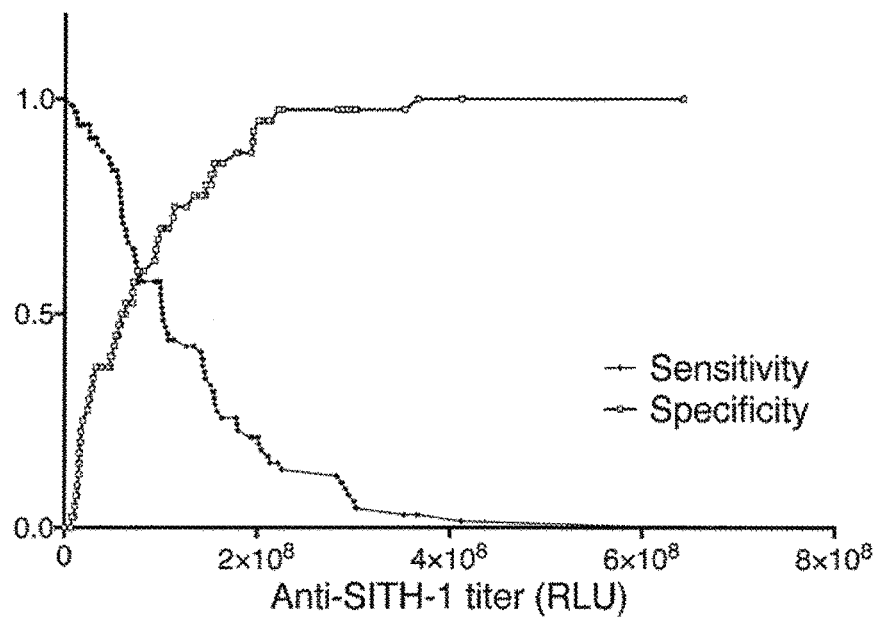
FIG. 20 shows the results of examining sensitivity and specificity of anti-SITH-1 antibody titers for predicting suicide attempts.

FIG. 20 shows the results of examining sensitivity and specificity of anti-SITH-1 antibody titers for predicting suicide attempts. In FIG. 20, black circles indicate sensitivity, and white circles indicate specificity. X-axis shows anti-SITH-1 antibody titers. Sensitivity of the anti-SITH-1 antibody titers was 57.6% at a specificity of 70.0% (10.1% cut-off) and 33.3% at a specificity of 82.5% (15.6% cut-off).

(5.4) Relationship Between Mental Disorder and Age Among Subjects

Then, for the purpose of investigating a relationship between ages of the subjects and onset of mental disorders, the following experiment was conducted.

(5.4.1) Test

As was the case of (5.3.1), 66 patients (31 males, 35 females) who had unsuccessfully attempted suicide and had received emergency care at Tokyo Metropolitan Matsuzawa Hospital were enrolled as an attempted suicide group. 40 healthy subjects (11 males, 29 females) who had had no history of receiving psychiatric care were enrolled as controls. A relationship between a mental disorder and age and a relationship between a mental disorder and age of onset were analyzed.

(5.4.2) Results

The controls were aged 38.8±2.1 years (mean±s.e.m.), and the attempted suicide group were aged 38.7±1.8 years (mean±s.e.m.) (see A of FIG. 17). This shows that there was no significant difference observed between the two groups. (n.s. indicates that there was not significant difference.) The mean age of disease onset (±s.e.m.) among the attempted suicide group was 26.9±1.7 years (see B of FIG. 17). The mean age when SB began (±s.e.m.) among the attempted suicide group was 31.2±2.1 years (see C of FIG. 17).

(6) Influence of SITH-1 Expression in Astrocytes (6.1) Relationship Between SITH-1 and Stress and the Like For the purpose of investigating the effects of the latent protein SITH-1 that can be produced during abortive or persistent infection of HHV-6B in astrocytes, an experiment was conducted in which an adenovirus vector that expresses SITH-1 under the control of the glial fibrillary acidic protein (GFAP) promoter was injected into the mouse brain to achieve astrocyte-specific production of SITH-1. The injection of the adenovirus vector into the mice was carried out by a method similar to that described above.

(6.1.1) Immunofluorescence Staining

For immunostaining of the whole brain from 3-week-old SITH-1-expressing mice, the tissue was first subjected to perfusion fixation with 4% PFA. After the slices were blocked with 2% bovine serum albumin (BSA), they were reacted with anti-SITH-1 rabbit antibodies (diluted 1:1000) and anti-GFAP polyclonal chicken antibodies (Abcam; diluted 1:500) at 25° C. for 16 hours.

After washes in PBS, Alexa Fluor 594 donkey anti-rabbit secondary antibodies (diluted 1:400) and Alexa Fluor 488 goat anti-chicken secondary antibodies (Molecular Probes; diluted 1:400) were added and reacted at 37° C. for 30 min to detect SITH-1 and GFAP. Washes in PBS were then repeated. After the samples were mounted on a slide with a cover glass, they were observed by using an Olympus BX51 microscope and a CCD camera (DP70, Olympus).

(6.1.2) Real-Time RT-PCR

Real-time RT-PCR was carried out by use of samples three or five weeks after the mice brain administration of adenovirus vector that expresses SITH-1. Total RNA was purified from mouse whole brain by using BioRobot EZ1 and EZ1 RNA Universal Tissue Kit (Qiagen). cDNA was synthesized from total RNA by using a PrimeScript RT Reagent Kit (Takara Bio).

mRNA amounts were quantified in duplicate by using FastStart TaqMan Probe Master (Rox) (Roche Diagnostics) and the Applied Biosystems 7300 Real-Time PCR system (Life Technologies). CRH, mouse BDNF, and β-actin (ACTB) were measured by using primers and probes below. The primer described in the above (3) was used for SITH-1.
BDNF forward primer: SEQ ID NO. 28,
BDNF reverse primer: SEQ ID NO. 29,
BDNF probe: SEQ ID NO. 30 (FAM sequence and TAMRA sequences were added to the 5' end and 3' end, respectively.),
MmACTB forward primer: SEQ ID NO. 31,
MmACTB reverse primer: SEQ ID NO. 32, and
MmACTB probe: SEQ ID NO. 33 (FAM sequence and TAMRA sequences were added to the 5' end and 3' end, respectively.)
CRH forward primer: SEQ ID NO. 34,
CRH reverse primer: SEQ ID NO. 35, and
CRH probe: SEQ ID NO. 36 (FAM sequence and TAMRA sequences were added to the 5' end and 3' end, respectively.)

(6.1.3) Prepulse Inhibition Measurements

PPI was measured by using the SR-LAB startle response system (San Diego Instruments). A test session was composed of 32 trials, and each trial comprised a prepulse sound (0, 74, 78, 82, or 86 dB) paired with a 120 dB stimulus. The percentage PPI was calculated as

[(ASR amplitude of trial without prepulse)−(ASR amplitude of trial with prepulse)]/(ASR amplitude of trial without prepulse)×100, where ASR is the acoustic startle response.

(6.1.4) Tail Suspension Test

A tail suspension test was conducted by a method similar to that described in the above (2.2).

(6.1.5) Measurement of Locomotor Activity

Wheel running activity 5 weeks postinoculation (p.i.) was measured. Wheel running activity was measured by (i) placing mice individually in a cage (9 cm wide×22 cm deep×9 cm high) equipped with a steel mouse wheel (5 cm wide×20 cm in diameter) and (ii) recording the amount of wheel-running activity (one rotation=3 counts) with a computer system (CLEA Japan). Total activity over a 48-hour period, activity during dark periods, and activity during light periods are shown.

(6.1.6) Results

Figure 11:
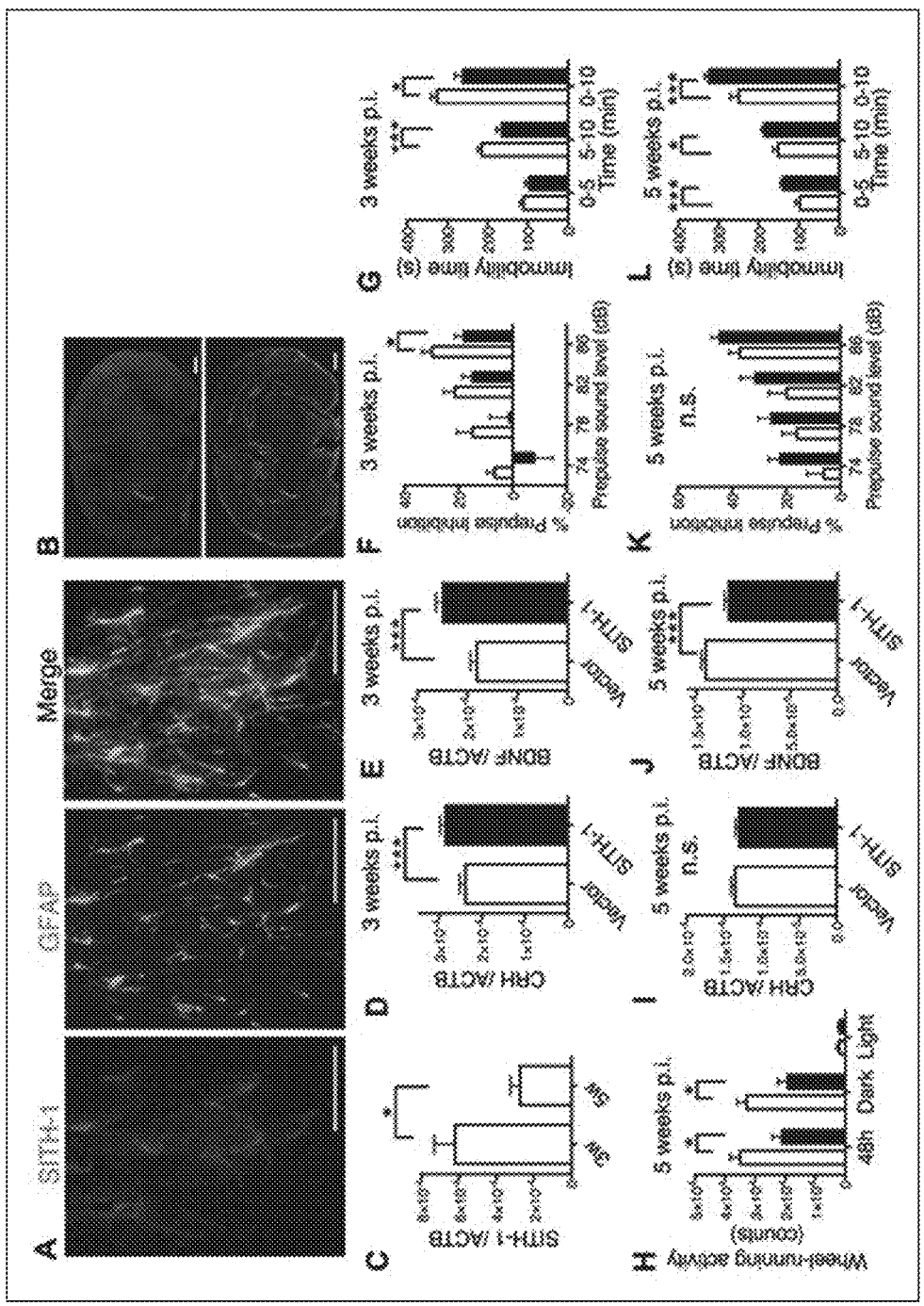
FIG. 11 shows mood disorder-like behaviors of mice expressing SITH-1 in astrocytes. A of FIG. 11 is a view showing the results of staining of brain slices by an indirect fluorescent antibody method three weeks postinoculation (p.i.). C through E, I, and J of FIG. 11 are views showing the results of expression of the indicated mRNAs three or five weeks postinoculation (p.i.) in whole mouse brains. F and K of FIG. 11 are views showing the percentage of prepulse inhibition at 3 weeks (F) and 5 weeks (K) postinoculation (p.i.) with virus vectors. G and L of FIG. 11 are views showing the results of tail suspension tests at 3 weeks (F) and 5 weeks (K) postinoculation (p.i.) with virus vectors. H of FIG. 11 is a view showing wheel running activity 5 weeks postinoculation (p.i.) with virus vectors.

FIG. 11 shows the results of investigating the relationship between SITH-1 and stress and the like. In A of FIG. 11, red color indicates SITH-1, and green color indicates GFAP. Scale bar in A of FIG. 11 is 100 μm, and scale bar in B of FIG. 11 is 1 mm. In D through L of FIG. 11, white columns (Vector) show the results of administration of control adenovirus vector, and black columns (SITH-1) show the results of administration of SITH-1-bearing adenovirus. C through E, I, and J of FIG. 11 show the results of expression of the indicated mRNAs in whole mouse brains three or five weeks postinoculation (p.i.) with virus vector, which results show ratios to β-actin (ACTB). F and K of FIG. 11 show the percentage of prepulse inhibition at 3 weeks (F) and 5 weeks (K) after paired prepulse (74, 78, 82, and 86 dB) and pulse (120 dB) stimuli were administered. G and L of FIG. 11 show the results of tail suspension test 3 weeks (G) and 5 weeks (L) postinoculation (p.i.) with virus vector. Duration of immobility (in seconds) during the 0- to 5-, 5- to 10-, and 0- to 10-min time blocks are shown. Note that in FIG. 11, values are means±s.e.m., * indicates P<0.05, and *** indicates P<0.005.

A and B of FIG. 11 confirmed SITH-1 expression in astrocytes three weeks postinoculation (p.i.). Greater SITH-1 expression was confirmed 3 weeks postinoculation (p.i.) than at 5 weeks postinoculation (p.i.) (see C of FIG. 11).

D through G of FIG. 11 confirmed, at 3 weeks postinoculation (p.i.), increased CRH, increased brain-derived neurotrophic factor (BDNF), decreased prepulse inhibition (PPI) of the acoustic startle response, and shortened periods of immobility in the tail suspension test (TST) (all markers shown here are intended for severe stress, anxiety, and irritability).

Figure 21:
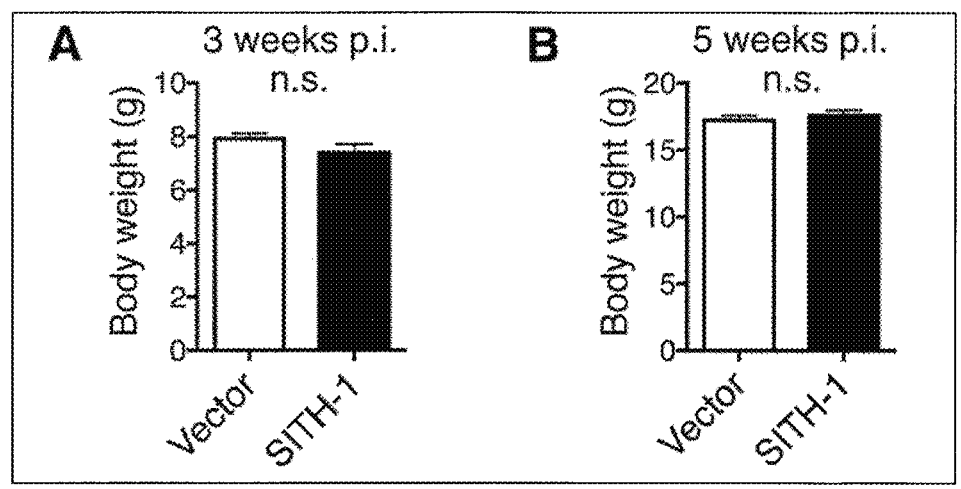
FIG. 21 shows the results of examining body weights of mice expressing (SITH-1) and not expressing (vector) SITH-1 in astrocytes at 3 weeks postinoculation (p.i.) (A) and 5 weeks p.i. (B).

H, J, and L of FIG. 11 and FIG. 21 confirmed, at 5 weeks postinoculation (p.i.), decreased wheel-running activity and BDNF expression, as well as prolonged immobility in the TST. All of the markers shown are intended for depression. I of FIG. 11 shows that levels of CRH returned to normal in five weeks.

These data suggest that SITH-1 induced irritability and anxiety via increased CRH in the early phase of its production and led to depression as its production decreased over time.

(7) SITH-1 Exposure and Clinical Symptoms (7.1) Relationship Between SITH-1 Production and Attempted Suicide Because production of SITH-1 led to mood disorder-like behavior in animal models, the relationship between SITH-1 production and the symptoms of suicide attempters was investigated. SITH-1 production was measured by a method similar to that described in the above (5.3) and by comparing anti-SITH-1 antibody titers. The subjects (suicide attempters) examined were the same as in the above (5.3).

(7.1.1) Results

A of FIG. 12 shows the results of investigating relationships with various methods of attempted suicide: jumping, drug overdose, self-cutting, and self-strangulation. As indicated by high anti-SITH-1 antibody titers in A of FIG. 12, patients who had recently been exposed to high levels of SITH-1 tended to attempt suicide by jumping. This suggests that this marker allows identification of a more serious suicide attempt. This is consistent with the results in the mouse model, which showed anxiety and irritability in the early phase of SITH-1 production.

(7.2) Determination of Suitable Urea Concentration for the Avidity Index (AI) Assay For the purpose of determining suitable urea concentration in the AI assay, beads bound to SITH-1 antigen (SITH-1-TM2 fusion protein) were produced. Then, anti-SITH-1 antibody titers were measured after (i) reaction of plasma with the SITH-1-TM2 fusion protein and then (ii) washes in 0, 2, 4, 6, or 8 M urea.

(7.2.1) Preparation of SITH-1 Tamavidin Fusion Protein and SITH-1 Biotin

For the purpose of detecting SITH-1 antibodies with a bead-ELISA method by using, as an antigen, a fusion protein of SITH-1 and the avidin-like biotin-binding protein tamavidin 2 (expressed in *E. coli*) (see Literature 8), constructs were prepared to express the following:

a fusion protein of SITH-1 and tamavidin 2 in a pTrc99A plasmid (pTrc99A-SITH-1-TM2); BioEase-tagged fusion SITH-1 created by inserting SITH-1 into a pET104.1-DEST vector plasmid (pET104.1-SITH-1); and tamavidin 2 (pTrc99A-TM2). A mutated tamavidin 2 gene (LATM2) was cloned into a pKK233-2 plasmid (pKK233-2-LATM2).

In accordance with the method of Takakura et al. (see Literature 8), Using the pTrc99A-SITH-1-TM2, pTrc99A-SITH-1-biotin, and pTrc99A-TM2 plasmids, SITH-1-TM2 fusion protein, SITH-1-biotin fusion protein, or TM2 protein were expressed in a BL21 strain of *E. coli*. The *E. coli* were cultured at 18° C. for 64 h in Overnight Express Instant LB medium (Novagen).

The solution was centrifuged to collect *E. coli* pellets, which were suspended in Complete—0.1 M HEPES—KOH (pH 7.4), and soluble proteins were obtained through ultrasound fragmentation. Cell debris and insoluble proteins were eliminated by centrifugation. The supernatant was used as the lysate for the fusion protein of SITH-1 and tamavidin (SITH-1-TM2), SITH-1-biotin fusion protein (SITH-1-biotin), and tamavidin protein (TM2).

(7.2.2) Anti-SITH-1 IgG Antibody ELISA

Anti-SITH-1 IgG antibody titers in the plasma are measured as follows. Biotinylated magnetic beads were produced by reacting 1 mL of 100 mg/mL EZ-Link NHS-PEG12-biotin solution (Pierce) with 10 mL Dynabeads M-270 Amine beads (Invitrogen) at room temperature for 30 min. The biotinylated magnetic beads were washed five times in 0.1% BSA/PBS/0.01% Tween 20 and then suspended in 20 mL 0.01% azide/1×PBS (−). SITH-1-TM2 lysate or TM2 lysate was added to the biotinylated beads so that the protein concentration became 2 mg/μL, and the solution was reacted at room temperature for 1 h. The beads were washed five times in TBS/0.2% Tween 20, then suspended in an amount of 0.01% sodium azide/1×PBS (−) solution equal in volume to that of the magnetic bead solution used for biotinylation to give SITH-1-TM2 beads or TM2 beads. SITH-1-TM2 beads (5 μL) were reacted at room temperature for 1 hour with 200 μL diluted human plasma (diluted 1:1000 in LATM2 lysate) or 200 μL mouse plasma (diluted 1:100 in LATM2 lysate).

To measure SITH-1-specific high-avidity antibody, the beads were washed three times in (i) 200 μL of 0.2% Tween 20-TBS or (ii) 200 μL of 0, 2, 4, 6, or 8M urea in 0.2% Tween 20-TBS.

After the washes, the beads were reacted at room temperature for 1 h with 200 μL peroxidase-conjugated goat anti-human IgG (H+L) (Jackson ImmunoResearch Laboratories; diluted 1:10,000 in LATM2 lysate). The beads were then washed three times in 0.2% Tween 20/TBS. After the supernatant was removed, 50 μL SuperSignal ELISA Femto Stable Peroxide Solution (Pierce) was added to each sample and the beads were transferred to a white 96-well plate.

SuperSignal ELISA Femto Luminol/Enhancer (50 μL; Pierce) was added, the luminescence intensity (in RLU) was measured 45 times every 41 seconds by using the TriStar LB 941 luminometer (Berthold Technologies), and the values were totaled. For each assay, the same standard plasma was assayed. The value for each sample was normalized to the standard plasma.

(7.2.3) Results

Figure 18:
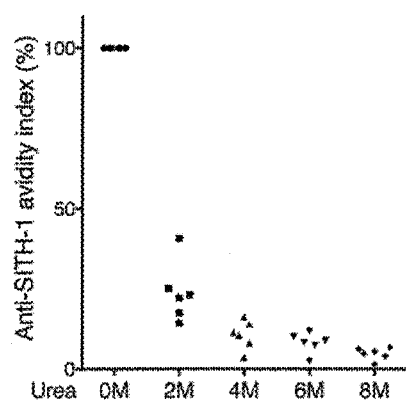
FIG. 18 shows the results of identification of suitable urea concentration for avidity index assay.

FIG. 18 confirmed that the subject samples were positive for anti-SITH-1 antibodies. It was also confirmed that high-avidity anti-SITH-1 antibodies in the subjects' plasma samples remained bound to antigen even after being washed in 2 M urea.

(7.3) Anti-SITH-1 Antibody Avidity Index

To investigate the influence of the recurrence of SITH-1 production, the anti-SITH-1 antibody avidity index (AI) was examined, because antibody AI increases with past or recurrent exposure to the antigen.

(7.3.1) Anti-SITH-1 IgG Antibody ELISA

The normal ELISA method is low in specificity, and may therefore detect antibodies which are low in avidity.

Therefore, to measure the SITH-1-specific high-avidity antibody, assay was conducted by changing only the washing step in the above (7.2.2) (the other steps were carried out as in the above (7.2.2)).

Specifically, the beads were washed three times in (i) 200 μL of 0.2% Tween 20-TBS or (ii) 200 μL of 2M urea in 0.2% Tween 20-TBS. Each plasma sample was measured in a total of four wells; in two wells the washing solution did not contain urea, and in the other two wells the washing solution contained 2 M urea to measure high-avidity anti-SITH-1 antibodies.

(7.3.2) Measurement of the Anti-SITH-1 Antibody Avidity Index

It is necessary to measure low avidity anti-SITH-1 antibody to calculate the anti-SITH-1 antibody AI. To measure low-avidity anti-SITH-1 antibodies, the plasma anti-SITH-1 IgG antibody titer was measured by using the same method as that described in the previous section but without the wash in 2 M urea.

To determine the titer of the SITH-1-specific low-avidity antibody, we estimated the nonspecific reaction of plasma by using TM2 beads instead of SITH-1-TM2 beads and plasma samples from 38 patients and 47 healthy volunteers. The AI was obtained as follows using plasma samples positive for low-avidity anti-SITH-1 antibodies:

> AI(%)=(anti-SITH-1 antibody titer measured when washing with urea/anti-SITH-1 antibody titer measured when washing without urea).

(7.3.3) Antibody Absorption Experiment

To confirm that the anti-SITH-1 IgG antibodies in the plasma bind specifically to SITH-1, we investigated whether the anti-SITH-1 antibodies in the plasma could be eliminated with SITH-1 antigens. SITH-1-biotin lysate or LATM2 lysate was reacted with Streptavidin HP SpinTrap (GE Healthcare) at room temperature for 1 h (SITH-1 column or LATM2 column). The column was centrifuged and the flow-through was discarded. Then, 200 μL plasma (diluted 1:800 in LATM2 lysate) was reacted with this column overnight at 4° C.

After centrifugation, the flow-through was recovered. This flow-through was then diluted (1:2.5 in LATM2 lysate) to a final plasma dilution ratio of 1:2000. The anti-SITH-1 antibody titer in the plasma was measured in accordance with the ELISA method described above. The result was expressed as the ratio of the anti-SITH-1 antibody titer in plasma where anti-SITH-1 antibodies were absorbed to the anti-SITH-1 antibody titer in non-absorbing plasma.

(7.3.4) Results

Figure 16:
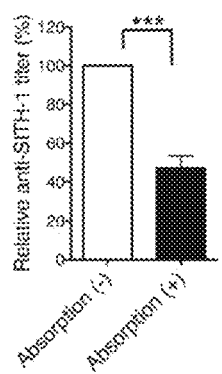
FIG. 16 shows the results of test (ELISA in which an absorption experiment is used) of antigen specificity of the anti-SITH-1 antibody.

FIG. 16 shows measurement of the anti-SITH-1 antibody titer for unabsorbed plasma [Absorption (−)] and for plasma where antibodies had been absorbed using SITH-1-biotin as an antigen [Absorption (+)]. The value for the unabsorbed plasma was defined as 100%, and was evaluated by unpaired t-test. Values are means±s.e.m., and *** indicates P<0.005. FIG. 16 confirmed that the anti-SITH-1 antibodies used were antibodies specific to SITH-1.

Figure 22:
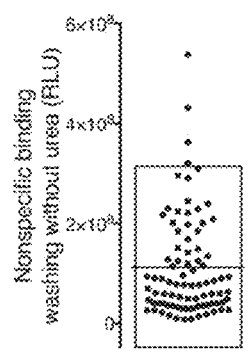
FIG. 22 shows the results of estimation of virus-specific antibody.

FIG. 22 shows that nonspecific antibody titer from patients and healthy subjects (controls) with TM2 protein-bound negative-control beads was $1.12 \times 10^8 \pm 2.05 \times 10^8$ RLU (means±2SD). Horizontal line shows the mean, and box shows ±2SD. Based on these results, it was estimated that plasma with a measured value of $3.17 \times 10^8$ RLU or more of standard plasma was positive for antibodies specific to SITH-1.

B of FIG. 12 and FIG. 22 show that anti-SITH-1 antibody AI was higher in the attempted suicide group than in controls.

(7.4) Indirect Fluorescent Antibody Assay of Anti-SITH-1 Antibody in Suicide Attempters To examine SITH-1 protein expression in suicide attempters, SITH-1 protein in plasma was examined by indirect fluorescent antibody assay. The indirect fluorescent antibody assay was carried out by a method similar to that described in the above (5.2.2). Then, demographic and antibody reactivity details (age, gender, presence of anti-SITH-1 antibodies, presence of autoantibodies) of subjects who had attempted suicide and healthy subjects (controls) were investigated.

(7.4.1) Results

Figure 19:
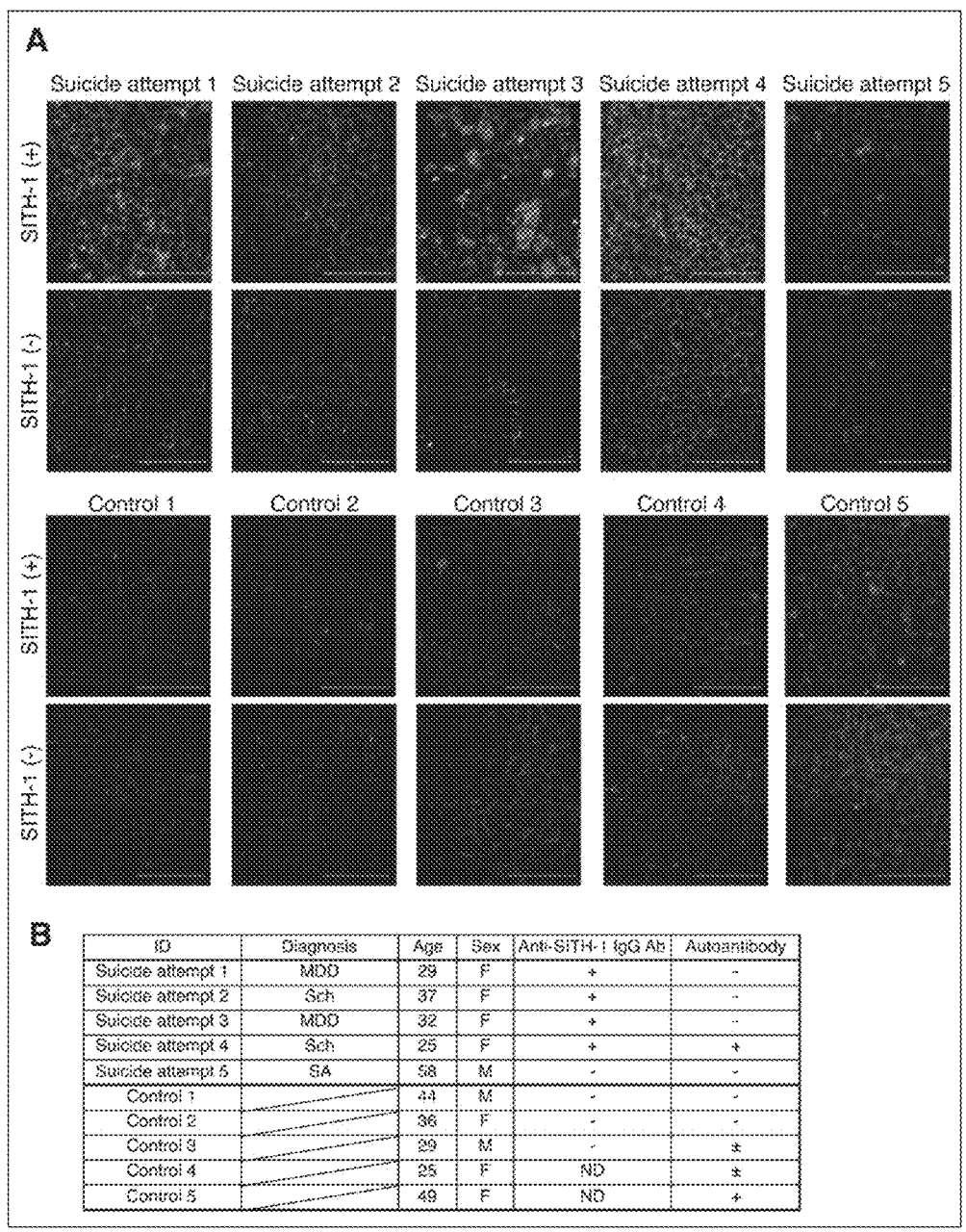
FIG. 19 shows the results of indirect fluorescent antibody detection of anti-SITH-1 antibodies in the plasma of representative subjects who had attempted suicide. A of FIG. 19 is a view showing the results of immunofluorescence staining of SITH-1 in plasma from suicide attempters and healthy subjects (controls). B of FIG. 19 is a view showing demographic and antibody reactivity details (age, gender, presence of anti-SITH-1 antibodies, and presence of autoantibodies) of subjects who had attempted suicide and healthy subjects (controls).

A of FIG. 19 confirmed greater SITH-1 protein expression in the suicide attempters than in the healthy subjects (controls). Meanwhile, B of FIG. 19 shows that control 4 and control 5 were positive for autoantibodies. This made it difficult to determine the presence or absence of anti-SITH-1 antibodies. In B of FIG. 19, + indicates positive, ± indicates weakly positive, and − indicates negative, and ND indicates not determined. Scale bars are 100 μm. Note that the results for the plasma samples in which antibodies could be determined were the same as those for the measurement of antibodies by using ELISA (see D of FIG. 10).

(7.5) Comparison of Anti-SITH-1 Antibody Titers and Anti-SITH-1 AIs Across Different Racial Groups HHV-6B is the predominant virus variant in infant infections in the USA, Europe, and Japan, and infection with HHV-6 variant A (HHV-6A) is rare. However, HHV-6A is the variant having a high infection rate in the African population. Although HHV-6A does not encode SITH-1, it encodes the protein U91, which is homologous with SITH-1 and which can be produced in the intermediate early phase of HHV-6A productive infection. SITH-1 and U91, although differing in function, have an amino acid identity of approximately 90%, and are considered cross-reactive. Therefore, the influence of U91 on SITH-1 titration in subjects potentially infected with HHV-6A was examined. Commercially available sera from 40 healthy African-Americans and 38 Caucasians were obtained from Kohjin Bio, and plasma was obtained from 40 healthy Japanese who served as controls for the subjects who had attempted suicide.

(7.5.1) Results

Figure 23:
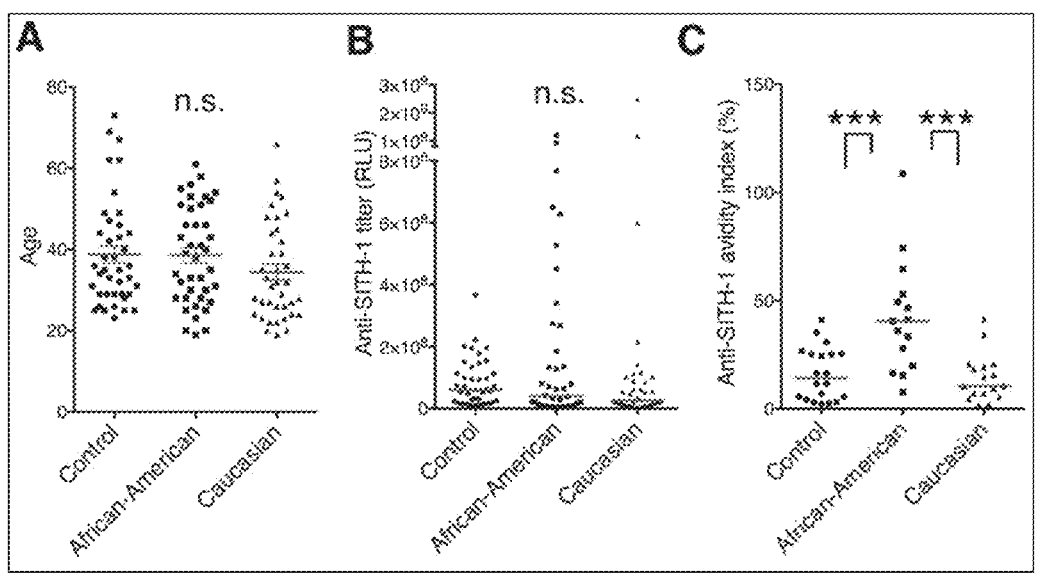
FIG. 23 shows the results of comparison of anti-SITH-1 antibody titers and anti-SITH-1 AIs across different racial groups. A of FIG. 23 is a view showing the results of comparing ages of Japanese controls, African-Americans, and Caucasians. B of FIG. 23 is a view showing anti-SITH-1 antibody titers in plasma of the Japanese controls and serum of the African-Americans and the Caucasians. C of FIG. 23 is a view showing anti-SITH-1 antibody AI in plasma of the Japanese controls and serum of the African-Americans and the Caucasians.

A of FIG. 23 shows that a difference in age was not observed among the Japanese controls, the African-Americans, the Caucasians. B of FIG. 23 shows that there was no difference in anti-SITH-1 antibody titer among the three. However, C of FIG. 23 shows that anti-SITH-1 antibody AI was higher in the African-Americans than in the Japanese and the Caucasians.

Note that in B and C of FIG. 23, (i) horizontal lines show median values, (ii) *** indicates P<0.001, and (iii) n.s. indicates that there was not significant difference. B and C of FIG. 23 show the results of Mann-Whitney U-test.

(7.6) Relationship Between SITH-1 and Beck Depression Index (BDI) Total Score

To examine whether or not SITH-1 in suicide attempters are correlated with BDI total score, an experiment was conducted to compare anti-SITH-1 antibody Avidity Index (AI) and BDI total score. Anti-SITH-1 antibody Avidity Index was measured by a method similar to that described above.

(7.6.1) Results

It was confirmed that, consistent with the mouse model that showed depressive symptoms long after SITH-1 production, the Beck Depression Inventory (BDI) score (an index of the severity of depression) was positively correlated with the anti-SITH-1 AI (see C of FIG. 12).

(7.7) Comparison of Anti-SITH-1 Antibody AIs in Various Mental Disorders

An experiment was conducted to compare between anti-SITH-1 antibody AIs in (i) healthy subjects (controls), (ii) patients with mood disorders (MD), (iii) patients with schizophrenia or other psychotic disorders (SCH), and (iv) patients with other mental disorders (Others). Anti-SITH-1 antibody Avidity Index was measured by a method similar to that described above.

(7.7.1) Results

D of FIG. 12 confirmed that, in relation to the psychiatric diagnosis in the attempted suicide group, the anti-SITH-1 antibody AI was higher in subjects with mood disorders than in healthy subjects (controls).

(7.8) Relationship Between CFS and Anti-SITH-1 Antibody

The study enrolled 38 subjects (11 males, 27 females) diagnosed with chronic fatigue syndrome (CFS) after an initial consultation at the Osaka City University Hospital Fatigue Clinical Center, and 47 healthy volunteers as their age-matched controls. CFS was diagnosed by using the diagnostic criteria (revised 1994) of the US Centers for Disease Control and Prevention. The wide-ranging symptoms experienced by CFS subjects were scored by using the Japanese-language version of the Chalder Fatigue Scale 17 and a 64-item fatigue questionnaire developed by Osaka City University Hospital (see Literature 6). This study was approved by the Ethics Committees of the Jikei University School of Medicine, Tokyo Metropolitan Matsuzawa Hospital, Tokyo Metropolitan Institute of Medical Science, Soiken Inc., Soiken Clinic, and Osaka City University. Written informed consent was obtained from each subject.

(7.8.1) Results

Figure 24:
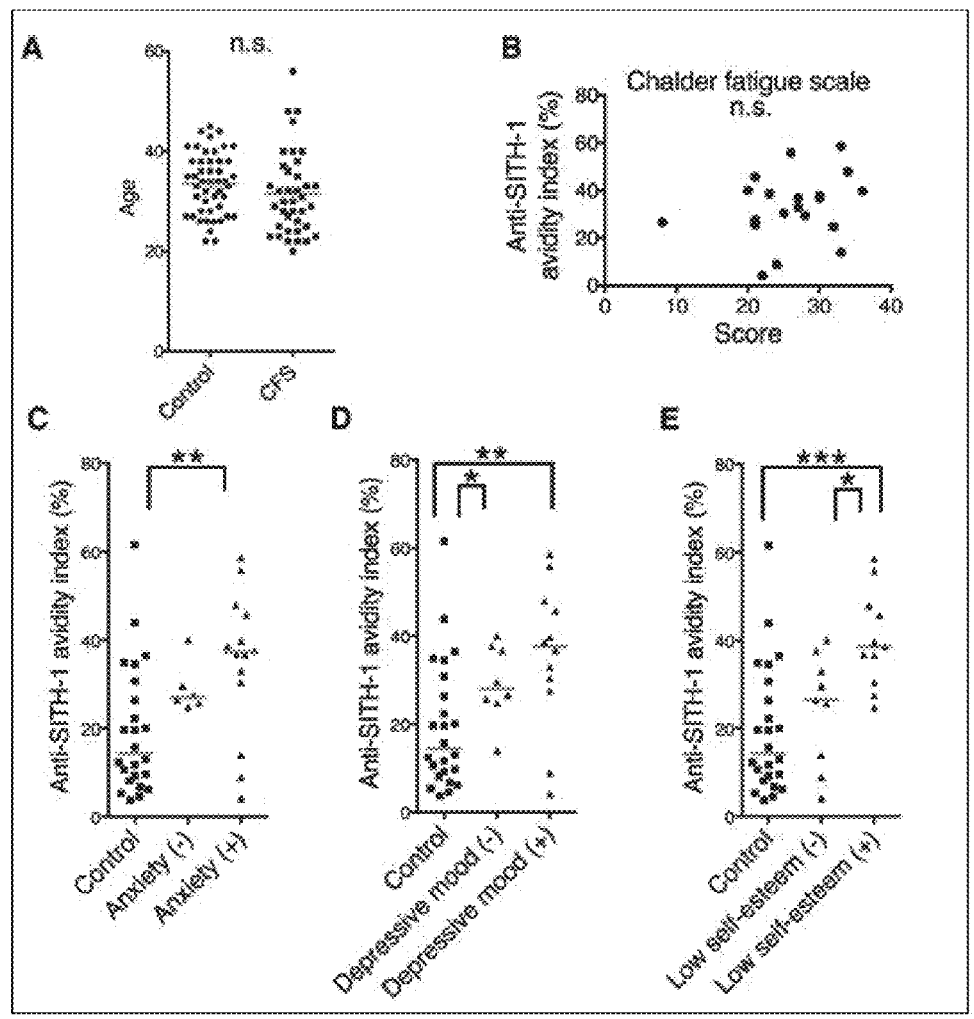
FIG. 24 shows the results of examining a relationship between SITH-1 and chronic fatigue syndrome (CFS). A of FIG. 24 is a view showing a distribution of current ages of healthy subjects (controls) and of patients with CFS. B of FIG. 24 is a view showing the results of examining a relationship between anti-SITH-1 antibody AI and fatigue, which is a primary symptom of CFS. C through E of FIG. 24 are views showing anti-SITH-1 antibody AI in CFS patients with or without depressive symptoms of anxiety (C), depressive mood (D), and low self-esteem (E).

A of FIG. 24 shows that a significant difference in age among the healthy subject group and the CFS patient population was not observed. The relationship between HHV-6 and CFS has been the subject of debate for many years, and patients with CFS frequently have depressive disorders. B of FIG. 24 shows that there was no correlation between anti-SITH-1 antibody AI and fatigue, which is a primary symptom of CFS. The Chalder fatigue scale was used to quantify the patients' fatigue. n.s. indicates that there was no significant difference. C through E of FIG. 24 show that SITH-1 seems to be related to the depressive mood associated with CFS, but not with CFS itself. Note that in C through E of FIG. 24, (i) horizontal lines show median values, (ii) * indicates P<0.05, (iii)  indicates P<0.01, and (iv) * indicates P<0.005.

(7.9) Relationship Between Anti-HHV-6B Antibody and Anti-SITH-1 Antibody AI

An experiment was conducted to investigate a relationship between anti-HHV-6B antibody titer and anti-SITH-1 antibody AI in subjects who were diagnosed as having MD (mood disorder) and healthy subjects (controls). Anti-HHV-6B antibody titer and anti-SITH-1 antibody Avidity Index were measured by a method similar to that described above.

(7.9.1) Results

E of FIG. 12 shows a relationship between anti-HHV-6B antibody titer and anti-SITH-1 antibody AI in patients who were diagnosed as having MD and healthy subjects (controls). In E of FIG. 12, low AI indicates subjects who had a lower AI than the median of each group, and high AI indicates those who had a higher AI than the median. Horizontal lines show median values. * indicates P<0.05, ** indicates P<0.01, and n.s. indicates that there was no significant difference. The median of the anti-SITH-1 antibody AI in the MD group was 26.5%, and the median of the anti-SITH-1 antibody AI in the controls was 14.2%.

E of FIG. 12 confirmed that those patients with mood disorders who had high anti-SITH-1 antibody AIs also had low anti-HHV-6B antibody titers. Among the healthy subject group, there was no difference in anti-HHV-6 antibody titer between a group having high anti-SITH-1 antibody AI and a group having low anti-SITH-1 antibody AI.

In patients with high anti-SITH-1 antibody AI, HHV-6B antibody titers are generally expected to be high because HHV-6B is likely reactivated frequently. Therefore, these patients are considered to show a low anti-HHV-6B immune response.

(7.10) Relationship Between Anti-SITH-1 Antibody and Amount of HHV-6 in Mood Disorder Patients An experiment was conducted to investigate a relationship between anti-SITH-1 antibody and the amount of HHV-6 in patients diagnosed with a depressive disorder. Anti-SITH-1 antibody titer and the amount of HHV-6 were measured by a method similar to that described above. Note that the subjects were 40 patients (17 females and 23 males) who were diagnosed with a depressive disorder at Jikei University Hospital and Jikei University Kashiwa Hospital. 19 subjects were positive for an anti-SITH-1 antibody, and 21 subjects were negative for an anti-SITH-1 antibody.

(7.10.1) Results

Figure 25:
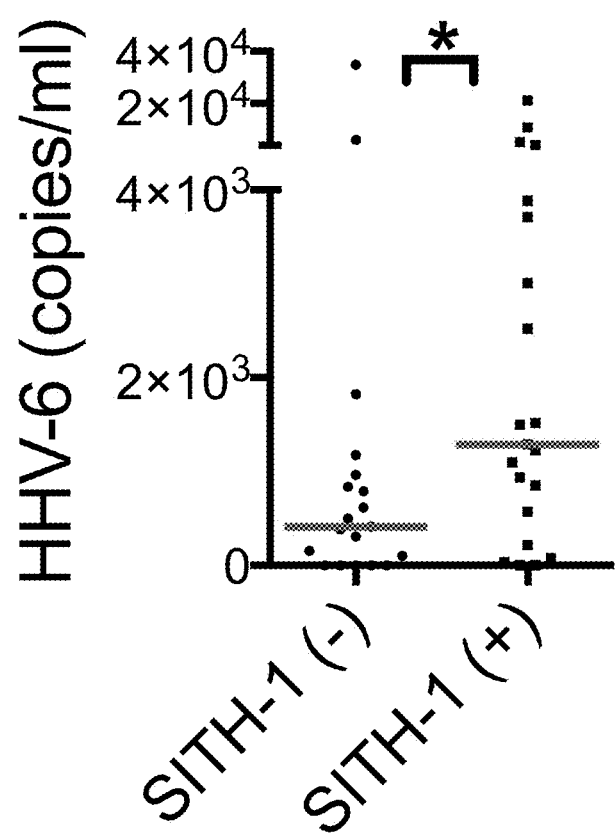
FIG. 25 shows the amount of HHV-6 in specimens collected from depressive disorder patients.

FIG. 25 confirmed that the amounts of HHV-6 in specimens of the depressive disorder patients who were positive for an anti-SITH-1 antibody were significantly greater than those in specimens of the depressive disorder patients who were negative for an anti-SITH-1 antibody. Note that * indicates P<0.05.

These results suggest that HHV-6 in saliva persistently brings about the effect of promoting, through SITH-1 expression in the olfactory epithelium, an onset of a mood disorder even after an onset of a mood disorder such as depressive disorder. This suggests that it may be possible to treat a mood disorder such as depressive disorder by reducing HHV-6 in saliva and/or preventing the olfactory epithelium from being infected with HHV-6.

(8) Other Remarks

In Examples above, statistical analysis, if at all, was made by the following method unless specified otherwise.

Statistical Analysis

To compare two different groups, the Mann-Whitney U-test was used as the nonparametric test and the unpaired t-test was used as the parametric test. To compare two corresponding groups, the paired t-test was used as the parametric test. P<0.05 was considered significant. Spearman's rank correlation coefficient was used to determine correlations between variables. Statistical analyses were performed with SPSS Statistics version 19 (IBM) and Prism 5 (GraphPad).

REFERENCE DOCUMENTS

[Literature 1] K. Kondo, T. Kondo, T. Okuno, M. Takahashi, K. Yamanishi, Latent human herpesvirus 6 infection of human monocytes/macrophages. J. Gen. Virol. 72, 1401 (1991)

[Literature 2] K. Kondo et al., Recognition of a novel stage of betaherpesvirus latency in human herpesvirus 6. J. Virol. 77, 2258 (2003)

[Literature 3] N. Hayashi et al., Psychiatric disorders and clinical correlates of suicide patients admitted to a psychiatric hospital in Tokyo. BMC Psychiatry 10, 109 (2010)

[Literature 4] K. Kondo, K. Shimada, J. Sashihara, K. Tanaka-Taya, K. Yamanishi, Identification of human herpesvirus 6 latency-associated transcripts. J. Virol. 76, 4145 (2002)

[Literature 5] T. Sugino, T. Shirai, Y. Kajimoto, O. Kajimoto, L-ornithine supplementation attenuates physical fatigue in healthy volunteers by modulating lipid and amino acid metabolism. Nutr. Res. 28, 738 (2008)

[Literature 6] H. Koyama et al., Fatigue is a predictor for cardiovascular outcomes in patients undergoing hemodialysis. Clin. J. Am. Soc. Nephrol. 5, 659 (2010)

[Literature 7] W. Kamitani et al., Glial expression of Borna disease virus phosphoprotein induces behavioral and neurological abnormalities in transgenic mice. Proc. Natl. Acad. Sci. U.S.A. 100, 8969 (2003)

[Literature 8] Y. Takakura et al., Tamavidins—novel avidin-like-biotin-binding proteins from the Tamogitake mushroom. FEBS J. 276, 1383 (2009)

[Literature 9] K. Kondo, J. Xu, E. S. Mocarski, Human cytomegalovirus latent gene expression in granulocyte-macrophage progenitors in culture and in seropositive individuals. Proc. Natl. Acad. Sci. U.S.A. 93, 11137 (1996)

[Literature 10] J. Sambrook et al. Molecular Cloning, A Laboratory Manual, 2d Ed., Cold Spring Harbor Laboratory (1989)

[Literature 11] Harberts et al, PNAS vol. 108 No. 33, 13734-13739, 2011

[Literature 12] Oltvai Z N, Milliman C L, Korsmeyer S J. Bcl-2 heterodimerizes in vivo with a conserved homolog, Bax, that accelerates programmed cell death. Cell. 1993 Aug. 27; 74(4):609-19

[Literature 13] Kosten et al. Neuropsychopharmacology, 2008 June; 33(7):1545-58

[Literature 14] Huang et al. J Pharmacol Sci. 2007 May; 104(1):61-72

[Literature 15] Murray et al. Eur J Pharmacol. 2007 Aug. 13; 569(1-2):41-7

[Literature 16] Xu et al. Neuropsychopharmacology, 2003 January; 28(1):53-62

[Literature 17] Malkesman et al. Molecular Psychiatry 17, 770-780, 2012

[Literature 18] Nancy A Shanahan, Lady P Velez, Virginia L Masten, and Stephanie C Dulawa Essential role for orbitofrontal 5-HT1B receptors in OCD-like behavior and SRI response in mice Biol Psychiatry. 2011 Dec. 1; 70(11): 1039-1048

INDUSTRIAL APPLICABILITY

An embodiment of the present invention makes it possible to determine, with higher sensitivity and higher specificity than are the cases of the conventional technologies, whether or not a subject has a mood disorder. This makes it possible to provide a novel method which is effective in treating and/or preventing a mood disorder.

SEQUENCE LISTING

SK14112 Sequence listing

The invention claimed is:

1. A method of treating or preventing depression that derives from human herpes virus 6 (HHV-6) SITH-1 expression in olfactory epithelial cells, comprising the step of: administering to a subject in need thereof an effective amount of an HHV-6 infection inhibitor to the olfactory epithelial cells of said subject, wherein the administration is done using a nasal spray.

2. A method of treating or preventing depression, comprising the steps of:
   a) obtaining a biological sample from a subject;
   b) measuring an anti-SITH-1 antibody level in said biological sample; and
   c) in a case where the anti-SITH-1 antibody level is high, administering an effective amount of an HHV-6 infection inhibitor to the olfactory epithelial cells of said subject.

3. An isolated transformed cell from the olfactory epithelium, wherein said transformed cell expresses HHV-6 SITH-1.

4. A mood disorder animal model, wherein said animal is a non-human animal, and wherein said animal is generated by transfecting and/or infecting cells of the olfactory epithelium of said animal with an HHV-6 SITH-1 gene expression construct.

5. A method of screening test substances as potential mood disorder treatment or prevention candidate substances, comprising the steps of:
   a) administering a test substance to the mood disorder animal model of claim 4; and
   b) determining whether or not the test substance is a candidate substance for mood disorder treatment or prevention, wherein the determining analyzes the results of at least one of the following tests within the mood disorder animal model:
   1) a behavioral abnormality test,
   2) a stress vulnerability test,
   3) a test for detecting apoptosis in an olfactory bulb,
   4) a test for detecting an abnormality of a hypothalamus, and/or
   5) a test for detecting an abnormality of a stress response factor in a brain.

6. A method of treating or preventing a mood disorder that derives from human herpes virus 6 (HHV-6) SITH-1 expression in olfactory epithelial cells, comprising the step of: administering to a subject in need thereof an effective amount of an HHV-6 infection inhibitor to the olfactory epithelial cells of said subject, wherein the administration is done using a nasal spray.

* * * * *

```
                        SEQUENCE LISTING

<160> NUMBER OF SEQ ID NOS: 36

<210> SEQ ID NO 1
<211> LENGTH: 159
<212> TYPE: PRT
<213> ORGANISM: Human herpesvirus 6

<400> SEQUENCE: 1

Met Gly Tyr Glu Glu Lys Val Ser Ala Thr Gly Lys Thr Arg Leu Lys
1               5                   10                  15

Ile Leu Ala Cys Leu Ile Val Leu Ile Leu Ala Ala Ala Ile Thr Met
            20                  25                  30

Leu Thr Leu Glu Ile Ile Ser Asn Gln Lys Arg Thr Thr Thr Asp Leu
        35                  40                  45

Glu Ala Val Thr Val Ala Leu Lys His Val Ser Thr Ser Leu Ala Ser
    50                  55                  60

Cys Thr Glu Ser Thr Thr Ser Val His Thr Asp Ser Val Thr Ser Gln
65                  70                  75                  80

Pro Thr Lys Asn Lys Glu Ser Arg Lys Lys Ile Glu Gly Lys Ser Pro
                85                  90                  95

Ser Trp Val Gln Ala Leu Thr Thr Ala Ser Gly Ile Ile Leu Leu Phe
            100                 105                 110

Cys Ile Met Met Ile Phe Ile Thr Cys Ser Trp Thr Thr Glu Lys Asp
        115                 120                 125

Thr Glu Lys Ser Glu Val Gln Ser Tyr Ala Ser Ser Val Glu Thr Leu
    130                 135                 140

Asp Ser Leu Asn Glu Ala Ile Ile Pro Lys Thr Glu Met Asn Val
145                 150                 155

<210> SEQ ID NO 2
<211> LENGTH: 480
<212> TYPE: DNA
<213> ORGANISM: Human herpesvirus 6

<400> SEQUENCE: 2
atgggatatg aagaaaaagt gtcagctact ggaaagactc gtttaaagat actggcatgt      60
ctgatcgttt taatactagc tgcggcaata actatgttaa cgctggaaat tatatcgaac     120
caaaaacgta ccactactga tctcgaagct gtgactgtgg cgctgaagca tgtaagcaca     180
tctcttgcca gctgcactga atccactact tctgtacata ccgattctgt gacgagccaa     240
cccacgaaaa acaaagaatc gaggaaaaaa attgaaggga atctccaag ttgggttcag      300
```
gctttaacta cagcatctgg aattatccta ctgttttgta taatgatgat attcattaca    360
tgttcctgga ccacagaaaa agatacagag aagagtgaag tgcaatctta tgcttcttca    420
gtagagactt tagactcttt aaatgaggct attataccga aaactgaaat gaatgtgtaa    480

<210> SEQ ID NO 3
<211> LENGTH: 1795
<212> TYPE: DNA
<213> ORGANISM: Human herpesvirus 6

<400> SEQUENCE: 3
aggctctgct ggaggctctg ctggaggcct tgctgaaggc tctgctggag gccctgctgg     60
aggtcttgct ggaggctctg ctggaggctc tgctggaggc tctgctggag gctctgctgg    120
aggctctgct ggaggctctg ctggaggctc tgtcagagac ctcggtgaaa gttttactca    180
gaggtttatc agagttttcg ccattagttt ggttagaagt ttcagattta ttttcggtgg    240
aactgcagtt aggtttcatg tcagtacatt catcaccgtt agaagtgcta ttcatggtgc    300
tgttgccact gttggatttg ttaaaagcag taaatgagct aggattggaa tgactccgaa    360
tagctaataa atttgagcat tttcttcgaa tggatcataa tcagagggat agccatctaa    420
tttaaagact tccattttat cactgttgca atcacttcta atggagtatc tggatacatt    480
ttttctacat cttttcatc ccctccaaca tggatctgtg cagcgttaat aagccagcgg    540
agttaattaa atcgtcttcc atgttagaca gttcctgttt catggcagcc ttcactgatg    600
caccaatact ttggatgcaa gtgccaacgg actgagctag gatgtaaaag aagatattct    660
aattttgaat tcttcagatg ctccttcttc cacattactg aataggaca cattcttgga    720 agcgatgtcg ttggaagact ctgggatgaa aagatcacag gcttccagtt ctggaaaaag    780
caggctttca aaggacacat cacacttgag actctcttcc aatatttctt tgatggattc    840
ttccaccact ggatcgggat ggtagctata tatactatat aaggagatta ccaccaccac    900
ctctttcttt gcagagatta ttctctgctt gaaaatctgt aacactgatc atgatgggat    960
atgaagaaaa agtgtcagct actggaaaga ctcgtttaaa gatactggca tgtctgatcg   1020
ttttaatact agctgcggca ataactatgt taacgctgga aattatatcg aaccaaaaac   1080
gtaccactac tgatctcgaa gctgtgactg tggcgctgaa gcatgtaagc acatctcttg   1140
ccagctgcac tgaatccact acttctgtac ataccgattc tgtgacgagc caacccacga   1200
aaaacaaaga atcgaggaaa aaaattgaag ggaaatctcc aagttgggtt caggctttaa   1260
ctacagcatc tggaattatc ctactgtttt gtataatgat gatattcatt acatgtccct   1320
ggaccacaga aaagataca gagaagagtg aagtgcaatc ttatgctcct tcagtagaga   1380
ctttagaccc tttaaatgag gctattatac cgaaaactga atgaatgtg taatgtctgt   1440 atttttcttt acagagatgt acggagagtt tatatttggg gaaaatacct gactgttctg   1500
cctatatgcg aatgttaaag tatgtataat ataaattctt accttttaag agtgattcaa   1560
ggtggaggtt tctttggaga ttgattccag gtggtggttt cgggtgcaat caatctttct   1620
tctgggcggg aagaaaatcc agcaatccaa taattgatgg gatgtaatca atgtcacaaa   1680
tctgtaagat taaatgtgaa cagtataaat tctttcgtgc ttatcaaatt acaattatgc   1740
gcatgaaaat atcattaaat tgttttaaac attcttaaaa aaaaaaaaa aaaaa          1795

<210> SEQ ID NO 4
<211> LENGTH: 19
<212> TYPE: DNA
<213> ORGANISM: Artificial Sequence

```
<220> FEATURE:
<223> OTHER INFORMATION: Primer Sequence

<400> SEQUENCE: 4
ccagctgcac tgaatccac                                              19

<210> SEQ ID NO 5
<211> LENGTH: 19
<212> TYPE: DNA
<213> ORGANISM: Artificial Sequence
<220> FEATURE:
<223> OTHER INFORMATION: Primer Sequence

<400> SEQUENCE: 5
gcctgaaccc aacttggag                                              19

<210> SEQ ID NO 6
<211> LENGTH: 30
<212> TYPE: DNA
<213> ORGANISM: Artificial Sequence
<220> FEATURE:
<223> OTHER INFORMATION: Probe Sequence

<400> SEQUENCE: 6
cttctgtaca taccgattct gtgacgagcc                                  30

<210> SEQ ID NO 7
<211> LENGTH: 19
<212> TYPE: DNA
<213> ORGANISM: Artificial Sequence
<220> FEATURE:
<223> OTHER INFORMATION: Primer Sequence

<400> SEQUENCE: 7
tgaaggtcgg tgtgaacgg                                              19

<210> SEQ ID NO 8
<211> LENGTH: 24
<212> TYPE: DNA
<213> ORGANISM: Artificial Sequence
<220> FEATURE:
<223> OTHER INFORMATION: Primer Sequence

<400> SEQUENCE: 8
ccatgtagtt gaggtcaatg aagg                                        24

<210> SEQ ID NO 9
<211> LENGTH: 24
<212> TYPE: DNA
<213> ORGANISM: Artificial Sequence
<220> FEATURE:
<223> OTHER INFORMATION: Probe Sequence

<400> SEQUENCE: 9
tggtcaccag ggctgccatt tgca                                        24

<210> SEQ ID NO 10
<211> LENGTH: 25
<212> TYPE: DNA
<213> ORGANISM: Artificial Sequence
<220> FEATURE:
<223> OTHER INFORMATION: Primer Sequence

<400> SEQUENCE: 10
gatgctcctt cttccacatt actgg                                       25
```

<210> SEQ ID NO 11
<211> LENGTH: 26
<212> TYPE: DNA
<213> ORGANISM: Artificial Sequence
<220> FEATURE:
<223> OTHER INFORMATION: Primer Sequence

<400> SEQUENCE: 11
catcccatca attattggat tgctgg                                              26

<210> SEQ ID NO 12
<211> LENGTH: 24
<212> TYPE: DNA
<213> ORGANISM: Artificial Sequence
<220> FEATURE:
<223> OTHER INFORMATION: Primer Sequence

<400> SEQUENCE: 12
gacacattct tggaagcgat gtcg                                                24

<210> SEQ ID NO 13
<211> LENGTH: 26
<212> TYPE: DNA
<213> ORGANISM: Artificial Sequence
<220> FEATURE:
<223> OTHER INFORMATION: Primer Sequence

<400> SEQUENCE: 13
gaaaccacca cctggaatca atctcc                                              26

<210> SEQ ID NO 14
<211> LENGTH: 73
<212> TYPE: DNA
<213> ORGANISM: Artificial Sequence
<220> FEATURE:
<223> OTHER INFORMATION: Primer Sequence

<400> SEQUENCE: 14
cttatgagta tttcttccag ggtactcgag gctgggtagt ccccacctttctagattttt          60 ttttttttttttt                                                             73

<210> SEQ ID NO 15
<211> LENGTH: 30
<212> TYPE: DNA
<213> ORGANISM: Artificial Sequence
<220> FEATURE:
<223> OTHER INFORMATION: Primer Sequence

<400> SEQUENCE: 15
cttatgagta tttcttccag ggtactcgag                                          30

<210> SEQ ID NO 16
<211> LENGTH: 23
<212> TYPE: DNA
<213> ORGANISM: Artificial Sequence
<220> FEATURE:
<223> OTHER INFORMATION: Primer Sequence

<400> SEQUENCE: 16
gcttcgagat cagtagtggt acg                                                 23

<210> SEQ ID NO 17
<211> LENGTH: 25
<212> TYPE: DNA
<213> ORGANISM: Artificial Sequence
<220> FEATURE:
<223> OTHER INFORMATION: Primer Sequence

<400> SEQUENCE: 17
gctgggtagt ccccaccttt ctaga                                              25

<210> SEQ ID NO 18
<211> LENGTH: 26
<212> TYPE: DNA
<213> ORGANISM: Artificial Sequence
<220> FEATURE:
<223> OTHER INFORMATION: Primer Sequence

<400> SEQUENCE: 18
ctgaagcatg taagcacatc tcttgc                                             26

<210> SEQ ID NO 19
<211> LENGTH: 25
<212> TYPE: DNA
<213> ORGANISM: Artificial Sequence
<220> FEATURE:
<223> OTHER INFORMATION: Primer Sequence

<400> SEQUENCE: 19
gctgggtagt ccccaccttt ctaga                                              25

<210> SEQ ID NO 20
<211> LENGTH: 22
<212> TYPE: DNA
<213> ORGANISM: Artificial Sequence
<220> FEATURE:
<223> OTHER INFORMATION: Primer Sequence

<400> SEQUENCE: 20
tccggagaac attctcatca ca                                                 22

<210> SEQ ID NO 21
<211> LENGTH: 23
<212> TYPE: DNA
<213> ORGANISM: Artificial Sequence
<220> FEATURE:
<223> OTHER INFORMATION: Primer Sequence

<400> SEQUENCE: 21
gtggaggttt ctttggagat tga                                                23

<210> SEQ ID NO 22
<211> LENGTH: 28
<212> TYPE: DNA
<213> ORGANISM: Artificial Sequence
<220> FEATURE:
<223> OTHER INFORMATION: Probe Sequence

<400> SEQUENCE: 22
tcgggtgcaa tcaatctttc ttctgggc                                           28

<210> SEQ ID NO 23
<211> LENGTH: 22
<212> TYPE: DNA
<213> ORGANISM: Artificial Sequence
<220> FEATURE:
<223> OTHER INFORMATION: Primer Sequence

<400> SEQUENCE: 23
gctcttggag tcagagcttt tg                                                 22

<210> SEQ ID NO 24
<211> LENGTH: 21
<212> TYPE: DNA
<213> ORGANISM: Artificial Sequence
<220> FEATURE:
<223> OTHER INFORMATION: Primer Sequence

<400> SEQUENCE: 24
ttcccgacaa tagaagtgca g                                              21

<210> SEQ ID NO 25
<211> LENGTH: 23
<212> TYPE: DNA
<213> ORGANISM: Artificial Sequence
<220> FEATURE:
<223> OTHER INFORMATION: Primer Sequence

<400> SEQUENCE: 25
gacaatcaca tgcctggata atg                                            23

<210> SEQ ID NO 26
<211> LENGTH: 24
<212> TYPE: DNA
<213> ORGANISM: Artificial Sequence
<220> FEATURE:
<223> OTHER INFORMATION: Primer Sequence

<400> SEQUENCE: 26
tgtaagcgtg tggtaatgga ctaa                                           24

<210> SEQ ID NO 27
<211> LENGTH: 24
<212> TYPE: DNA
<213> ORGANISM: Artificial Sequence
<220> FEATURE:
<223> OTHER INFORMATION: Probe Sequence

<400> SEQUENCE: 27
agcagctggc gaaaagtgct gtgc                                           24

<210> SEQ ID NO 28
<211> LENGTH: 20
<212> TYPE: DNA
<213> ORGANISM: Artificial Sequence
<220> FEATURE:
<223> OTHER INFORMATION: Primer Sequence

<400> SEQUENCE: 28
ctctggagag cgtgaatggg                                                20

<210> SEQ ID NO 29
<211> LENGTH: 24
<212> TYPE: DNA
<213> ORGANISM: Artificial Sequence
<220> FEATURE:
<223> OTHER INFORMATION: Primer Sequence

<400> SEQUENCE: 29
gtccttatgg ttttcttcgt tggg                                           24

<210> SEQ ID NO 30
<211> LENGTH: 28
<212> TYPE: DNA
<213> ORGANISM: Artificial Sequence
<220> FEATURE:
<223> OTHER INFORMATION: Probe Sequence

```
<400> SEQUENCE: 30
aggtctgacg acgacatcac tggctgac                                      28

<210> SEQ ID NO 31
<211> LENGTH: 19
<212> TYPE: DNA
<213> ORGANISM: Artificial Sequence
<220> FEATURE:
<223> OTHER INFORMATION: Primer Sequence

<400> SEQUENCE: 31
cgcgagcaca gcttctttg                                                19

<210> SEQ ID NO 32
<211> LENGTH: 19
<212> TYPE: DNA
<213> ORGANISM: Artificial Sequence
<220> FEATURE:
<223> OTHER INFORMATION: Primer Sequence

<400> SEQUENCE: 32
cgaccagcgc agcgatatc                                                19

<210> SEQ ID NO 33
<211> LENGTH: 24
<212> TYPE: DNA
<213> ORGANISM: Artificial Sequence
<220> FEATURE:
<223> OTHER INFORMATION: Probe Sequence

<400> SEQUENCE: 33
cacacccgcc accagttcgc catg                                          24

<210> SEQ ID NO 34
<211> LENGTH: 23
<212> TYPE: DNA
<213> ORGANISM: Artificial Sequence
<220> FEATURE:
<223> OTHER INFORMATION: Primer Sequence

<400> SEQUENCE: 34
tccgcatggg tgaagaatac ttc                                           23

<210> SEQ ID NO 35
<211> LENGTH: 18
<212> TYPE: DNA
<213> ORGANISM: Artificial Sequence
<220> FEATURE:
<223> OTHER INFORMATION: Primer Sequence

<400> SEQUENCE: 35 tgagggcgt ggagttgg                                                  18

<210> SEQ ID NO 36
<211> LENGTH: 25
<212> TYPE: DNA
<213> ORGANISM: Artificial Sequence
<220> FEATURE:
<223> OTHER INFORMATION: Probe Sequence

<400> SEQUENCE: 36
caacagaagt cccgctgctc ggctg                                         25
```